US011535665B2

(12) United States Patent
Limberis et al.

(10) Patent No.: US 11,535,665 B2
(45) Date of Patent: Dec. 27, 2022

(54) AAV-MEDIATED EXPRESSION OF ANTI-INFLUENZA ANTIBODIES AND METHODS OF USE THEREOF

(71) Applicant: The Trustees of the University of Pennsylvania, Philadelphia, PA (US)

(72) Inventors: Maria P. Limberis, Philadelphia, PA (US); Anna P. Tretiakova, Philadelphia, PA (US); James M. Wilson, Philadelphia, PA (US)

(73) Assignee: The Trustees of The University of Pennsylvania, Philadelphia, PA (US)

( * ) Notice: Subject to any disclaimer, the term of this patent is extended or adjusted under 35 U.S.C. 154(b) by 942 days.

(21) Appl. No.: 15/571,708

(22) PCT Filed: May 12, 2016

(86) PCT No.: PCT/US2016/032063
§ 371 (c)(1),
(2) Date: Nov. 3, 2017

(87) PCT Pub. No.: WO2016/200543
PCT Pub. Date: Dec. 15, 2016

(65) Prior Publication Data
US 2018/0155412 A1    Jun. 7, 2018

Related U.S. Application Data

(60) Provisional application No. 62/323,348, filed on Apr. 15, 2016, provisional application No. 62/161,192, filed on May 13, 2015.

(51) Int. Cl.
| | | |
|---|---|---|
| *A61K 39/12* | (2006.01) | |
| *C12N 7/00* | (2006.01) | |
| *C12N 15/86* | (2006.01) | |
| *C07K 16/10* | (2006.01) | |
| *A61K 9/00* | (2006.01) | |
| *A61K 39/00* | (2006.01) | |

(52) U.S. Cl.
CPC ........ *C07K 16/1018* (2013.01); *A61K 9/0019* (2013.01); *A61K 9/0043* (2013.01); *A61K 39/12* (2013.01); *C12N 7/00* (2013.01); *C12N 15/86* (2013.01); *A61K 2039/505* (2013.01); *A61K 2039/507* (2013.01); *C07K 2317/21* (2013.01); *C12N 2710/10043* (2013.01); *C12N 2760/16134* (2013.01); *C12N 2760/16234* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 5,139,941 A | 8/1992 | Muzyczka et al. |
| 5,478,745 A | 12/1995 | Samulski et al. |
| 5,741,683 A | 4/1998 | Zhou et al. |
| 5,811,524 A | 9/1998 | Brams et al. |
| 5,830,462 A | 11/1998 | Crabtree et al. |
| 5,834,266 A | 11/1998 | Crabtree et al. |
| 5,869,337 A | 2/1999 | Crabtree et al. |
| 5,871,753 A | 2/1999 | Crabtree et al. |
| 6,011,018 A | 1/2000 | Crabtree et al. |
| 6,015,709 A | 1/2000 | Natesan |
| 6,043,082 A | 3/2000 | Crabtree et al. |
| 6,046,047 A | 4/2000 | Crabtree et al. |
| 6,057,152 A | 5/2000 | Samulski et al. |
| 6,063,625 A | 5/2000 | Crabtree et al. |
| 6,117,680 A | 9/2000 | Natesan et al. |
| 6,127,521 A | 10/2000 | Berlin et al. |
| 6,133,456 A | 10/2000 | Holt et al. |
| 6,140,120 A | 10/2000 | Crabtree et al. |
| 6,150,137 A | 11/2000 | Berlin et al. |
| 6,150,527 A | 11/2000 | Holt et al. |
| 6,165,787 A | 12/2000 | Crabtree et al. |
| 6,187,757 B1 | 2/2001 | Clackson et al. |
| 6,204,059 B1 | 3/2001 | Samulski et al. |
| 6,258,603 B1 | 7/2001 | Carlson et al. |
| 6,258,823 B1 | 7/2001 | Holt et al. |
| 6,268,213 B1 | 7/2001 | Samulski et al. |
| 6,326,166 B1 | 12/2001 | Pomerantz et al. |
| 6,464,374 B2 | 10/2002 | Akiyama et al. |
| 6,464,974 B1 | 10/2002 | Berlin et al. |
| 6,476,200 B1 | 11/2002 | Sabatini et al. |
| 6,479,653 B1 | 11/2002 | Natesan et al. |
| 6,491,907 B1 | 12/2002 | Rabinowitz et al. |
| 6,492,106 B1 | 12/2002 | Sabatini et al. |
| 6,506,379 B1 | 1/2003 | Clackson et al. |

(Continued)

FOREIGN PATENT DOCUMENTS

| | | |
|---|---|---|
| CA | 2906676 A1 | 9/2014 |
| EP | 1310571 | 5/2003 |

(Continued)

OTHER PUBLICATIONS

Response dated Nov. 11, 2019 Second Office action filed on Jul. 9, 2020 in corresponding Eurasian patent application No. 201792500.

(Continued)

*Primary Examiner* — Benjamin P Blumel
(74) *Attorney, Agent, or Firm* — Howson and Howson LLP; Cathy Kodroff

(57) ABSTRACT

AAV vectors expressing anti-influenza antibodies are provided. Also described are pharmaceutical compositions useful in delivery same for prophylactic or anti-viral purposes. Methods of delivering such vectors are provided.

21 Claims, 8 Drawing Sheets

Specification includes a Sequence Listing.

(56) References Cited

U.S. PATENT DOCUMENTS

| | | |
|---|---|---|
| 6,509,152 B1 | 1/2003 | Berlin et al. |
| 6,596,535 B1 | 7/2003 | Carter |
| 6,649,595 B2 | 11/2003 | Clackson et al. |
| 6,660,514 B1 | 12/2003 | Zolotukhin et al. |
| 6,693,189 B2 | 2/2004 | Holt et al. |
| 6,780,639 B1 | 8/2004 | Chtarto et al. |
| 6,951,753 B2 | 10/2005 | Shenk et al. |
| 6,972,193 B1 | 12/2005 | Crabtree et al. |
| 6,984,635 B1 | 1/2006 | Schreiber et al. |
| 7,008,780 B2 | 3/2006 | Pomerantz et al. |
| 7,045,315 B2 | 5/2006 | Evans et al. |
| 7,067,526 B1 | 6/2006 | Yang et al. |
| 7,091,038 B2 | 8/2006 | Palli et al. |
| 7,094,604 B2 | 8/2006 | Snyder et al. |
| 7,109,317 B1 | 9/2006 | Clemons et al. |
| 7,125,717 B2 | 10/2006 | Carter |
| 7,172,893 B2 | 2/2007 | Rabinowitz et al. |
| 7,196,192 B2 | 3/2007 | Yang et al. |
| 7,201,898 B2 | 4/2007 | Monahan et al. |
| 7,229,823 B2 | 6/2007 | Samulski et al. |
| 7,282,199 B2 | 10/2007 | Gao et al. |
| 7,439,065 B2 | 10/2008 | Ferrari et al. |
| 7,442,373 B2 | 10/2008 | Morrow et al. |
| 7,456,683 B2 | 11/2008 | Takano et al. |
| 7,485,441 B2 | 2/2009 | Pomerantz et al. |
| 7,588,772 B2 | 9/2009 | Kay et al. |
| 7,785,888 B2 | 8/2010 | Carter |
| 7,790,449 B2 | 9/2010 | Gao et al. |
| 7,846,729 B2 | 12/2010 | Carter |
| 7,906,111 B2 | 3/2011 | Wilson et al. |
| 8,071,371 B2 | 12/2011 | Lanzavecchia |
| 8,093,054 B2 | 1/2012 | Carter |
| 8,114,402 B2 | 2/2012 | Grandea et al. |
| 8,124,092 B2 | 2/2012 | Lanzavecchia |
| 8,734,809 B2 | 5/2014 | Gao et al. |
| 8,852,595 B2 | 10/2014 | Vogels et al. |
| 8,927,514 B2 | 1/2015 | Chatterjee et al. |
| 9,340,603 B2 | 5/2016 | Lanzavecchia |
| 9,719,106 B2 | 8/2017 | Wilson et al. |
| 10,138,295 B2 | 11/2018 | Wilson et al. |
| 10,385,119 B2 | 8/2019 | Wilson et al. |
| 10,647,998 B2 | 5/2020 | Wilson et al. |
| 10,756,568 B2 | 9/2020 | Limberis et al. |
| 2002/0110861 A1 | 8/2002 | Dhadialla et al. |
| 2002/0173474 A1 | 11/2002 | Schreiber et al. |
| 2004/0033600 A1 | 2/2004 | Palli et al. |
| 2004/0096942 A1 | 5/2004 | Kapitskaya et al. |
| 2005/0266457 A1 | 12/2005 | Palli et al. |
| 2006/0014711 A1 | 1/2006 | Evans et al. |
| 2006/0100416 A1 | 5/2006 | Palli et al. |
| 2006/0136184 A1 | 6/2006 | Gustafsson et al. |
| 2007/0036760 A1 | 2/2007 | Wilson et al. |
| 2007/0161086 A1 | 7/2007 | Palli et al. |
| 2009/0100535 A1 | 4/2009 | Pomerantz et al. |
| 2009/0104232 A1 | 4/2009 | Crystal et al. |
| 2009/0197338 A1 | 8/2009 | Vandenberghe et al. |
| 2009/0275107 A1 | 11/2009 | Lock et al. |
| 2010/0080813 A1 | 4/2010 | Lanzavecchia |
| 2011/0076265 A1 | 3/2011 | Burioni et al. |
| 2011/0150904 A1 | 6/2011 | Schiltz et al. |
| 2011/0236353 A1 | 9/2011 | Wilson et al. |
| 2011/0274702 A1 | 11/2011 | Lanzavecchia |
| 2012/0232133 A1 | 9/2012 | Balazs et al. |
| 2012/0282695 A1 | 11/2012 | Blain et al. |
| 2013/0045186 A1 | 2/2013 | Gao et al. |
| 2013/0243792 A1 | 9/2013 | Vogels et al. |
| 2014/0031418 A1 | 1/2014 | Wilson et al. |
| 2014/0032186 A1 | 1/2014 | Gustafsson et al. |
| 2014/0037637 A1 | 2/2014 | McNally et al. |
| 2014/0065666 A1 | 3/2014 | Simpson et al. |
| 2014/0094392 A1 | 4/2014 | Bowers et al. |
| 2014/0127749 A1 | 5/2014 | Mason et al. |
| 2015/0344911 A1 | 12/2015 | Chatterjee et al. |
| 2017/0028082 A1 | 2/2017 | Wilson et al. |
| 2017/0043035 A1 | 2/2017 | Wilson et al. |
| 2017/0081392 A1 | 3/2017 | Wilson et al. |
| 2017/0101458 A1 | 4/2017 | Wilson et al. |
| 2017/0159027 A1 | 6/2017 | Wilson et al. |
| 2017/0292132 A1 | 10/2017 | Wilson et al. |
| 2018/0155412 A1 | 6/2018 | Limberis et al. |
| 2018/0243416 A1 | 8/2018 | Limberis et al. |
| 2019/0216841 A1 | 7/2019 | Wilson et al. |
| 2020/0216520 A1 | 7/2020 | Wilson et al. |

FOREIGN PATENT DOCUMENTS

| | | |
|---|---|---|
| EP | 2296700 | 3/2011 |
| WO | WO-94/18347 | 8/1994 |
| WO | WO-95/33052 | 12/1995 |
| WO | WO-96/06097 | 2/1996 |
| WO | WO-1996/009378 | 3/1996 |
| WO | WO-96/20951 | 7/1996 |
| WO | WO-96/41865 | 12/1996 |
| WO | WO-97/31898 | 9/1997 |
| WO | WO-98/02441 | 1/1998 |
| WO | WO-99/10508 | 3/1999 |
| WO | WO-99/10510 | 3/1999 |
| WO | WO-99/36553 | 7/1999 |
| WO | WO-99/41258 | 8/1999 |
| WO | WO-2001/014387 | 3/2001 |
| WO | WO-2001/070816 | 9/2001 |
| WO | WO-2002/029075 | 4/2002 |
| WO | WO-2002/066612 | 8/2002 |
| WO | WO-2002/066613 | 8/2002 |
| WO | WO-2002/066614 | 8/2002 |
| WO | WO-2002/066615 | 8/2002 |
| WO | WO-2003/042397 | 5/2003 |
| WO | WO-2005/033321 | 4/2005 |
| WO | WO-2005/108617 | 11/2005 |
| WO | WO-2006/110689 | 10/2006 |
| WO | WO-2008/156763 | 12/2008 |
| WO | WO-2009/079259 A2 | 6/2009 |
| WO | WO-2009/115972 | 9/2009 |
| WO | WO-2010/010466 | 1/2010 |
| WO | WO-2010/013036 | 2/2010 |
| WO | WO-2010/044921 A2 | 4/2010 |
| WO | WO-2010/130636 | 11/2010 |
| WO | WO-2010/140114 | 12/2010 |
| WO | WO-2010/151673 | 12/2010 |
| WO | WO-2011/084996 | 7/2011 |
| WO | WO-2011/126868 | 10/2011 |
| WO | WO-2012/145572 | 10/2012 |
| WO | WO-2013/007770 | 1/2013 |
| WO | WO-2013/049492 | 4/2013 |
| WO | WO-2013/114885 | 8/2013 |
| WO | WO-2013/132007 | 9/2013 |
| WO | WO-2013/155222 | 10/2013 |
| WO | WO-2013/155522 | 10/2013 |
| WO | WO2014/152841 A1 | 9/2014 |
| WO | WO-2015/012924 | 1/2015 |
| WO | WO-2015/127136 | 8/2015 |
| WO | WO-2015/175639 | 11/2015 |
| WO | WO-2016/049230 | 3/2016 |
| WO | WO-2016/054598 | 4/2016 |
| WO | WO-2016/124768 | 8/2016 |
| WO | WO-2016/200543 | 12/2016 |
| WO | WO-2017/040528 | 3/2017 |
| WO | WO-2017/100674 | 6/2017 |
| WO | WO-2017/100676 | 6/2017 |
| WO | WO-2017/100704 | 6/2017 |
| WO | WO-2017/106244 | 6/2017 |
| WO | WO-2017/106326 | 6/2017 |
| WO | WO-2017/1603 60 | 9/2017 |
| WO | WO-2018/057916 | 3/2018 |

OTHER PUBLICATIONS

Communication Pursuant to Article 94(3) EPC issued in corresponding European Patent Application No. 16775005.8, dated Feb. 27, 2020.

Response dated Feb. 27, 2020 Communication Pursuant to Article 94(3) EPC filed on Sep. 7, 2020 in corresponding European Patent Application No. 16775005.8.

(56) References Cited

OTHER PUBLICATIONS

Maria P. Limberis, Anna P. Tretiakova, James M. Wilson, Michael Naso, Joost Kolkman, Robert Friesen, and Qiang Wang. U.S. Appl. No. 16/935,121, filed Jul. 21, 2020, which is a continuation of U.S. Appl. No. 15/906,887, now U.S. Pat. No. 10,756,568 B2.
Communication Pursuant to Article 94(3) EPC issued in a European Patent Application No. 18710971.5, dated Sep. 25, 2020.
First Office Action dated Jan. 20, 2020 in Pakistani Patent Application No. 117/2018.
"Types of Influenza Viruses" Web page <https://www.cdc.gov/flu/about/viruses/types.htm>, 2 pages, Apr. 4, 2016, page last updated Aug. 19, 2014, retrieved from Internet Archive Wayback Machine <https://web.archive.org/web/20160404144120/https://www.cdc.gov/flu/about/viruses/types.htm> on May 11, 2018.
Adam et al. Adeno-associated virus 9-mediated airway expression of antibody protects old and immunodeficient mice against influenza virus. Clin Vaccine Immunol. Nov. 2014;21(11):1528-33, doi: 10.1128/CVI.00572-14. Epub Sep. 10, 2014.
Alexander et al., Insulin stimulates glyceraldehyde-3-phosphate dehydrogenase gene expression through cis-acting DNA sequences. Proc Natl Acad Sci U S A. Jul. 1988;85(14):5092-6.
Amara et al, "A versatile synthetic dimerizer for the regulation of protein-protein interactions", Proc. Natl. Acad. Sci. USA, vol. 94(20) pp. 10618-10623 (Sep. 1997).
An et al, Active retrotransposition by a synthetic L1 element in mice. Proc Natl Acad Sci U S A. Dec. 5, 2006;103(49):18662-7. Epub Nov. 21, 2006.
Andersson et al, An atlas of active enhancers across human cell types and tissues. Nature. Mar. 27, 2014;507(7493):455-461. doi: 10.1038/nature12787. (Published: Mar. 26, 2014).
Aquino et al., Influenza Outbreak in a Vaccinated Population—USS Ardent, Feb. 2014. MMWR Morb Mortal Wkly Rep. Oct. 24, 2014;63(42):947-9. Published online Oct. 24, 2014.
Ashkenazi et al. "Immunoadhesins." International reviews of immunology 10.2-3 (1993): 219-227. (1993).
Balazs et al. Antibody-based protection against HIV infection by vectored immunoprophylaxis. Nature. Nov. 30, 2011;481(7379):81-4. doi: 10.1038/nature10660. Published online Nov. 30, 2011.
Ballay et al. In vitro and in vivo synthesis of the hepatitis B virus surface antigen and of the receptor for polymerized human serum albumin from recombinant human adenoviruses. EMBO J. Dec. 30, 1985;4(13B):3861-5. (Dec. 30, 1985).
Bell et al, "The AAV9 receptor and its modification to improve in vivo lung gene transfer in mice", J Clin. Invest., vol. 121(6) pp. 2427-2435 (Jun. 2011).
Berezov et al, "Disabling erbB receptors with rationally designed exocyclic mimetics of antibodies: structure-function analysis", J. Med. Chem., vol. 44(16) pp. 2565-2574 (Aug. 2001).
Bouvier et al. "The biology of influenza viruses." Vaccine 26 (2008): D49-D53 (Sep. 2008).
Boyer et al, "Persistent expression of single chain antibodies mediated by AAV5 and AAVrh.10 vectors", vol. 11, sup. 1, abstract 853, pp. S331-S332 (May 2005).
Brinster et al., "Regulation of metallothionein-thymidine kinase fusion plasmids injected into mouse eggs", Nature, vol. 296(5852) pp. 39-42 (Mar. 1982).
Buning et al, "Recent developments in adeno-associated virus vector technology", J. Gene Med., vol. 10(7) pp. 717-733 (Jul. 2008).
Calcedo et al., Worldwide epidemiology of neutralizing antibodies to adeno-associated viruses. J Infect Dis. Feb. 1, 2009;199(3):381-90. doi: 10.1086/595830.
Chamow et al. "Immunoadhesins: principles and applications." Trends in biotechnology 14.2 (1996): 52-60. (Feb. 1996).
Corti et al, A neutralizing antibody selected from plasma cells that binds to group 1 and group 2 influenza A hemagglutinins. Science. Aug. 12, 2011;333(6044):850-6. doi: 10.1126/science.1205669. Epub Jul. 28, 2011.
Crosariol et al. 699. Effective AAV9 Vector Delivery to Nasal Mucosa for Protection Against Airborne Challenge with Influenza A and B. Immunological Aspects of Gene Therapy II: AAV Vectors, Molecular Therapy, vol. 24, Supplement 1, p. S276, May 2016, DOI: https://doi.org/10.1016/S1525-0016(16)33507-9.
Davidson et al. Mechanism of Binding to Ebola Virus Glycoprotein by the ZMapp, ZMAb, and MB-003 Cocktail Antibodies. J Virol. Nov. 2015;89(21):10982-92. doi: 10.1128/JVI.01490-15. Epub Aug. 26, 2015.
Dawood et al., Estimated global mortality associated with the first 12 months of 2009 pandemic influenza A H1N1 virus circulation: a modelling study. Lancet Infect Dis. Sep. 2012;12(9):687-95. doi: 10.1016/S1473-3099(12)70121-4. Epub Jun. 26, 2012.
De et al, "Rapid/ Sustained Anti-anthrax Passive Immunity Mediated by co-administration od Ad/AAV", Molecular Therapy, vol. 6(1) pp. 203-209 (Jan. 2008).
De et al, "High levels of persistent expression of alpha 1—antitrypsin mediated by the nonhuman primate serotype rh.10 adeno-associated virus despite preexisting immunity to common human adeno-associated viruses", Mol. Ther., vol. 13(1) pp. 67-76 (Jan. 2006).
De et al, "Induction of Persistent Passive Immunity Against Anthrax Toxin by an Adeno-Associated Virus Type rh10 Vector Expressing Anti-Protective Antigene Antibody", Molecular Therapy, vol. 13, supp1, Abstract 611, pp. S236 (May 2006).
Deuschle et al, "Tetracycline-reversible silencing of eukaryotic promoters", Mol. Cell Biol., vol. 15(4), pp. 1907-1914 (Apr. 1995).
Djupesland, Nasal drug delivery devices: characteristics and performance in a clinical perspective—a review. Drug Deliv Transl Res. Feb. 2013;3(1):42-62. doi: 10.1007/s13346-012-0108-9. Epub Oct. 18, 2012.
Donnelly et al, "The cleavage activities of aphthovirus and cardiovirus 2A proteins", J. Gen. Virol., vol. 78(Pt 1) pp. 13-21 (Jan. 1997).
Dreyfus et al., Highly conserved protective epitopes on influenza B viruses. Science. Sep. 14, 2012;337(6100):1343-8. doi: 10.1126/science.1222908. Epub Aug. 9, 2012.
Du et al, "Intranasal vaccination of recombinant adeno-associated virus encoding receptor-binding domain of severe acute respiratory syndrome coronavirus (SARS-CoV) spike protein induces strong mucosal immune responses and provides long-term protection against SARS-CoV infection", J Immunology, vol. 180(2) pp. 948-956 (Jan. 2008).
Ekiert et al, "Antibody recognition of a highly conserved influenza virus epitope", Science, vol. 324(5924) pp. 246-251 (Apr. 2009).
Ercolani et al., Isolation and complete sequence of a functional human glyceraldehyde-3-phosphate dehydrogenase gene. J Biol Chem. Oct. 25, 1988;263(30):15335-41.
Estimates of deaths associated with seasonal influenza: United States, 1976-2007. 2010; Available from: MMWR Morb. Mortal. Wkly. Rep. 59:1057-1062 Page last updated: Aug. 27, 2010.
Fang et al, "An antibody delivery system for regulated expression of therapeutic levels of monoclonal antibodies in vivo", Mol. Ther., vol. 15(6) pp. 1153-1159 (Mar. 2007).
Flotte et al. Stable in vivo expression of the cystic fibrosis transmembrane conductance regulator with an adeno-associated virus vector. Proc Natl Acad Sci U S A. Nov. 15, 1993;90(22):10613-7. (Published online Nov. 15, 1993.).
Furler et al, "Recombinant AAV vectors containing the foot and mouth disease virus 2A sequence confer efficient bicistronic gene expression in cultured cells and rat substantia nigra neurons", Gene Ther., vol. 8(11) pp. 864-873 (Jun. 2001).
Gamblin et al. "Influenza hemagglutinin and neuraminidase membrane glycoproteins." Journal of Biological Chemistry 285.37 (2010): 28403-28409 (Epub Jun. 10, 2010).
Gao et al, Adeno-associated viruses undergo substantial evolution in primates during natural infections. Proc. Natl. Acad. Sci. U.S.A. 100 (10), 6081-6086 (2003).
Gao et al, Clades of Adeno-associated viruses are widely disseminated in human tissues. J Virol. Jun. 2004;78(12):6381-8.
Glezen et al., The burden of influenza B: a structured literature review. Am J Public Health. Mar. 2013;103(3):e43-51. doi: 10.2105/AJPH.2012.301137. Epub Jan. 17, 2013.
Gossen et al, "Tight control of gene expression in mammalian cells by tetracycline-responsive promoters", Proc. Natl. Acad. Sci. USA, vol. 89(12) pp. 5547-5551 (Jun. 1992).

(56) References Cited

OTHER PUBLICATIONS

Gossen et al, "Transcriptional activation by tetracyclines in mammalian cells" Science, vol. 268(5218) pp. 1766-1769 (Jun. 1995).
Grieger et al. "Adeno-associated virus as a gene therapy vector: Vector development, production and clinical applications," Adv. Biochem. Engin/Biotechnol. 99: 119-145 (Oct. 2005).
Grimm et al., Titration of AAV-2 particles via a novel capsid ELISA: packaging of genomes can limit production of recombinant AAV-2. Gene Therapy (Jul. 1999) 6 (7):1322-1330 (Published: Jul. 2, 1999).
Hoogenboom et al, "By-passing immunisation. Human antibodies from synthetic repertoires of germline VH gene segments rearranged in vitro", J. Mil. Biol., vol. 227(2) pp. 381-388 (Sep. 1992).
Hynes et al, "Hormone-responsive expression of an endogenous proviral gene of mouse mammary tumor virus after molecular cloning and gene transfer into cultured cells", Proc. Natl. Acad. Sci. USA, vol. 78(4) pp. 2038-2042 (Apr. 1981).
Israel et al, "Highly inducible expression from vectors containing multiple GRE's in CHO cells overexpressing the glucocorticoid receptor", Nucl. Acids, Res., vol. 17(12) pp. 4589-4604 (Jun. 1989).
Johnson et al. Vector-mediated gene transfer engenders long-lived neutralizing activity and protection against SIV infection in monkeys. Nat Med. Aug. 2009;15(8):901-6. doi: 10.1038/nm.1967. Epub May 17, 2009.
Jones et al, "Replacing the complementarity-determining regions in a human antibody with those from a mouse" Nature, vol. 321(6069) pp. 522-525 (May 1986).
Juno et al., Immunogenetic Factors Associated with Severe Respiratory Illness Caused by Zoonotic H1N1 and H5N1 Influenza Viruses. Clinical and Developmental Immunology. vol. 2012, Article ID 797180, 9 pages.
Kaplitt MG, et al. Long-term gene expression and phenotypic correction using adeno-associated virus vectors in the mammalian brain. Nat Genet. Oct. 1994;8(2):148-54. (Oct. 1, 1994).
Klock et al, "Oestrogen and glucocorticoid responsive elements are closely related but distinct", Nature, vol. 329(6141) pp. 734-736 (Oct. 1987).
Klump et al, "Retroviral vector-mediated expression of HoxB4 in hematopoietic cells using a novel coexpression strategy", Gene Ther., vol. 8(10) pp. 811-817 (May 2001).
Kohler et al, "Continuous cultures of fused cells secreting antibody of predefined specificity", Nature, vol. 256(5517) pp. 495-497 (Aug. 1975).
Kort et al, "Recombinant anti-sialidase single-chain variable fragment antibody. Characterization, formation of dimer and higher-molecular-mass multimers and the solution of the crystal structure of the single-chain variable fragment/sialidase complex", Eur. J. Biochem., vol. 221(1) pp. 151-157 (Apr. 1994).
Lai et al., "Antisense RNA complementary to 3' coding and noncoding sequences of creatine kinase is a potent inhibitor of translation in vivo", Proc. Natl. Acad. Sci. USA, vol. 86(24) pp. 10006-10010 ( Dec. 1989).
Lee et al, "Glucocorticoids regulate expression of dihydrofolate reductase cDNA in mouse mammary tumour virus chimaeric plasmids", Nature, vol. 294(5838) pp. 228-232 (Nov. 1981).
Levitt et al, Definition of an efficient synthetic poly(A) site. Genes Dev., Jul. 1989, 3(7):1019-25.
Limberis et al, "Adeno-associated virus serotype 9 vectors transduce murine alveolar and nasal epithelia and can be readministered" Proc. Natl. Acad. Sci. USA, vol. 103(35) pp. 12993-12998 (Aug. 2006).
Limberis et al, "Establishment of a New AAV Clinical Candidate for Prophylaxis Against Influenza A and B", Poster presented at American Society of Gene & Cell Therapy 2017 Annual Meeting On May 11, 2017.
Limberis et al, "Intranasal antibody gene transfer in mice and ferrets elicits broad protection against pandemic influenza", Sci. Transl. Med., vol. 5(187) pp. 1-8 (May 2013).

Limberis et al. Adeno-Associated Virus Serotype 9-Expressed ZMapp in Mice Confers Protection Against Systemic and Airway-Acquired Ebola Virus Infection. J Infect Dis. Dec. 15, 2016;214(12):1975-1979. Epub Sep. 28, 2016.
Limberis et al. Vectored expression of the broadly neutralizing antibody FI6 in mouse airway provides partial protection against a new avian influenza A virus, H7N9. Clin Vaccine Immunol. Dec. 2013;20(12):1836-7. doi: 10.1128/CVI.00545-13. Epub Oct. 16, 2013.
Limberis. AAV Vectors for Rapid and Effective Prophylaxis against Airborne Viruses. PowerPoint presented on Feb. 14, 2018 at 2018 ASM Biothreats meeting in Baltimore, Maryland, pp. 1-34. (Feb. 2018).
Ljungman, Vaccination of immunocompromised patients. Clin Microbiol Infect. Oct. 2012;18 Suppl 5:93-9. doi: 10.1111/j.1469-0691.2012.03971.x.
Lock et al, Rapid, simple, and versatile manufacturing of recombinant adeno-associated viral vectors at scale. Hum Gene Ther. Oct. 2010;21(10):1259-71. doi: 10.1089/hum.2010.055. (Published online Sep. 24, 2010).
Locket al, Absolute determination of single-stranded and self-complementary adeno-associated viral vector genome titers by droplet digital PCR. Hum Gene Ther Methods. Apr. 2014;25(2):115-25. doi: 10.1089/hgtb.2013.131. (Published online Dec. 12, 2013).
Marks et al, "By-passing immunization. Human antibodies from V-gene libraries displayed on phage", J. Mol. Biol., vol. 222(3) pp. 381-597 (Dec. 1991).
Mayo et al, "The mouse metallothionein-I gene is transcriptionally regulated by cadmium following transfection into human or mouse cells" Cell, vol. 29(1) pp. 99-108 (May 1982).
McBride et al. Phase 2 Randomized Trial of the Safety and Efficacy of MHAA4549A, a Broadly Neutralizing Monoclonal Antibody, in a Human Influenza A Virus Challenge Model. Antimicrob Agents Chemother. Oct. 24, 2017;61(11). pii: e01154-17. Accepted manuscript posted online Aug. 14, 2017.
McCarty et al, Self-complementary recombinant adeno-associated virus (scAAV) vectors promote efficient transduction independently of DNA synthesis. Gene Therapy, (Aug. 2001), vol. 8, No. 16, pp. 1248-1254 (Aug. 13, 2001).
McLellan et al. Structure of respiratory syncytial virus fusion glycoprotein in the postfusion conformation reveals preservation of neutralizing epitopes. J Virol. Aug. 2011;85(15):7788-96. doi: 10.1128/JVI.00555-11. Epub May 25, 2011.
Medina, Influenza A viruses: new research developments. Nat Rev Microbiol. Jul. 11, 2011;9(8):590-603. doi: 10.1038/nrmicro2613. (Published: Jul. 11, 2011).
Melnick JL, et al. Association of 20-Millimicron Particles with Adenoviruses. J Bacteriol. Jul. 1965;90(1):271-4. (Jul. 1965).
Merrifield, Solid Phase Peptide Synthesis I. The Synthesis of a Tetrapepide. J. Am. Chem. Soc., vol. 85, pp. 2149 (Jan. 1963).
Miller et al. Expression of a retrovirus encoding human HPRT in mice. Science. Aug. 10, 1984;225(4662):630-2. (Aug. 10, 1984).
Molinari et al., The annual impact of seasonal influenza in the US: measuring disease burden and costs. Vaccine. Jun. 28, 2007;25(27):5086-96. Epub Apr. 20, 2007.
Nakamura et al, An in vivo human-plasmablast enrichment technique allows rapid identification of therapeutic influenza A antibodies. Cell Host Microbe. Jul. 17, 2013;14(1):93-103.
Ng et al., Regulation of the human beta-actin promoter by upstream and intron domains. Nuc. Nucleic Acids Res. Jan. 25, 1989; 17(2): 601-615.
Nieto et al, Combined prophylactic and therapeutic intranasal vaccination against human papillomavirus type-16 using different adeno-associated virus serotype vectors. Antiviral Ther., vol. 14(8) pp. 1125-1137 (2009).
Oliveira et al., Influenza in the intensive care unit. J Intensive Care Med. Mar.-Apr. 2003;18(2):80-91. (First Published Mar. 1, 2003 ).
Quitschke et al., The beta actin promoter. High levels of transcription depend upon a CCAAT binding factor. Jun. 5, 1989;264(16):9539-46.
Radcliffe et al., Multiple gene products from a single vector: 'self-cleaving' 2A peptides. Gene Therapy (2004), 11(23), 1673-1674 (Published Oct. 26, 2004).

(56) References Cited

OTHER PUBLICATIONS

Riechmann et al, Reshaping human antibodies for therapy. Nature, vol. 332(6162) pp. 323-327 (Mar. 1988).
Roscilli et al, Long-term and tight control of gene expression in mouse skeletal muscle by a new hybrid human transcription factor. Mol. Ther., vol. 6 (5) pp. 653-663 (Nov. 2002).
Sawada-Hirai et al, Human anti-anthrax protective antigen neutralizing monoclonal antibodies derived from donors vaccinated with anthrax vaccine adsorbed. J. Immune Based Ther. Vaccines, vol. 2(1) pp. 5 (May 2004).
Scharfmann et al, Long-term in vivo expression of retrovirus-mediated gene transfer in mouse fibroblast implants. Proc. Natl. Acad. Sci. USA, vol. 88 (11) pp. 4626-4630 (Jun. 1991).
Schillinger et al, Regulatable atrial natriuretic peptide gene therapy for hypertension, Proc. Natl. Acad. Sci. USA, vol. 102(39) pp. 13789-13794 (Sep. 2005).
Searel et al, Building a metal-responsive promoter with synthetic regulatory elements, Mol. Cell. Biol., vol. 5(6) pp. 1480-1489 (Jun. 1985).
Shapiro et al., The potential American market for generic biological treatments and the associated cost savings. Feb. 2008; Available from: http://www.sonecon.com/docs/studies/0208_GenericBiologicsStudy.pdf.
Shapshak et al., The Influenza Pandemic of 2009: Lessons and Implications. Mol Diagn Ther. Apr. 1, 2011;15(2):63-81.
Skaricic et al, Genetic delivery of an anti-RSV antibody to protect against pulmonary infection with RSV. Virology, vol. 378(1) pp. 79-85 (Jun. 2008).
Sommer et al., Quantification of adeno-associated virus particles and empty capsids by optical density measurement. Mol Ther. Jan. 2003;7(1):122-8.
Stratford-Perricaudet LD et al. Evaluation of the transfer and expression in mice of an enzyme-encoding gene using a human adenovirus vector. Hum Gene Ther. 1990 Fall;1(3):241-56.
Sui et al, "Structural and functional bases for broad-spectrum neutralization of avian and human influenza A viruses", Nat. Struct. Mol. Boil., vol. 16(3) pp. 265-273 (Mar. 2009).
Thomson JD et al, A comprehensive comparison of multiple sequence alignments. Nucl. Acids. Res., 27(13):2682-2690 (Jul. 1999).
Tycko et al. 701. Intranasal Delivery of Neutralizing Antibodies by AAV9 to Protect Mice Against RSV Infection. Vaccines and Immunotherapy, Molecular Therapy, vol. 22, Supplement 1, p. S271, May 2014.
Uttrutia, KRAB-containing zinc-finger repressor proteins. Genome Biology, vol. 4(10) pp. 231 (Sep. 2003).
Verhoeyen et al, "Reshaping human antibodies: grafting an antilysozyme activity", Science, vol. 239(4847) pp. 1534-1536 (Mar. 1988).
Wang et al, A regulatory system for use in gene transfer. Proc. Natl. Acad. Sci. USA, vol. 91(17) pp. 8180-8184 (Aug. 1994).
WHO Manual on Animal Influenza Diagnosis and Surveillance, Geneva: World Health Organisation, 2002, version 2002.5.
Willey et al. "Neutralizing antibody titers conferring protection to macaques from a simian/human immunodeficiency virus challenge using the TZM-bl assay." AIDS research and human retroviruses 26.1 (2010): 89-98 (Jan. 10, 2010).
Williams DA, et al. Introduction of new genetic material into pluripotent haematopoietic stem cells of the mouse. Nature. Aug. 9-15, 1984;310(5977):476-80. (Aug. 9, 1984).
Wobus et al., Monoclonal antibodies against the adeno-associated virus type 2 (AAV-2) capsid: epitope mapping and identification of capsid domains involved in AAV-2-cell interaction and neutralization of AAV-2 infection. J. Virol. (2000) 74:9281-9293 (Oct. 2000).
Xia et al., siRNA-mediated gene silencing in vitro and in vivo. Nat Biotechnol. Oct. 2002; 20(10):1006-10. Epub Sep. 16, 2002.
Xin et al., A novel recombinant adeno-associated virus vaccine induces a long-term humoral immune response to human immunodeficiency virus, Hum Gene Ther. Jun. 10, 2001;12(9):1047-61. (Jun. 10, 2001).
Zhang et al., Adenovirus-adeno-associated virus hybrid for large-scale recombinant adeno-associated virus production,. Hum Gene Ther. Sep. 2009;20(9):922-9. doi: 10.1089/hum.2009.125. (Published Online:Aug. 6, 2009).
Zhang et al., Alteration in the IL-2 signal peptide affects secretion of proteins in vitro and in vivo. J Gene Med. Mar. 2005;7(3):354-65. (First published: Dec. 23, 2004).
Limberis et al, U.S. Appl. No. 15/906,887, filed Feb. 27, 2018.
International Preliminary Report on Patentability, dated Nov. 14, 2017 in International Patent Application No. PCT/US2016/032063.
International Search Report and and Written Opinion dated Dec. 19, 2016 in International Patent Application No. PCT/US2016/032063.
International Preliminary Report on Patentability, dated Oct. 22, 2013 in International Patent Application No. PCT/US2012/034355.
International Search Report and Written Opinion dated Sep. 14, 2012 in International Patent Application No. PCT/US2012/034355.
International Preliminary Report on Patentability, dated Nov. 15, 2016 in International Patent Application No. PCT/US2015/030533.
International Search Report and Written Opinion dated Aug. 14, 2015 in International Patent Application No. PCT/US2015/030533.
International Search Report and Written Opinion dated Jan. 8, 2018 in International Patent Application No. PCT/US2017/052991.
Response to Communication Pursuant to Rules 161(1) and 162 EPC filed for European Patent Application No. 12719540.2, dated Jun. 9, 2014.
Communication Pursuant to Article 94(3) EPC issued on European Patent Application No. 12719540.2, dated Jun. 10, 2016.
Response to Communication Pursuant to Article 94(3) EPC dated Jun. 10, 2016, filed on Dec. 19, 2016 in European Patent Application No. 12719540.2.
Communication Pursuant to Article 94(3) EPC issued on European Patent Application No. 12719540.2, dated Aug. 2, 2017.
Response to Communication Pursuant to Article 94(3) EPC dated Aug. 2, 2017, filed on Dec. 12, 2017 in European Patent Application No. 12719540.2.
Restriction Requirement dated Feb. 26, 2016 in U.S. Appl. No. 14/112,802.
Response to the Restriction Requirement dated Feb. 26, 2016 in U.S. Appl. No. 14/112,802, filed Aug. 19, 2016.
Non-final Rejection dated Sep. 9, 2016 U.S. Appl. No. 14/112,802.
Response to the non-final Rejection dated Sep. 9, 2016 issued in U.S. Appl. No. 14/112,802, filed Mar. 8, 2017.
Supplemental Response to the non-final Rejection dated Sep. 9, 2016 issued in U.S. Appl. No. 14/112,802, filed Mar. 9, 2017.
Final Rejection dated Jun. 21, 2017 in U.S. Appl. No. 14/112,802.
Response to the Final Rejection dated Jun. 21, 2017 in U.S. Appl. No. 14/112,802, filed Sep. 20, 2017.
Non-final Rejection dated Dec. 29, 2017 in U.S. Appl. No. 14/112,802.
GenBank: AEL31310.1, Web page <https://www.ncbi.nlm.nih.gov/protein/AEL31310.1>, 2 pages, retrieved from Internet on May 11, 2018.
NCBI Reference Sequence: NC_001401.2, Web page <https://www.ncbi.nlm.nih.gov/nuccore/NC_001401>, 5 pages, retrieved from Internet on May 11, 2018.
GenBank: K03104.1, Web page <https://www.ncbi.nlm.nih.gov/nuccore/K03104.1>, 1 page, retrieved from Internet on May 11, 2018.
GenBank: X00182.1, Web page <https://www.ncbi.nlm.nih.gov/nuccore/X00182.1>, 3 pages, retrieved from Internet on May 11, 2018.
NCBI Reference Sequence: NM_002467.5, Web page <https://www.ncbi.nlm.nih.gov/nuccore/NM_002467>, 4 pages, retrieved from Internet on May 11, 2018.
UniProtKB—P60568 (IL2_HUMAN), Web page <http://www.uniprot.org/uniprot/P60568>, 9 pages, retrieved from Internet on May 11, 2018.
GenBank: AEL31303.1, Web page <https://www.ncbi.nlm.nih.gov/protein/AEL31303.1>, 2 pages, retrieved from Internet on May 11, 2018.
GenBank: BAF64540.1, Web page <https://www.ncbi.nlm.nih.gov/protein/BAF64540.1>, 2 pages, retrieved from Internet on May 11, 2018.

(56) References Cited

OTHER PUBLICATIONS

GenBank: ACJ71709.1, Web page <https://www.ncbi.nlm.nih.gov/protein/ACJ71709.1>, 2 pages, retrieved from Internet on May 11, 2018.
GenBank: AGH70219.1, Web page <https://www.ncbi.nlm.nih.gov/protein/AGH70219.1>, 1 page, retrieved from Internet on May 11, 2018.
GenBank: V00882.1, Web page <https://www.ncbi.nlm.nih.gov/protein/AGH70219.1>, 2 pages, retrieved from Internet on May 11, 2018.
GenBank: CAA24362.1, Web page <https://www.ncbi.nlm.nih.gov/protein/AGH70219.1>, 1 page, retrieved from Internet on May 11, 2018.
GenBank: AAS99264.1, Web page <https://www.ncbi.nlm.nih.gov/protein/AAS99264>, 1 page, retrieved from Internet on May 11, 2018.
GenBank: AFP87542.1, Web page <https://www.ncbi.nlm.nih.gov/protein/AFP87542.1>, 2 pages, retrieved from Internet on May 11, 2018.
GenBank: AAB86861.1, Web page <https://www.ncbi.nlm.nih.gov/protein/AAB86861.1>, 1 page, retrieved from Internet on May 11, 2018.
PDB: 2J6E_A, Web page <https://www.ncbi.nlm.nih.gov/protein/2J6E_A>, 2 pages, retrieved from Internet on May 11, 2018.
PDB: 4FQL_H, Web page <https://www.ncbi.nlm.nih.gov/protein/4FQL_H>, 3 pages, retrieved from Internet on May 11, 2018.
Limberis, U.S. Appl. No. 15/906,887, filed Feb. 27, 2018.
Foster et al. Codon and mRNA sequence optimization of microdystrophin transgenes improves expression and physiological outcome in dystrophic mdx mice following AAV2/8 gene transfer. Mol Ther 2008; 16: 1825-32 and Supplementary Material, Figure S1 and S2. Epub Sep. 2, 2008.
Laube, The expanding role of aerosols in systemic drug delivery, gene therapy and vaccination: an update. Transl Respir Med. Jan. 13, 2014;2:3. doi: 10.1186/2213-0802-2-3. eCollection 2014. (Jan. 13, 2014).
First Office Action dated Apr. 16, 2019 in the corresponding Eurasian patent application No. 201792500 with an unofficial translation prepared by the Eurasian agent.
Second Office Action dated Nov. 11, 2019 in the corresponding Eurasian patent application No. 201792500 with an unofficial translation prepared by the Eurasian agent.
Response to the Non-Final Rejection dated Dec. 29, 2017 in U.S. Appl. No. 14/112,802, filed May 29, 2018.
Final Rejection dated Sep. 20, 2018 in U.S. Appl. No. 14/112,802.
Summons to attend oral proceeding pursuant to Rule 115(1) EPC issued on European Patent Application No. 12719540.2, date Feb. 26, 2019.
Response to the Feb. 26, 2019 Summons filed on Oct. 11, 2019 in European Patent Application No. 12719540.2.
Requirement for Restriction/Election issued in parent U.S. Appl. No. 15/906,887, dated Jun. 28, 2019.
Response dated Jun. 28, 2019 Requirement for Restriction/Election issued in parent U.S. Appl. No. 15/906,887, filed Oct. 21, 2019.
Non-final Office Action issued in parent U.S. Appl. No. 15/906,887, dated Oct. 18, 2013.
First Examination Report dated Sep. 8, 2019 in patent application No. GC 2018-34843 filed in Gulf Cooperation Council (GCC).
Afonine PV et al., Towards automated crystallographic structure refinement with phenix.refine, Acta Crystallogr. D Biol. Crystallogr., 68(Pt 4):352-67, Apr. 2012. (Epub Mar. 16, 2012).
Ali MY, Histology of the Human Nasopharyngeal Mucosa, J. Anat., 99(3):657-672, 1965.
Almond B. and Schenborn ET, A Comparison of pCI-neo Vector and pcDNA4/HisMax Vector, Promega Corporation Website, Updated 2000, Available from: http://www.promega.com/resources/pubhub/enotes/a-comparison-of-pcineo-vector-and-pcdna4hismax-vector/.
Balazs AB et al., Broad protection against influenza infection by vectored immunoprophylaxis in mice, Nat. Biotechnol., 31(7):647-52, Jul. 2013. (Epub Jun. 2, 2013).
Beyer WE et al., Cochrane re-arranged: support for policies to vaccinate elderly people against influenza,Vaccine, 31(50):6030-3, Dec. 2013. (Epub Oct. 3, 2013).
Brandenburg B et al., Mechanisms of hemagglutinin targeted influenza virus neutralization, PLoS One, 8(12):e80034, Dec. 11, 2013.
Carragher B et al., Leginon: an automated system for acquisition of images from vitreous ice specimens, J. Struct. Biol., 132(1):33-45, Oct. 2000.
Carter BJ, Chapter 10: The Growth Cycle of Adeno-associated Virus, in CRC Handbook of Parvoviruses, ed. P. Tijsser, CRC Press, p. 155-168, 1990.
Chen H et al., Avian flu: H5N1 virus outbreak in migratory waterfowl. Nature, 436(7048):191-2, Jul. 14, 2005.
Ch'ng JL et al., Antisense RNA complementary to 3' coding and noncoding sequences of creatine kinase is a potent inhibitor of translation in vivo, Proc. Natl. Acad. Sci. USA, 86(24):10006-10, Dec. 1989.
Cox F et al., Protection against H5N1 influenza virus induced by matrix-M adjuvanted seasonal virosomal vaccine in mice requires both antibodies and T cells, PLoS One, 10(12):e0145243, Dec. 22, 2015.
Dhuria et al. Intranasal delivery to the central nervous system: mechanisms and experimental considerations. J Pharm Sci. Apr. 2010;99(4):1654-73. doi: 10.1002/jps.21924. (Epub Oct. 29, 2009).
Dilillo DJ et al., Broadly neutralizing anti-influenza antibodies require Fc receptor engagement for in vivo protection, J. Clin. Invest., 126(2):605-10, Feb. 2016. (Epub Jan. 5, 2016).
Dilillo DJ et al., Broadly neutralizing hemagglutinin stalk-specific antibodies require FcγR interactions for protection against influenza virus in vivo, Nat. Med., 20(2):143-51, Feb. 2014. (Epub Jan. 12, 2014).
Ekiert DC et al., A highly conserved neutralizing epitope on group 2 influenza A viruses, Science, 333(6044):843-50, Aug. 12, 2011. (Epub Jul. 7, 2011).
Ekiert DC et al., Cross-neutralization of influenza A viruses mediated by a single antibody loop, Nature, 489(7417):526-32, Sep. 27, 2012. (Epub Sep. 16, 2012).
Emsley P et al., Cowtan, Features and development of Coot, Acta Crystallogr. D Biol. Crystallogr., 66(Pt 4):486-501, Apr. 2010. (Epub Mar. 24, 2010).
Fisher K et al., Transduction with recombinant adeno-associated virus for gene therapy is limited by leading-strand synthesis, J. Virol., 70(1):520-32. Jan. 1996.
Forsman A et al., Llama antibody fragments with cross-subtype human immunodeficiency virus type 1 (HIV-1)-neutralizing properties and high affinity for HIV-1 gp120. J. Virol., 82(24):12069-81, Dec. 2008. (Epub Oct. 8, 2008).
Friesen RH et al., A common solution to group 2 influenza virus neutralization. Proc. Natl. Acad. Sci. U.S.A. 111(1):445-50, Jan. 7, 2014. (Epub Dec. 11, 2013).
Gao G et al. Purification of recombinant adeno-associated virus vectors by column chromatography and its performance in vivo. Human Gene Therapy, 11(15):2079-91, Oct. 10, 2000.
Gao GP et al., Novel adeno-associated viruses from rhesus monkeys as vectors for human gene therapy, Proc Natl Acad Sci USA, 99(18):11854-9, Sep. 3, 2002. (Epub Aug. 21, 2002).
Gao R et al., Human infection with a novel avian-origin influenza A (H7N9) virus. N. Engl. J. Med., 368:1888-97, May 16, 2013. (Epub Apr. 11, 2013).
Glaven RH et al., Linking Single Domain Antibodies that Recognize Different Epitopes on the Same Target, Biosensors (Basel), 2(1):43-56, Feb. 1, 2012.
Gupta P, Preclinical pharmacokinetics of MHAA4549A, a human monoclonal antibody to influenza A virus, and the prediction of its efficacious clinical dose for the treatment of patients hospitalized with influenza A, Mabs, 8(5):991-7, Jul. 2016. (Epub Mar. 31, 2016).
Harris A et al., Influenza virus pleiomorphy characterized by cryoelectron tomograph, Proc. Natl. Acad. Sci. U.S.A., 103(50)19123-7, Dec. 12, 2006. (Epub Dec. 4, 2006).
Hessell AJ et al., Fc receptor but not complement binding is important in antibody protection against HIV, Nature, 449(7158):101-104, Sep. 6, 2007.

(56) References Cited

OTHER PUBLICATIONS

Hinderer C et al., Severe Toxicity in Nonhuman Primates and Piglets Following High-Dose Intravenous Administration of an Adeno-Associated Virus Vector Expressing Human SMN, Human Gene Therapy, 29(3):285-298, Mar. 2018. (Epub Feb. 12, 2018).

Hohn M et al., SPARX, a new environment for Cryo-EM image processing, J. Struct. Biol., 157(1):47-55, Jan. 2007. (Epub Jul. 16, 2006).

Hufton SE et al. The breadth of cross sub-type neutralisation activity of a single domain antibody to influenza hemagglutinin can be increased by antibody valency, PLoS One, 9(8):e103294, Aug. 1, 2014.

Hultberg A et al., Llama-derived single domain antibodies to build multivalent, superpotent and broadened neutralizing anti-viral molecules, PLoS One 6(4):e17665, Apr. 1, 2011.

Invivogen, IgG-Fc Engineering For Therapeutic Use, available online at www.invivogen.com/docs/Insight200605.pdf, Apr. 2006.

Irani V et al., Molecular properties of human IgG subclasses and their implications for designing therapeutic monoclonal antibodies against infectious diseases, Molecular immunology, 67(2):171-82, Oct. 2015. (Epub Apr. 18, 2015).

Jegaskanda PC et al., Influenza-specific antibody-dependent cellular cytotoxicity: toward a universal influenza vaccine, J. Immunol. 193(2):469-75, Jul. 15, 2014.

Jin X et al., Direct Liquid Chromatography/Mass Spectrometry Analysis for Complete Characterization of Recombinant Adeno-Associated Virus Capsid Proteins, Hu Gene Therapy Methods, 28(5):255-67, Oct. 2017. (Epub Jun. 16, 2017).

Julien JP et al., Structural insights into key sites of vulnerability on HIV-1 Env and influenza HA, Immunol. Rev., 250(1):180-98, Nov. 2012.

Kabsch W, XDS, Acta Crystallogr. D Biol. Crystallogr., 66(Pt 2):125-32, Feb. 2010. (Epub Jan. 22, 2010).

Kashyap AK et al., Combinatorial antibody libraries from survivors of the Turkish H5N1 avian influenza outbreak reveal virus neutralization strategies, Proc. Natl. Acad. Sci. U.S.A., 105(16):5986-91, Apr. 22, 2008. (Epub Apr. 14, 2008).

Kashyap AK et al., Protection from the 2009 H1N1 Pandemic Influenza by an Antibody from Combinatorial Survivor-Based Libraries, PLoS Pathog., 6(7):e1000990, Jul. 2010.

Kelly S et al., Splicing of many human genes involves sites embedded within introns, Nucleic Acids Research, 43(9):4721-32, May 19, 2015. (Epub Apr. 20, 2015).

Klein C et al., Progress in overcoming the chain association issue in bispecific heterodimeric IgG antibodies, mAbs, 4(6):653-63, Nov.-Dec. 2012. (Epub Aug. 27, 2012).

Krah S et al., Single-domain antibodies for biomedical applications, Immunopharmacol. Immunotoxicol., 38(1):21-28, 2016. (Epub Nov. 9, 2015).

Kramer RA et al., A novel helper phage that improves phage display selection efficiency by preventing the amplification of phages without recombinant protein. Nucleic Acids Res., 31(11):e59, Jun. 1, 2003.

Kramer RA et al., The human antibody repertoire specific for rabies virus glycoprotein as selected from immune libraries, Eur. J. Immunol., 35(7):2131-45, Jul. 2005.

Krause et al., Human Monoclonal Antibodies to Pandemic 1957 H2N2 and Pandemic 1968 H3N2 Influence Viruses, Journal of Virology, 86(11):6334-6340, Jun. 2012.

Kuo TT et al., Neonatal Fc Receptor and IgG-Based Therapeutics, mAbs, 3(5):422-30, Sep.-Oct. 2011. (Epub Sep. 1, 2011).

Labrijn et al., Efficient generation of stable bispecific IgG1 by controlled Fab-arm exchange, PProc Natl Acad Sci USA, 110(13):5145-50, Mar. 26, 2013. (Epub Mar. 11, 2013).

Lander et al., Appion: an integrated, database-driven pipeline to facilitate EM image processing, J. Struct. Biol., 166(1):95-102, Apr. 2009.

Laursen S and Wilson IA, Broadly neutralizing antibodies against influenza viruses, Antiviral. Res. 98(3):476-83, Jun. 2013. (Epub Apr. 9, 2013).

Lee PS et al., Heterosubtypic antibody recognition of the influenza virus hemagglutinin receptor binding site enhanced by avidity. Proc. Natl. Acad. Sci. U.S.A. 109(42):17040-5, Oct. 16, 2012. (Epub Oct. 1, 2012).

Limberis MP et al., Transduction efficiencies of novel AAV vectors in mouse airway epithelium in vivo and human ciliated airway epithelium in vitro, Mol. Ther., 17(2):294-301, Feb. 2009. (Epub Dec. 9, 2008).

Liu J et al., Highly pathogenic H5N1 influenza virus infection in migratory birds, Science, 309(5738):1206m, Aug. 19, 2005. (Epub Jul. 6, 2005).

Lobner E et al., Engineered IgG1-Fc—one fragment to bind them all, Immunological reviews, 270(1):113-131, Mar. 2016. (Epub Feb. 10, 2016).

McCoy AJ et al., Likelihood-enhanced fast translation functions. Acta Crystallogr. D Biol. Crystallogr. 61(Pt 4):458-64, Apr. 2005. (Epub Mar. 24, 2005).

Miller et al., Visualization of murine intranasal dosing efficiency using luminescent Francisella tularensis: effect of instillation volume and form of anesthesia. PLoS One. 2012;7(2):e31359. doi: 10.1371/journal.pone.0031359. Epub Feb. 24, 2012.

Mouquet H et al., Enhanced HIV-1 neutralization by antibody heteroligation, Proc. Natl. Acad. Sci. U.S.A., 109(3):875-80, Jan. 17, 2012. (Epub Jan. 4, 2012).

Murshudov GN et al., Refinement of macromolecular structures by the maximum-likelihood method, Acta Crystallogr. D Biol. Crystallogr., 53(Pt 3):240-55, May 1, 1997.

Ogura T et al., Topology representing network enables highly accurate classification of protein images taken by cryo electron-microscope without masking, J. Struct. Biol., 143(3):185-200, Sep. 2003.

Osterholm MT et al., Efficacy and effectiveness of influenza vaccines: a systematic review and meta-analysis. Lancet Infect Dis. 12(1):36-44, Jan. 2012. (Epub Oct. 25, 2011).

Ostrowski et al., Targeting expression of a transgene to the airway surface epithelium using a ciliated cell-specific promoter. Mol Ther. Oct. 2003;8(4):637-45. (Oct. 2003).

Pettersen EF et al., UCSF Chimera—a visualization system for exploratory research and analysis, J. Comput. Chem., 25(13):1605-12, Oct. 2004.

Rath T et al., Fc-fusion proteins and FcRn: structural insights for longer-lasting and more effective therapeutics, Critical reviews in biotechnology, 35(2):235-54, Jun. 2015. (Epub Oct. 24, 2013).

Roseman AM, FindEM—a fast, efficient program for automatic selection of particles from electron micrographs, J. Struct. Biol., 145(1-2):91-9, Jan.-Feb. 2004.

Sanner MF et al., Reduced surface: an efficient way to compute molecular surfaces, Biopolymers, 38(3):305-20, Mar. 1996.

Saxena A and Wu D, Advances in therapeutic Fc engineering—modulation of IgG-Associated effector functions and serum half-life, Frontiers in immunology, 7:580, Dec. 12, 2016.

Scheres SH, A Bayesian view on cryo-EM structure determination, J. Mol. Biol., 415(2):406-18, Jan. 13, 2012. (Epub Nov. 12, 2011).

Shepelev V and Fedorov A. Advances in the Exon-Intron Database. Briefings in Bioinformatics, 7(2):178-85, Jun. 2006. (Epub Mar. 9, 2006).

Strohl WR, Optimization of Fc-Mediated Effector Functions of Monoclonal Antibodies, Current Opinion in Biotechnology, 20(6):685-91, Dec. 2009. (Epub Nov. 4, 2009).

Tan GS et al., A pan-H1 anti-hemagglutinin monoclonal antibody with potent broad-spectrum efficacy in vivo, 86(11):6179-88, Jun. 2012. (Epub Apr. 4, 2012).

Tang G et al., EMAN2: an extensible image processing suite for electron microscopy, J. Struct. Biol., 157(1):38-46, Jan. 2007. (Epub Jun. 8, 2006).

Throsby M et al., Heterosubtypic neutralizing monoclonal antibodies cross-protective against H5N1 and H1N1 recovered from human IgM$^+$ memory B cells, PLoS One, 3(12): e3942, 2008. (Epub Dec. 16, 2008).

Tillib et al., Formatted single-domain antibodies can protect mice against infection with influenza virus (H5N2), Antiviral Research. 97(3):245-54, Mar. 2013. (Epub Dec. 25, 2012).

(56) References Cited

OTHER PUBLICATIONS

Tsibane et al., Influenza human monoclonal antibody 1F1 interacts with three major antigenic sites and residues mediating human receptor specificity in H1N1 viruses, PLoS Pathog., 8(12):e1003067, 2012. (Epub Dec. 6, 2012).
Vafa O et al., An engineered Fc variant of an IgG eliminates all immune effector functions via structural perturbations, Methods, 65(1):114-26, Jan. 1, 2014. (Epub Jul. 17, 2013).
Vanlandschoot P et al., Nanobodies: new ammunition to battle viruses, Antiviral Res., 92(3):389-407, Dec. 2011. (Epub Sep. 10, 2011).
Wang TT et al., Broadly protective monoclonal antibodies against H3 influenza viruses following sequential immunization with different hemagglutinins, PLoS Pathog., 6(2):e1000796, Feb. 26, 2010.
Ward et al., Codon optimization of human factor VIII cDNAs leads to high-level expression. Blood. Jan. 20, 2011;117(3):798-807. doi: 10.1182/blood-2010-05-282707. Epub Nov. 1, 2010.
Wu Y et al., A potent broad-spectrum protective human monoclonal antibody crosslinking two haemagglutinin monomers of influenza A virus, Nat. Commun., 6:7708, Jul. 21, 2015.
Wu Z et al., Effect of genome size on AAV vector packaging, Mol Ther, 18(1):80-6, Jan. 2010. (Epub Nov. 10, 2009).
Xie H et al., H3N2 Mismatch of 2014-15 Northern Hemisphere Influenza Vaccines and Head-to-head Comparison between Human and Ferret Antisera derived Antigenic Maps, Sci. Rep., 5:15279, Oct. 16, 2015.
Xu R et al., Structural basis of preexisting immunity to the 2009 H1N1 pandemic influenza virus, Science, 328(5976):357-60, Apr. 16, 2010. (Epub Mar. 25, 2010).
Yang Z et al., Iterative stable alignment and clustering of 2D transmission electron microscope images, Structure, 20(2):237-47, Feb. 8, 2012.
Yoshida R et al., Cross-protective potential of a novel monoclonal antibody directed against antigenic site B of the hemagglutinin of influenza A viruses, PLoS Pathog., 5(3):e1000350, Mar. 2009. (Epub Mar. 20, 2009).
Zanta-Boussif MA et al., Validation of a mutated PRE sequence allowing high and sustained transgene expression while abrogating WHV-X protein synthesis: application to the gene therapy of WAS, Gene Therapy, 16(5):605-19, May 2009. (Epub Mar. 5, 2009).
Center for Disease Control and Prevention,"Types of Influenza Viruses" Web page <https://www.cdc.gov/flu/about/viruses/types.htm>, 2 pages, Apr. 4, 2016, page last updated Aug. 19, 2014, retrieved from Internet Archive Wayback Machine <https://web.archive.org/web/20160404144120/https://www.cdc.gov/flu/about/viruses/types.htm> on May 11, 2018.
Centers for Disease Control and Prevention, Estimates of deaths associated with seasonal influenza: United States, 1976-2007, available in MMWR Morb. Mortal. Wkly. Rep. 59:1057-1062, Aug. 27, 2010.
European Medicines Agency, Guideline on Development, Production, Characterisation and Specifications for Monoclonal Antibodies and Related Products (EMEA/CHMP/BWP/157653/2007), published Dec. 2008.
U.S. Department of Health and Human Services, Food and Drug Administration, Center for Biologies Evaluation, "Research Points to Consider in the Manufacture and Testing of Monoclonal Ab Products for Human Use," published in Feb. 1997.
International Search Report and Written Opinion in International Application No. PCT/US2018/019974 dated Apr. 11, 2018.
Maria P. Limberis, Anna P. Tretiakova, James M. Wilson, Michael Naso, Joost Kolkman, Robert Friesen, and Qiang Wang. U.S. Appl. No. 15/906,887, filed Feb. 27, 2018.
Requirement for Restriction/Election issued in parent U.S. Appl. No. 14/787,622, dated Jul. 21, 2016.
Response dated Jul. 21, 2016 Requirement for Restriction/Election issued in parent U.S. Appl. No. 14/787,622, filed Nov. 21, 2016.
Wilson, U.S. Appl. No. 14/112,802, filed Oct. 18, 2013, US 2014-0031418 A1, Jan. 30, 2014.
Wilson, U.S. Appl. No. 15/310,555, filed Nov. 11, 2016, US 2017-0081392 A1, Mar. 23, 2017.
Dec. 19, 2016, US, PCT/US2016/032063.
Adam, Clin Vaccine Immunol., Adeno-associated virus 9-mediated airway expression of antibody protects old and immunodeficient mice against influenza virus., vol. 21, No. 11, pp. 1528-1533, Sep. 10, 2014.
Limberis, Sci. Transl. Med., Intranasal antibody gene transfer in mice and ferrets elicits broad protection against pandemic influenza, vol. 5, No. 187, pp. 1-8, May 29, 2013.
Corti, Science, A neutralizing antibody selected from plasma cells that binds to group 1 and group 2 influenza A hemagglutinins., vol. 333, No. 6044, pp. 850-856, Aug. 12, 2011.
Dreyfus, Science, Highly conserved protective epitopes on influenza B viruses., vol. 337, No. 6100, pp. 1343-1348, Sep. 14, 2012.
First Office Action dated Dec. 22, 2020, in the corresponding Chinese Patent Application No. 2016800413660 with an unofficial translation prepared by the Chinese Agent.
First Examination Report dated May 19, 2021, in the corresponding Australian Patent Application No. 2016275909.
Second Examination Report dated May 17, 2022, in the corresponding Australian Patent Application No. 2016275909.
Office Action dated May 12, 2022 issued in the corresponding Canadian Patent Application No. 08938544CA.

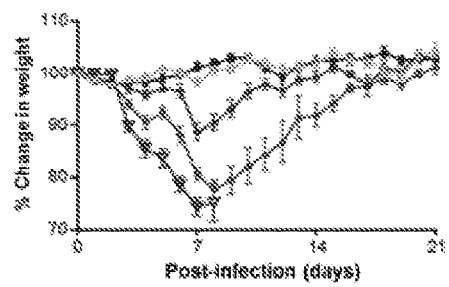
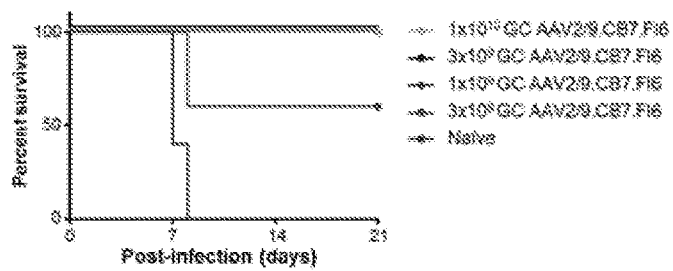
FIG 3A
FIG 3B
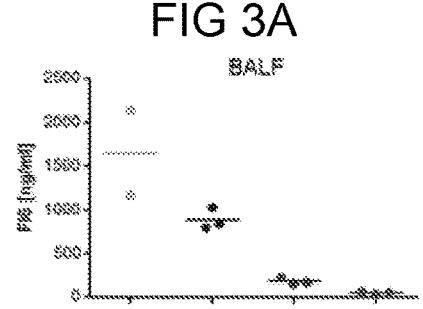
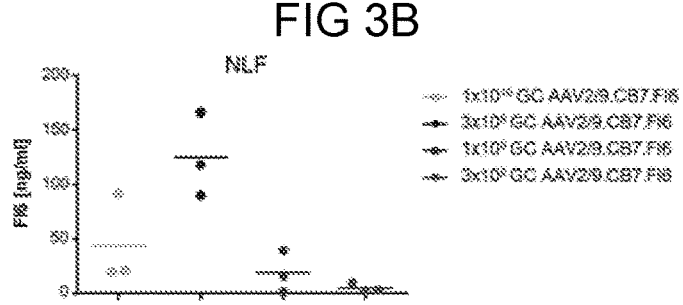
FIG 4A
FIG 4B
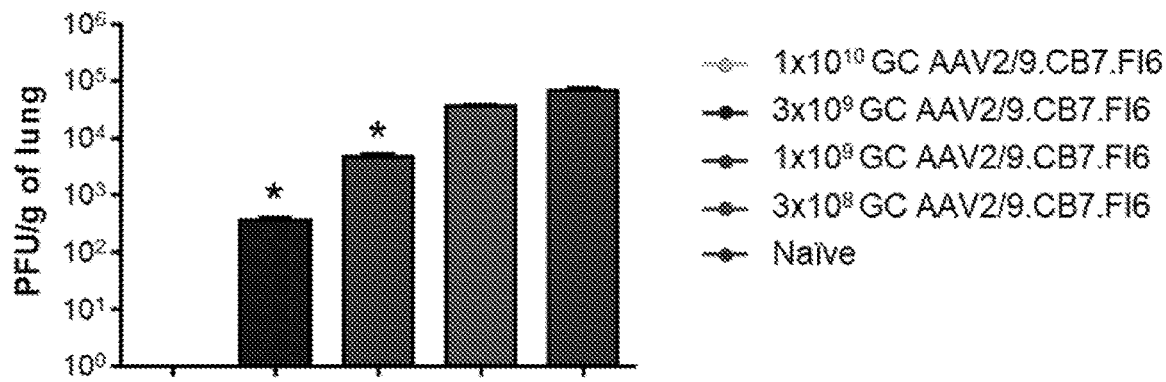
FIG 5

FIG 12A
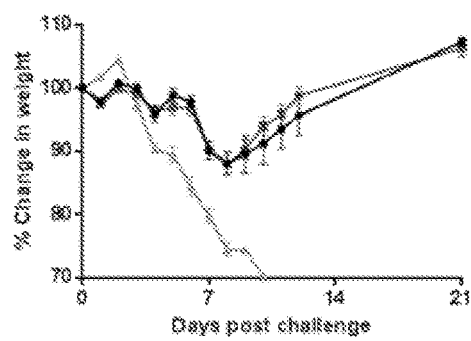
FIG 12B
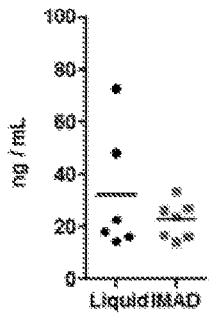
FIG 12C
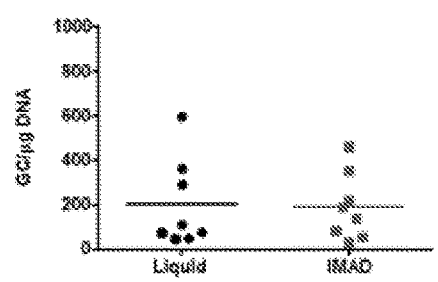
FIG 12D
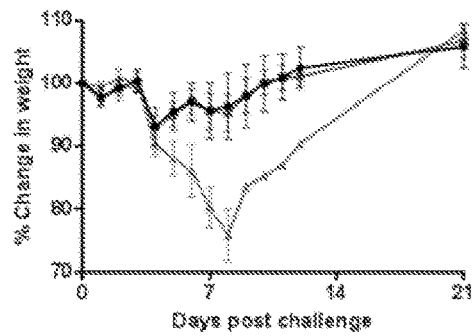
FIG 12E
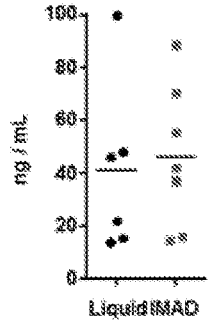
FIG 12F
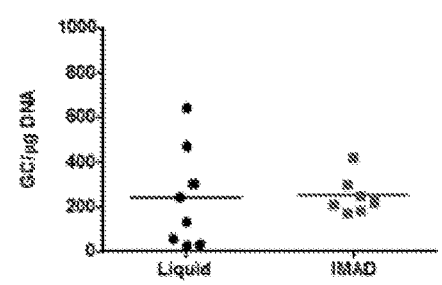
FIG 12G
| Starting volume (mL) | Volume post IMAD (mL) |
|---|---|
| 0.500 | 0.467 |
| 0.500 | 0.480 |

SEQUENCE LISTING

```
<160> NUMBER OF SEQ ID NOS: 25

<210> SEQ ID NO 1
<211> LENGTH: 7908
<212> TYPE: DNA
<213> ORGANISM: Artificial Sequence
<220> FEATURE:
<223> OTHER INFORMATION: Plasmid carrying FI6cc HC with germline light
      chain
<220> FEATURE:
<221> NAME/KEY: repeat_region
<222> LOCATION: (1)..(130)
<223> OTHER INFORMATION: 5' ITR
<220> FEATURE:
<221> NAME/KEY: repeat_region
<222> LOCATION: (198)..(579)
<223> OTHER INFORMATION: CMV IE promoter
<220> FEATURE:
<221> NAME/KEY: promoter
<222> LOCATION: (582)..(862)
<220> FEATURE:
<221> NAME/KEY: TATA_signal
<222> LOCATION: (836)..(839)
<220> FEATURE:
<221> NAME/KEY: Intron
<222> LOCATION: (956)..(1928)
<223> OTHER INFORMATION: chicken beta-actin intron
<220> FEATURE:
<221> NAME/KEY: misc_feature
<222> LOCATION: (1940)..(1987)
<223> OTHER INFORMATION: c-myc 5'UTR
<220> FEATURE:
<221> NAME/KEY: misc_feature
<222> LOCATION: (1988)..(1992)
<223> OTHER INFORMATION: kozak
<220> FEATURE:
<221> NAME/KEY: misc_feature
```

```
<222> LOCATION: (1993)..(2052)
<223> OTHER INFORMATION: leader
<220> FEATURE:
<221> NAME/KEY: CDS
<222> LOCATION: (2053)..(2439)
<223> OTHER INFORMATION: FI6 variable heavy
<220> FEATURE:
<221> NAME/KEY: CDS
<222> LOCATION: (2440)..(2760)
<223> OTHER INFORMATION: FI6 CH1
<220> FEATURE:
<221> NAME/KEY: CDS
<222> LOCATION: (2761)..(3426)
<223> OTHER INFORMATION: FI6 CH2-3
<220> FEATURE:
<221> NAME/KEY: misc_feature
<222> LOCATION: (3427)..(3438)
<223> OTHER INFORMATION: furin cleavage site
<220> FEATURE:
<221> NAME/KEY: misc_feature
<222> LOCATION: (3439)..(3510)
<223> OTHER INFORMATION: F2A
<220> FEATURE:
<221> NAME/KEY: misc_feature
<222> LOCATION: (3511)..(3570)
<223> OTHER INFORMATION: leader
<220> FEATURE:
<221> NAME/KEY: CDS
<222> LOCATION: (3511)..(3570)
<223> OTHER INFORMATION: leader
<220> FEATURE:
<221> NAME/KEY: CDS
<222> LOCATION: (3571)..(3909)
<223> OTHER INFORMATION: kagga germline line
<220> FEATURE:
<221> NAME/KEY: CDS
<222> LOCATION: (3910)..(4230)
<220> FEATURE:
<221> NAME/KEY: repeat_region
<222> LOCATION: (4308)..(4432)
<223> OTHER INFORMATION: rabbit globin polyA
<220> FEATURE:
<221> NAME/KEY: repeat_region
<222> LOCATION: (4521)..(4650)
<223> OTHER INFORMATION: 3' ITR
<220> FEATURE:
<221> NAME/KEY: misc_feature
<222> LOCATION: (4827)..(5265)
<223> OTHER INFORMATION: F1 ori on complementary strand
<220> FEATURE:
<221> NAME/KEY: misc_feature
<222> LOCATION: (5294)..(5936)
<223> OTHER INFORMATION: origin of replication
<220> FEATURE:
<221> NAME/KEY: misc_feature
<222> LOCATION: (6611)..(7426)
<223> OTHER INFORMATION: CDS for Kan resistance located on complementary
      strand

<400> SEQUENCE: 1
ctgcgcgctc gctcgctcac tgaggccgcc cgggcaaagc ccgggcgtcg ggcgaccttt       60
ggtcgcccgg cctcagtgag cgagcgagcg cgcagagagg gagtggccaa ctccatcact      120
aggggttcct tgtagttaat gattaacccg ccatgctact tatctaccag ggtaatgggg      180
atcctctaga actatagcta gtcgacattg attattgact agttattaat agtaatcaat      240
tacggggtca ttagttcata gcccatatat ggagttccgc gttacataac ttacggtaaa      300
tggcccgcct ggctgaccgc ccaacgaccc ccgcccattg acgtcaataa tgacgtatgt      360
tcccatagta acgccaatag ggactttcca ttgacgtcaa tgggtggagt atttacggta      420
aactgcccac ttggcagtac atcaagtgta tcatatgcca gtacgccccc tattgacgt       480 caatgacggt aaatggcccg cctggcatta tgcccagtac atgaccttat gggactttcc      540
```

-continued

```
tacttggcag tacatctacg tattagtcat cgctattacc atggtcgagg tgagccccac     600
gttctgcttc actctcccca tctcccccc ctccccaccc ccaatttgt atttatttat      660
tttttaatta ttttgtgcag cgatggggc ggggggggg gggggcgcg cgccaggcgg       720
ggcggggcgg ggcgagggc ggggcgggc gaggcggaga ggtgcggcgg cagccaatca      780
gagcggcgcg ctccgaaagt ttccttttat ggcgaggcgg cggcggcggc ggccctataa    840
aaagcgaagc gcgcggcggg cgggagtcgc tgcgcgctgc cttcgccccg tgccccgctc    900
cgccgccgcc tcgcgccgcc cgccccggct ctgactgacc gcgttactcc cacaggtgag    960
cgggcgggac ggcccttctc ctccgggctg taattagcgc ttggtttaat gacggcttgt   1020
ttcttttctg tggctgcgtg aaagccttga ggggctccgg gagggccctt tgtgcggggg   1080
gagcggctcg gggggtgcgt gcgtgtgtgt gtgcgtgggg agcgccgcgt gcggctccgc   1140
gctgcccggc ggctgtgagc gctgcgggcg cggcgcgggg ctttgtgcgc tccgcagtgt   1200
gcgcgagggg agcgcggccg ggggcggtgc cccgcggtgc gggggggct gcgaggggaa    1260
caaaggctgc gtgcggggtg tgtgcgtggg ggggtgagca ggggtgtgg gcgcgtcggt    1320
cgggctgcaa ccccccctgc accccctcc ccgagttgct gagcacggcc cggcttcggg    1380
tgcggggctc cgtacggggc gtggcgcggg gctcgccgtg ccgggcgggg ggtggcggca   1440
ggtgggggtg ccgggcgggg cggggccgcc tcgggccggg gagggctcgg ggaggggcg    1500
cggcggcccc cggagcgccg gcggctgtcg aggcgcggcg agccgcagcc attgcctttt   1560
atggtaatcg tgcgagaggg cgcagggact tcctttgtcc caaatctgtg cggagccgaa   1620
atctgggagg cgccgccgca ccccctctag cgggcgcggg gcgaagcggt gcggcgccgg   1680
caggaaggaa atgggcgggg agggccttcg tgcgtcgccg cgccgccgtc cccttctccc   1740
tctccagcct cggggctgtc cgcgggggga cggctgcctt cggggggac ggggcagggc    1800
ggggttcggc ttctggcgtg tgaccggcgg ctctagagcc tctgctaacc atgttcatgc   1860
cttcttcttt ttcctacagc tcctgggcaa cgtgctggtt attgtgctgt ctcatcattt   1920
tggcaaagaa ttcgctagcg ggcactttgc actggaactt acaacaccg agcaaggacg    1980
cgactctcca ccatgtacag aatgcagctg ctgagctgca tcgccctgag cctggccctg   2040
gtgaccaaca gc cag gtg caa cta gtg gag agc gga gga gga gtg gtg cag   2091
               Gln Val Gln Leu Val Glu Ser Gly Gly Gly Val Val Gln
               1               5                   10 cca gga cgg agc ctg cgg ctg agc tgc gcc gcc agc gga ttc acc ttc      2139
Pro Gly Arg Ser Leu Arg Leu Ser Cys Ala Ala Ser Gly Phe Thr Phe
 15              20                  25 agc acc tac gcc atg cac tgg gtg cgg cag gcc cca gga aag gga ctg      2187
Ser Thr Tyr Ala Met His Trp Val Arg Gln Ala Pro Gly Lys Gly Leu
30              35                  40                  45 gag tgg gtg gcc gtg atc agc tac gat gcc aac tac aag tac tac gcc      2235
Glu Trp Val Ala Val Ile Ser Tyr Asp Ala Asn Tyr Lys Tyr Tyr Ala
                50                  55                  60 gat agc gtg aag gga cgg ttc acc atc agc cgg gat aac agc aag aac      2283
Asp Ser Val Lys Gly Arg Phe Thr Ile Ser Arg Asp Asn Ser Lys Asn
            65                  70                  75 acc ctg tac ctg cag atg aac agc ctg cgg gcc gag gat acc gcc gtg      2331
Thr Leu Tyr Leu Gln Met Asn Ser Leu Arg Ala Glu Asp Thr Ala Val
                80                  85                  90 tac tac tgc gcc aag gat agc cag ctg cgg agc ctg ctg tac ttc gag      2379
Tyr Tyr Cys Ala Lys Asp Ser Gln Leu Arg Ser Leu Leu Tyr Phe Glu
            95                  100                 105 tgg ctg agc cag gga tac ttc gat tac tgg gga cag gga acc ctg gtg      2427
```

```
                                                          -continued

Trp Leu Ser Gln Gly Tyr Phe Asp Tyr Trp Gln Gly Thr Leu Val
110             115                 120                 125 acc gtg agc agc gcc agc acc aag ggg ccc agc gtg ttc cca ctg gcc      2475
Thr Val Ser Ser Ala Ser Thr Lys Gly Pro Ser Val Phe Pro Leu Ala
                    130                 135                 140 cca agc agc aag agc acc agc gga gga acc gcc gcc ctg gga tgc ctg      2523
Pro Ser Ser Lys Ser Thr Ser Gly Gly Thr Ala Ala Leu Gly Cys Leu
            145                 150                 155 gtg aag gat tac ttc cca gag cca gtg acc gtg agc tgg aac agc gga      2571
Val Lys Asp Tyr Phe Pro Glu Pro Val Thr Val Ser Trp Asn Ser Gly
        160                 165                 170 gcc ctg acc agc gga gtg cac acc ttc cca gcc gtg ctg cag agc agc      2619
Ala Leu Thr Ser Gly Val His Thr Phe Pro Ala Val Leu Gln Ser Ser
    175                 180                 185 gga ctg tat agc ctg agc agc gtg gtg acc gtg cca agc agc agc ctg      2667
Gly Leu Tyr Ser Leu Ser Ser Val Val Thr Val Pro Ser Ser Ser Leu
190                 195                 200                 205 gga acc cag acc tac atc tgc aac gtg aac cac aag cca agc aac acc      2715
Gly Thr Gln Thr Tyr Ile Cys Asn Val Asn His Lys Pro Ser Asn Thr
                    210                 215                 220 aag gtg gat aag aag gtg gag cca aag agc tgc gat aag acc cac acg      2763
Lys Val Asp Lys Lys Val Glu Pro Lys Ser Cys Asp Lys Thr His Thr
            225                 230                 235 tgc cct cca tgt cca gcc ccc gaa ctg ctg ggc ggg cct agc gtg ttc      2811
Cys Pro Pro Cys Pro Ala Pro Glu Leu Leu Gly Gly Pro Ser Val Phe
        240                 245                 250 ctg ttt ccc cct aag cct aaa gat aca ctg atg att agt aga acc cca      2859
Leu Phe Pro Pro Lys Pro Lys Asp Thr Leu Met Ile Ser Arg Thr Pro
    255                 260                 265 gag gtc aca tgc gtg gtc gtg gac gtg tcc cac gaa gag cct gac gtg      2907
Glu Val Thr Cys Val Val Val Asp Val Ser His Glu Glu Pro Asp Val
270                 275                 280                 285 aag ttc aac tgg tac gtg gat ggc gtg gag gtg cac aat gct aag act      2955
Lys Phe Asn Trp Tyr Val Asp Gly Val Glu Val His Asn Ala Lys Thr
                    290                 295                 300 aaa cca cgc gaa gag cag tat aat agt aca tac cga gtc gtg tca gtc      3003
Lys Pro Arg Glu Glu Gln Tyr Asn Ser Thr Tyr Arg Val Val Ser Val
            305                 310                 315 ctg aca gtg ctg cac cag gat tgg ctg aac ggc aag gag tat aag tgc      3051
Leu Thr Val Leu His Gln Asp Trp Leu Asn Gly Lys Glu Tyr Lys Cys
        320                 325                 330 aag gtg tct aac aag gcc ctg ccc gcc cct atc gag aaa aca att agc      3099
Lys Val Ser Asn Lys Ala Leu Pro Ala Pro Ile Glu Lys Thr Ile Ser
    335                 340                 345 aag gcc aaa ggg cag cca cgg gaa ccc cag gtc tac act ctg cca ccc      3147
Lys Ala Lys Gly Gln Pro Arg Glu Pro Gln Val Tyr Thr Leu Pro Pro
350                 355                 360                 365 tca aga gat gaa ctg act aag aac cag gtc agc ctg acc tgt ctg gtg      3195
Ser Arg Asp Glu Leu Thr Lys Asn Gln Val Ser Leu Thr Cys Leu Val
                    370                 375                 380 aaa ggc ttc tac ccc agc gac atc gcc gtg gag tgg gaa agt aac ggc      3243
Lys Gly Phe Tyr Pro Ser Asp Ile Ala Val Glu Trp Glu Ser Asn Gly
            385                 390                 395 cag cct gag aat aac tac aag act acc cct cca gtg ctg gat agc gac      3291
Gln Pro Glu Asn Asn Tyr Lys Thr Thr Pro Pro Val Leu Asp Ser Asp
        400                 405                 410 ggg tcc ttc ttc ctg tat agc aag ctg aca gtg gac aaa tcc cgc tgg      3339
Gly Ser Phe Phe Leu Tyr Ser Lys Leu Thr Val Asp Lys Ser Arg Trp
    415                 420                 425
```

| | |
|---|---|
| cag cag gga aac gtc ttt tcc tgt tct gtg atg cat gag gcc ctg cac<br>Gln Gln Gly Asn Val Phe Ser Cys Ser Val Met His Glu Ala Leu His<br>430                          435                       440                    445 | 3387 |
| aat cat tac acc cag aag agt ctg tca ctg agc ccc ggc agaaagcgga<br>Asn His Tyr Thr Gln Lys Ser Leu Ser Leu Ser Pro Gly<br>                    450                       455 | 3436 |
| gagcccccgt gaagcagacc ctgaacttcg acctgctgaa gctggccggc gacgtggaaa | 3496 |
| gcaaccctgg ccct atg tac aga atg cag ctg ctg ctg atc gcc ctg<br>                     Met Tyr Arg Met Gln Leu Leu Leu Leu Ile Ala Leu<br>                                    460                       465                       470 | 3546 |
| agc ctg gcc ctg gtg acc aac agc gat atc gtc atg acc cag agc cca<br>Ser Leu Ala Leu Val Thr Asn Ser Asp Ile Val Met Thr Gln Ser Pro<br>                    475                       480                       485 | 3594 |
| gat agc ctg gcc gtg agc ctg gga gag cgg gcc acc atc aac tgc aag<br>Asp Ser Leu Ala Val Ser Leu Gly Glu Arg Ala Thr Ile Asn Cys Lys<br>           490                       495                       500 | 3642 |
| agc agc cag agc gtg ctg tac agc agc aac aac aag aac tac ctg gcc<br>Ser Ser Gln Ser Val Leu Tyr Ser Ser Asn Asn Lys Asn Tyr Leu Ala<br>                505                       510                       515 | 3690 |
| tgg tac cag cag aag cca gga cag cca cca aag ctg ctg atc tac tgg<br>Trp Tyr Gln Gln Lys Pro Gly Gln Pro Pro Lys Leu Leu Ile Tyr Trp<br>520                          525                       530 | 3738 |
| gcc agc acc cgg gag agc gga gtg cca gat cgg ttc agc gga agc gga<br>Ala Ser Thr Arg Glu Ser Gly Val Pro Asp Arg Phe Ser Gly Ser Gly<br>535                          540                       545                       550 | 3786 |
| agc gga acc gat ttc acc ctg acc atc agc agc ctg cag gcc gag gat<br>Ser Gly Thr Asp Phe Thr Leu Thr Ile Ser Ser Leu Gln Ala Glu Asp<br>                555                       560                       565 | 3834 |
| gtg gcc gtg tac tac tgc cag cag tac tac agc acc cca ctg acc ttc<br>Val Ala Val Tyr Tyr Cys Gln Gln Tyr Tyr Ser Thr Pro Leu Thr Phe<br>           570                       575                       580 | 3882 |
| gga cag gga acc aag gtg gag atc aag cgt acg gtg gcc gcc cca agc<br>Gly Gln Gly Thr Lys Val Glu Ile Lys Arg Thr Val Ala Ala Pro Ser<br>                585                       590                       595 | 3930 |
| gtg ttc atc ttc cca cca agc gat gag cag ctg aag agc gga acc gcc<br>Val Phe Ile Phe Pro Pro Ser Asp Glu Gln Leu Lys Ser Gly Thr Ala<br>600                          605                       610 | 3978 |
| agc gtg gtg tgc ctg ctg aac aac ttc tac cca cgg gag gcc aag gtg<br>Ser Val Val Cys Leu Leu Asn Asn Phe Tyr Pro Arg Glu Ala Lys Val<br>615                          620                       625                       630 | 4026 |
| cag tgg aag gtg gat aac gcc ctg cag agc gga aac agc cag gag agc<br>Gln Trp Lys Val Asp Asn Ala Leu Gln Ser Gly Asn Ser Gln Glu Ser<br>                635                       640                       645 | 4074 |
| gtg acc gag cag gat agc aag gat agc acc tac agc ctg agc agc acc<br>Val Thr Glu Gln Asp Ser Lys Asp Ser Thr Tyr Ser Leu Ser Ser Thr<br>           650                       655                       660 | 4122 |
| ctg acc ctg agc aag gcc gat tac gag aag cac aag gtg tac gcc tgc<br>Leu Thr Leu Ser Lys Ala Asp Tyr Glu Lys His Lys Val Tyr Ala Cys<br>                665                       670                       675 | 4170 |
| gag gtg acc cac cag gga ctg agc agc cca gtg acc aag agc ttc aac<br>Glu Val Thr His Gln Gly Leu Ser Ser Pro Val Thr Lys Ser Phe Asn<br>680                          685                       690 | 4218 |
| cgc gga gag tgc tgataaagcg gccgcggtac ctctagagtc gacccgggcg<br>Arg Gly Glu Cys<br>695 | 4270 |
| gcctcgagga cggggtgaac tacgcctgag gatccgatct ttttccctct gccaaaaatt | 4330 |
| atggggacat catgaagccc cttgagcatc tgacttctgg ctaataaagg aaatttattt | 4390 |
| tcattgcaat agtgtgttgg aatttttttgt gtctctcact cggaagcaat tcgttgatct | 4450 |

```
gaatttcgac cacccataat acccattacc ctggtagata agtagcatgg cgggttaatc   4510
attaactaca aggaacccct agtgatggag ttggccactc cctctctgcg cgctcgctcg   4570
ctcactgagg ccgggcgacc aaaggtcgcc cgacgcccgg gctttgcccg ggcggcctca   4630
gtgagcgagc gagcgcgcag ccttaattaa cctaattcac tggccgtcgt tttacaacgt   4690
cgtgactggg aaaaccctgg cgttacccaa cttaatcgcc ttgcagcaca tccccctttc   4750
gccagctggc gtaatagcga agaggcccgc accgatcgcc cttcccaaca gttgcgcagc   4810
ctgaatggcg aatgggacgc gccctgtagc ggcgcattaa gcgcggcggg tgtggtggtt   4870
acgcgcagcg tgaccgctac acttgccagc gccctagcgc ccgctccttt cgctttcttc   4930
ccttcctttc tcgccacgtt cgccggcttt ccccgtcaag ctctaaatcg ggggctccct   4990
ttagggttcc gatttagtgc tttacggcac ctcgacccca aaaaacttga ttagggtgat   5050
ggttcacgta gtgggccatc gccctgatag acggtttttc gccctttgac gttggagtcc   5110
acgttcttta atagtggact cttgttccaa actggaacaa cactcaaccc tatctcggtc   5170
tattcttttg atttataagg gattttgccg atttcggcct attggttaaa aaatgagctg   5230
atttaacaaa aatttaacgc gaattttaac aaaatcatgt gagcaaaagg ccagcaaaag   5290
gccaggaacc gtaaaaaggc cgcgttgctg cgttttttcc ataggctccg ccccccctgac  5350
gagcatcaca aaaatcgacg ctcaagtcag aggtggcgaa acccgacagg actataaaga   5410
taccaggcgt ttccccctgg aagctccctc gtgcgctctc ctgttccgac cctgccgctt   5470
accggatacc tgtccgcctt tctcccttcg ggaagcgtgg cgctttctca tagctcacgc   5530
tgtaggtatc tcagttcggt gtaggtcgtt cgctccaagc tgggctgtgt gcacgaaccc   5590
cccgttcagc ccgaccgctg cgccttatcc ggtaactatc gtcttgagtc aacccggta   5650
agacacgact tatcgccact ggcagcagcc actggtaaca ggattagcag agcgaggtat   5710
gtaggcggtg ctacagagtt cttgaagtgg tggcctaact acggctacac tagaagaaca   5770
gtatttggta tctgcgctct gctgaagcca gttaccttcg gaaaaagagt tggtagctct   5830
tgatccggca aacaaaccac cgctggtagc ggtggttttt ttgtttgcaa gcagcagatt   5890
acgcgcagaa aaaaaggatc tcaagaagat cctttgatct tttctacggg gtctgacgct   5950
cagtggaacg aaaactcacg ttaagggatt ttggtcatga gattatcaaa aaggatcttc   6010
acctagatcc ttttgatcct ccggcgttca gcctgtgcca cagccgacag gatggtgacc   6070
accatttgcc ccatatcacc gtcggtactg atcccgtcgt caataaaccg aaccgctaca   6130
ccctgagcat caaactctt tatcagttgg atcatgtcgg cggtgtcgcg gccaagacgg   6190
tcgagcttct tcaccagaat gacatcacct tcctccacct tcatcctcag caaatccagc   6250
ccttcccgat ctgttgaact gccggatgcc ttgtcggtaa agatgcggtt agcttttacc   6310
cctgcatctt tgagcgctga ggtctgcctc gtgaagaagg tgttgctgac tcataccagg   6370
cctgaatcgc cccatcatcc agccagaaag tgagggagcc acggttgatg agagctttgt   6430
tgtaggtgga ccagttggtg attttgaact tttgctttgc cacggaacgg tctgcgttgt   6490
cgggaagatg cgtgatctga tccttcaact cagcaaaagt tcgatttatt caacaaagcc   6550
gccgtcccgt caagtcagcg taatgctctg ccagtgttac aaccaattaa ccaattctga   6610
ttagaaaaac tcatcgagca tcaaatgaaa ctgcaattta ttcatatcag gattatcaat   6670
accatatttt tgaaaagcc gtttctgtaa tgaaggagaa aactcaccga gcagttcca    6730
taggatggca agatcctggt atcggtctgc gattccgact cgtccaacat caatacaacc   6790
```

```
tattaatttc ccctcgtcaa aaataaggtt atcaagtgag aaatcaccat gagtgacgac   6850
tgaatccggt gagaatggca aaagcttatg catttctttc cagacttgtt caacaggcca   6910
gccattacgc tcgtcatcaa aatcactcgc atcaaccaaa ccgttattca ttcgtgattg   6970
cgcctgagcg agacgaaata cgcgatcgct gttaaaagga caattacaaa caggaatcga   7030
atgcaaccgg cgcaggaaca ctgccagcgc atcaacaata ttttcacctg aatcaggata   7090
ttcttctaat acctggaatg ctgttttccc ggggatcgca gtggtgagta accatgcatc   7150
atcaggagta cggataaaat gcttgatggt cggaagaggc ataaattccg tcagccagtt   7210
tagtctgacc atctcatctg taacatcatt ggcaacgcta cctttgccat gtttcagaaa   7270
caactctggc gcatcgggct tcccatacaa tcgatagatt gtcgcacctg attgcccgac   7330
attatcgcga gcccatttat acccatataa atcagcatcc atgttggaat taatcgcgg   7390 cctcgagcaa gacgtttccc gttgaatatg gctcataaca ccccttgtat tactgtttat   7450
gtaagcagac agtttttattg ttcatgatga tatattttta tcttgtgcaa tgtaacatca   7510
gagattttga gacaccatgt tctttcctgc gttatcccct gattctgtgg ataaccgtat   7570
taccgccttt gagtgagctg ataccgctcg ccgcagccga acgaccgagc gcagcgagtc   7630
agtgagcgag gaagcggaag agcgcccaat acgcaaaccg cctctccccg cgcgttggcc   7690
gattcattaa tgcagctggc acgacaggtt cccgactgg aaagcgggca gtgagcgcaa   7750
cgcaattaat gtgagttagc tcactcatta ggcaccccag ctttacact ttatgcttcc   7810 ggctcgtatg ttgtgtggaa ttgtgagcgg ataacaattt cacacaggaa acagctatga   7870
ccatgattac gccagattta attaaggcct taattagg                          7908
```

<210> SEQ ID NO 2
<211> LENGTH: 129
<212> TYPE: PRT
<213> ORGANISM: Artificial Sequence
<220> FEATURE:
<223> OTHER INFORMATION: Synthetic Construct

<400> SEQUENCE: 2

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met His Trp Val Arg Gln Ala Pro Gly Lys Gly Leu Glu Trp Val
        35                  40                  45

Ala Val Ile Ser Tyr Asp Ala Asn Tyr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Gln Leu Arg Ser Leu Leu Tyr Phe Glu Trp Leu Ser
            100                 105                 110

Gln Gly Tyr Phe Asp Tyr Trp Gly Gln Gly Thr Leu Val Thr Val Ser
        115                 120                 125

Ser
```

<210> SEQ ID NO 3
<211> LENGTH: 107
<212> TYPE: PRT
<213> ORGANISM: Artificial Sequence

```
<220> FEATURE:
<223> OTHER INFORMATION: Synthetic Construct

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His
            100                 105

<210> SEQ ID NO 4
<211> LENGTH: 222
<212> TYPE: PRT
<213> ORGANISM: Artificial Sequence
<220> FEATURE:
<223> OTHER INFORMATION: Synthetic Construct

<400> SEQUENCE: 4

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Glu Pro Asp
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
            115                 120                 125

Pro Ser Arg Asp Glu Leu Thr Lys Asn Gln Val Ser Leu Thr Cys Leu
        130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly
    210                 215                 220
```

<210> SEQ ID NO 5
<211> LENGTH: 20
<212> TYPE: PRT
<213> ORGANISM: Artificial Sequence
<220> FEATURE:
<223> OTHER INFORMATION: Synthetic Construct

<400> SEQUENCE: 5

Met Tyr Arg Met Gln Leu Leu Leu Ile Ala Leu Ser Leu Ala Leu
1               5                   10                  15

Val Thr Asn Ser
            20

<210> SEQ ID NO 6
<211> LENGTH: 113
<212> TYPE: PRT
<213> ORGANISM: Artificial Sequence
<220> FEATURE:
<223> OTHER INFORMATION: Synthetic Construct

<400> SEQUENCE: 6

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gln Gly Thr Lys Val Glu Ile
            100                 105                 110

Lys

<210> SEQ ID NO 7
<211> LENGTH: 107
<212> TYPE: PRT
<213> ORGANISM: Artificial Sequence
<220> FEATURE:
<223> OTHER INFORMATION: Synthetic Construct

<400> SEQUENCE: 7

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

```
<210> SEQ ID NO 8
<211> LENGTH: 7899
<212> TYPE: DNA
<213> ORGANISM: Artificial Sequence
<220> FEATURE:
<223> OTHER INFORMATION: CIs plasmid containing CR8033 heavy chain and
      light chain from kappa germline
<220> FEATURE:
<221> NAME/KEY: misc_feature
<222> LOCATION: (264)..(287)
<223> OTHER INFORMATION: CMV promoter end
<220> FEATURE:
<221> NAME/KEY: promoter
<222> LOCATION: (285)..(565)
<223> OTHER INFORMATION: CB promoter
<220> FEATURE:
<221> NAME/KEY: misc_feature
<222> LOCATION: (288)..(318)
<223> OTHER INFORMATION: begin promoter
<220> FEATURE:
<221> NAME/KEY: TATA_signal
<222> LOCATION: (539)..(542)
<220> FEATURE:
<221> NAME/KEY: Intron
<222> LOCATION: (659)..(1631)
<223> OTHER INFORMATION: chicken beta-actin intron
<220> FEATURE:
<221> NAME/KEY: misc_feature
<222> LOCATION: (1517)..(1533)
<223> OTHER INFORMATION: end of intron
<220> FEATURE:
<221> NAME/KEY: misc_feature
<222> LOCATION: (1643)..(1690)
<223> OTHER INFORMATION: c-myc 5' UTR
<220> FEATURE:
<221> NAME/KEY: misc_feature
<222> LOCATION: (1691)..(1698)
<223> OTHER INFORMATION: kozak
<220> FEATURE:
<221> NAME/KEY: CDS
<222> LOCATION: (1753)..(2133)
<223> OTHER INFORMATION: CR8033cc variable heavy
<220> FEATURE:
<221> NAME/KEY: CDS
<222> LOCATION: (2134)..(2454)
<223> OTHER INFORMATION: CH1
<220> FEATURE:
<221> NAME/KEY: CDS
<222> LOCATION: (2455)..(3120)
<223> OTHER INFORMATION: CH2-3
<220> FEATURE:
<221> NAME/KEY: misc_feature
<222> LOCATION: (3121)..(3132)
<223> OTHER INFORMATION: furin cleavage site
<220> FEATURE:
<221> NAME/KEY: misc_feature
<222> LOCATION: (3133)..(3204)
<223> OTHER INFORMATION: F2A linker
<220> FEATURE:
<221> NAME/KEY: CDS
<222> LOCATION: (3265)..(3603)
<223> OTHER INFORMATION: Kappa germline light
<220> FEATURE:
<221> NAME/KEY: CDS
<222> LOCATION: (3604)..(3924)
<223> OTHER INFORMATION: constant light
<220> FEATURE:
<221> NAME/KEY: polyA_signal
<222> LOCATION: (4000)..(4126)
<220> FEATURE:
<221> NAME/KEY: repeat_region
<222> LOCATION: (4215)..(4344)
<223> OTHER INFORMATION: 3' ITR (on complement)
<220> FEATURE:
<221> NAME/KEY: misc_feature
<222> LOCATION: (4521)..(4959)
<223> OTHER INFORMATION: F1 ori on complementary strand
<220> FEATURE:
```

```
<221> NAME/KEY: misc_feature
<222> LOCATION: (4988)..(5630)
<223> OTHER INFORMATION: pUC origin of replication
<220> FEATURE:
<221> NAME/KEY: misc_feature
<222> LOCATION: (7363)..(7548)
<223> OTHER INFORMATION: Lac promoter
<220> FEATURE:
<221> NAME/KEY: repeat_region
<222> LOCATION: (7603)..(7732)
<223> OTHER INFORMATION: 5' ITR
<220> FEATURE:
<221> NAME/KEY: misc_feature
<222> LOCATION: (7806)..(7835)
<223> OTHER INFORMATION: promoter start

<400> SEQUENCE: 8
```

| | | | | | |
|---|---|---|---|---|---|
| aaatggcccg | cctggctgac | cgcccaacga | cccccgccca | ttgacgtcaa | taatgacgta   60 |
| tgttcccata | gtaacgccaa | tagggacttt | ccattgacgt | caatgggtgg | agtatttacg  120 |
| gtaaactgcc | cacttggcag | tacatcaagt | gtatcatatg | ccaagtacgc | cccctattga  180 |
| cgtcaatgac | ggtaaatggc | ccgcctggca | ttatgcccag | tacatgacct | tatgggactt  240 |
| tcctacttgg | cagtacatct | acgtattagt | catcgctatt | accatggtcg | aggtgagccc  300 |
| cacgttctgc | ttcactctcc | ccatctcccc | ccctcccca | ccccaattt | tgtatttatt  360 |
| tattttttaa | ttattttgtg | cagcgatggg | ggcggggggg | ggggggggc | gcgcgccagg  420 |
| cggggcgggg | cggggcgagg | ggcgggggcgg | ggcgaggcgg | agaggtgcgg | cggcagccaa  480 |
| tcagagcggc | gcgctccgaa | agtttccttt | tatggcgagg | cggcggcggc | ggcggcccta  540 |
| taaaaagcga | agcgcgcggc | gggcgggagt | cgctgcgcgc | tgccttcgcc | ccgtgccccg  600 |
| ctccgccgcc | gcctcgcgcc | gcccgccccg | gctctgactg | accgcgttac | tcccacaggt  660 |
| gagcgggcgg | gacggccctt | ctcctccggg | ctgtaattag | cgcttggttt | aatgacggct  720 |
| tgtttctttt | ctgtggctgc | gtgaaagcct | tgaggggctc | cgggagggcc | ctttgtgcgg  780 |
| ggggagcggc | tcgggggtg | cgtgcgtgtg | tgtgtgcgtg | gggagcgccg | cgtgcggctc  840 |
| cgcgctgccc | ggcggctgtg | agcgctgcgg | gcgcggcgcg | gggctttgtg | cgctccgcag  900 |
| tgtgcgcgag | gggagcgcgg | ccgggggcgg | tgccccgcgg | tgcggggggg | gctgcgaggg  960 |
| gaacaaaggc | tgcgtgcggg | gtgtgtgcgt | ggggggggtga | gcaggggggtg | tgggcgcgtc 1020 |
| ggtcgggctg | caacccccc | tgcaccccc | tccccgagtt | gctgagcacg | gcccggcttc 1080 |
| gggtgcgggg | ctccgtacgg | ggcgtggcgc | ggggctcgcc | gtgccgggcg | gggggtggcg 1140 |
| gcaggtgggg | gtgccggggcg | gggcggggcc | gcctcgggcc | ggggagggct | cggggagggg 1200 |
| gcgcggcggc | ccccggagcg | ccggcggctg | tcgaggcgcg | gcgagccgca | gccattgcct 1260 |
| tttatggtaa | tcgtgcgaga | gggcgcaggg | acttcctttg | tcccaaatct | gtgcggagcc 1320 |
| gaaatctggg | aggcgccgcc | gcacccctc | tagcgggcgc | ggggcgaagc | ggtgcggcgc 1380 |
| cggcaggaag | gaaatgggcg | gggagggcct | tcgtgcgtcg | ccgcgccgcc | gtccccttct 1440 |
| ccctctccag | cctcggggct | gtccgcgggg | gacggctgc | cttcgggggg | gacggggcag 1500 |
| ggcggggttc | ggcttctggc | gtgtgaccgg | cggctctaga | gcctctgcta | accatgttca 1560 |
| tgccttcttc | ttttttcctac | agctcctggg | caacgtgctg | gttattgtgc | tgtctcatca 1620 |
| ttttggcaaa | gaattcgcta | gcgggcactt | tgcactggaa | cttacaacac | ccgagcaagg 1680 |
| acgcgactct | ccaccatgcg | catgcagctg | ctgctgctga | tcgccctgag | cctggccctg 1740 |
| gtgaccaaca | gc gag gtg cag ctg gtg gag acc gga gga gga ctg gtg cag      1791 |
|            |    Glu Val Gln Leu Val Glu Thr Gly Gly Gly Leu Val Gln |
|            |     1         5           10 |

-continued

```
cca gga cgg agc ctg cgg ctg agc tgc gcc gcc agc gga ttc agc ttc       1839
Pro Gly Arg Ser Leu Arg Leu Ser Cys Ala Ala Ser Gly Phe Ser Phe
    15                  20                  25 gat gag tac acc atg cac tgg gtg cgg cag gcc cca gga aag gga ctg       1887
Asp Glu Tyr Thr Met His Trp Val Arg Gln Ala Pro Gly Lys Gly Leu
30                  35                  40                  45 gag tgg gtg gcc gga atc aac tgg aag gga aac ttc atg gga tac gcc       1935
Glu Trp Val Ala Gly Ile Asn Trp Lys Gly Asn Phe Met Gly Tyr Ala
                50                  55                  60 gat agc gtg cag gga cgg ttc acc atc agc cgg gat aac gga aag aac       1983
Asp Ser Val Gln Gly Arg Phe Thr Ile Ser Arg Asp Asn Gly Lys Asn
            65                  70                  75 agc ctg tac ctg cag atg aac agc ctg cgg gcc gag gat acc gcc ctg       2031
Ser Leu Tyr Leu Gln Met Asn Ser Leu Arg Ala Glu Asp Thr Ala Leu
        80                  85                  90 tac tac tgc gcc aag gat cgg ctg gag agc agc gcc atg gat atc ctg       2079
Tyr Tyr Cys Ala Lys Asp Arg Leu Glu Ser Ser Ala Met Asp Ile Leu
    95                  100                 105 gag gga gga acc ttc gat atc tgg gga cag gga acc atg gtg acc gtg       2127
Glu Gly Gly Thr Phe Asp Ile Trp Gly Gln Gly Thr Met Val Thr Val
110                 115                 120                 125 agc agc gcg tcg acc aag gga cct tcg gtc ttc ccc ctg gca ccc tcc       2175
Ser Ser Ala Ser Thr Lys Gly Pro Ser Val Phe Pro Leu Ala Pro Ser
                130                 135                 140 tcc aag agc acc tct ggg ggc aca gcg gcc ctg ggc tgc ctg gtc aag       2223
Ser Lys Ser Thr Ser Gly Gly Thr Ala Ala Leu Gly Cys Leu Val Lys
            145                 150                 155 gac tac ttc ccc gaa ccg gtg acg gtg tcg tgg aac tca ggc gcc ctg       2271
Asp Tyr Phe Pro Glu Pro Val Thr Val Ser Trp Asn Ser Gly Ala Leu
        160                 165                 170 acc agc ggc gtg cac acc ttc ccg gct gtc cta cag tcc tca gga ctc       2319
Thr Ser Gly Val His Thr Phe Pro Ala Val Leu Gln Ser Ser Gly Leu
    175                 180                 185 tac tcc ctc agc agc gtg gtg acc gtg ccc tcc agc agc ttg ggc acc       2367
Tyr Ser Leu Ser Ser Val Val Thr Val Pro Ser Ser Ser Leu Gly Thr
190                 195                 200                 205 cag acc tac atc tgc aac gtg aat cac aag ccc agc aac acc aag gtg       2415
Gln Thr Tyr Ile Cys Asn Val Asn His Lys Pro Ser Asn Thr Lys Val
                210                 215                 220 gac aag aaa gtt gaa cca aag agc tgc gac aag acc cac acg tgt ccc       2463
Asp Lys Lys Val Glu Pro Lys Ser Cys Asp Lys Thr His Thr Cys Pro
            225                 230                 235 ccc tgc cct gcc cct gaa ctg ctg gga ggc ccc agc gtg ttc ctg ttc       2511
Pro Cys Pro Ala Pro Glu Leu Leu Gly Gly Pro Ser Val Phe Leu Phe
        240                 245                 250 ccc cca aag ccc aag gac acc ctg atg atc agc cgg acc ccc gaa gtg       2559
Pro Pro Lys Pro Lys Asp Thr Leu Met Ile Ser Arg Thr Pro Glu Val
    255                 260                 265 acc tgc gtg gtg gtg gac gtg tcc cac gag gac cct gaa gtg aag ttt       2607
Thr Cys Val Val Val Asp Val Ser His Glu Asp Pro Glu Val Lys Phe
270                 275                 280                 285 aat tgg tac gtg gac ggc gtg gaa gtg cac aac gcc aag acc aag ccc       2655
Asn Trp Tyr Val Asp Gly Val Glu Val His Asn Ala Lys Thr Lys Pro
                290                 295                 300 aga gag gaa cag tac aac agc acc tac cgg gtg gtg tcc gtg ctg acc       2703
Arg Glu Glu Gln Tyr Asn Ser Thr Tyr Arg Val Val Ser Val Leu Thr
            305                 310                 315 gtg ctg cac cag gac tgg ctg aac ggc aaa gag tac aag tgc aag gtg       2751
Val Leu His Gln Asp Trp Leu Asn Gly Lys Glu Tyr Lys Cys Lys Val
```

|   |   |
|---|---|
| ```<br>                     320                 325                 330<br>tcc aac aag gcc ctg cct gcc ccc atc gag aaa acc atc agc aag gcc<br>Ser Asn Lys Ala Leu Pro Ala Pro Ile Glu Lys Thr Ile Ser Lys Ala<br>    335                 340                 345<br><br>aag ggc cag ccc cgc gag cct cag gtc tac aca ctg ccc ccc agc cgg<br>Lys Gly Gln Pro Arg Glu Pro Gln Val Tyr Thr Leu Pro Pro Ser Arg<br>350                 355                 360                 365<br><br>gaa gag atg acc aag aac cag gtg tcc ctg acc tgc ctg gtc aag ggc<br>Glu Glu Met Thr Lys Asn Gln Val Ser Leu Thr Cys Leu Val Lys Gly<br>                    370                 375                 380<br><br>ttc tac ccc agc gac atc gcc gtg gaa tgg gag agc aac ggc cag ccc<br>Phe Tyr Pro Ser Asp Ile Ala Val Glu Trp Glu Ser Asn Gly Gln Pro<br>                385                 390                 395<br><br>gag aac aac tac aag acc acc ccc cct gtg ctg gac agc gac ggc tca<br>Glu Asn Asn Tyr Lys Thr Thr Pro Pro Val Leu Asp Ser Asp Gly Ser<br>            400                 405                 410<br><br>ttc ttc ctg tat agc aag ctg acc gtg gac aag agc cgg tgg cag cag<br>Phe Phe Leu Tyr Ser Lys Leu Thr Val Asp Lys Ser Arg Trp Gln Gln<br>        415                 420                 425<br><br>ggc aac gtg ttc agc tgc agc gtg atg cac gag gcc ctg cac aac cac<br>Gly Asn Val Phe Ser Cys Ser Val Met His Glu Ala Leu His Asn His<br>430                 435                 440                 445<br><br>tac acc cag aag tcc ctg agc ctg agc ccc ggc agaaagcgga gagccccgt<br>Tyr Thr Gln Lys Ser Leu Ser Leu Ser Pro Gly<br>                    450                 455<br><br>gaagcagacc ctgaacttcg acctgctgaa gctggccggc gacgtggaaa gcaaccctgg<br><br>ccctatgtac agaatgcagc tgctgctgct gatcgccctg agcctggccc tggtgaccaa<br><br>cagc gat atc gtc atg acc cag agc cca gat agc ctg gcc gtg agc ctg<br>     Asp Ile Val Met Thr Gln Ser Pro Asp Ser Leu Ala Val Ser Leu<br>                    460                 465                 470<br><br>gga gag cgg gcc acc atc aac tgc aag agc agc cag agc gtg ctg tac<br>Gly Glu Arg Ala Thr Ile Asn Cys Lys Ser Ser Gln Ser Val Leu Tyr<br>                475                 480                 485<br><br>agc agc aac aac aag aac tac ctg gcc tgg tac cag cag aag cca gga<br>Ser Ser Asn Asn Lys Asn Tyr Leu Ala Trp Tyr Gln Gln Lys Pro Gly<br>            490                 495                 500<br><br>cag cca cca aag ctg ctg atc tac tgg gcc agc acc cgg gag agc gga<br>Gln Pro Pro Lys Leu Leu Ile Tyr Trp Ala Ser Thr Arg Glu Ser Gly<br>        505                 510                 515<br><br>gtg cca gat cgg ttc agc gga agc gga agc gga acc gat ttc acc ctg<br>Val Pro Asp Arg Phe Ser Gly Ser Gly Ser Gly Thr Asp Phe Thr Leu<br>520                 525                 530                 535<br><br>acc atc agc agc ctg cag gcc gag gat gtg gcc gtg tac tac tgc cag<br>Thr Ile Ser Ser Leu Gln Ala Glu Asp Val Ala Val Tyr Tyr Cys Gln<br>                    540                 545                 550<br><br>cag tac tac agc acc cca ctg acc ttc gga cag gga acc aag gtg gag<br>Gln Tyr Tyr Ser Thr Pro Leu Thr Phe Gly Gln Gly Thr Lys Val Glu<br>                555                 560                 565<br><br>atc aag cgt acg gtg gcc gcc cca agc gtg ttc atc ttc cca cca agc<br>Ile Lys Arg Thr Val Ala Ala Pro Ser Val Phe Ile Phe Pro Pro Ser<br>            570                 575                 580<br><br>gat gag cag ctg aag agc gga acc gcc agc gtg gtg tgc ctg ctg aac<br>Asp Glu Gln Leu Lys Ser Gly Thr Ala Ser Val Val Cys Leu Leu Asn<br>        585                 590                 595<br><br>aac ttc tac cca cgg gag gcc aag gtg cag tgg aag gtg gat aac gcc<br>Asn Phe Tyr Pro Arg Glu Ala Lys Val Gln Trp Lys Val Asp Asn Ala<br>600                 605                 610                 615<br><br>ctg cag agc gga aac agc cag gag agc gtg acc gag cag gat agc aag<br>``` | 2799<br><br><br><br>2847<br><br><br><br>2895<br><br><br><br>2943<br><br><br><br>2991<br><br><br><br>3039<br><br><br><br>3087<br><br><br><br>3140<br><br><br>3200<br><br>3260<br><br>3309<br><br><br><br>3357<br><br><br><br>3405<br><br><br><br>3453<br><br><br><br>3501<br><br><br><br>3549<br><br><br><br>3597<br><br><br><br>3645<br><br><br><br>3693<br><br><br><br>3741<br><br><br><br>3789 |

```
Leu Gln Ser Gly Asn Ser Gln Glu Ser Val Thr Glu Gln Asp Ser Lys
                620                 625                 630 gat agc acc tac agc ctg agc agc acc ctg acc ctg agc aag gcc gat    3837
Asp Ser Thr Tyr Ser Leu Ser Ser Thr Leu Thr Leu Ser Lys Ala Asp
                635                 640                 645 tac gag aag cac aag gtg tac gcc tgc gag gtg acc cac cag gga ctg    3885
Tyr Glu Lys His Lys Val Tyr Ala Cys Glu Val Thr His Gln Gly Leu
                650                 655                 660 agc agc cca gtg acc aag agc ttc aac cgc gga gag tgc tgataaagcg    3934
Ser Ser Pro Val Thr Lys Ser Phe Asn Arg Gly Glu Cys
                665                 670             675 gccgcggtac  tctagagtc  gacccgggcg  gcctcgagga  cggggtgaac  tacgcctgag    3994
gatccgatct  ttttccctct  gccaaaaatt  atggggacat  catgaagccc  cttgagcatc    4054
tgacttctgg  ctaataaagg  aaatttattt  tcattgcaat  agtgtgttgg  aattttttgt    4114
gtctctcact  cggaagcaat  tcgttgatct  gaatttcgac  cacccataat  acccattacc    4174
ctggtagata  gtagcatgg   cgggttaatc  attaactaca  aggaacccct  agtgatggag    4234
ttggccactc  cctctctgcg  cgctcgctcg  ctcactgagg  ccgggcgacc  aaaggtcgcc    4294
cgacgcccgg  gctttgcccg  gcggcctca   gtgagcgagc  gagcgcgcag  ccttaattaa    4354
cctaattcac  tggccgtcgt  tttacaacgt  cgtgactggg  aaaaccctgg  cgttacccaa    4414
cttaatcgcc  ttgcagcaca  tccccctttc  gccagctggc  gtaatagcga  agaggcccgc    4474
accgatcgcc  cttcccaaca  gttgcgcagc  ctgaatggcg  aatgggacgc  gccctgtagc    4534
ggcgcattaa  gcgcggcggg  tgtggtggtt  acgcgcagcg  tgaccgctac  acttgccagc    4594
gccctagcgc  ccgctccttt  cgctttcttc  ccttcctttc  tcgccacgtt  cgccggcttt    4654
ccccgtcaag  ctctaaatcg  gggctccct   ttagggttcc  gatttagtgc  tttacggcac    4714
ctcgacccca  aaaacttga   ttaggtgat   ggttcacgta  gtgggccatc  gccctgatag    4774
acggttttc   gccctttgac  gttggagtcc  acgttcttta  atagtggact  cttgttccaa    4834
actggaacaa  cactcaaccc  tatctcggtc  tattcttttg  atttataagg  gattttgccg    4894
atttcggcct  attggttaaa  aaatgagctg  atttaacaaa  aatttaacgc  gaattttaac    4954
aaaatcatgt  gagcaaaagg  ccagcaaaag  gccaggaacc  gtaaaaaggc  cgcgttgctg    5014
gcgtttttcc  ataggctccg  cccccctgac  gagcatcaca  aaaatcgacg  ctcaagtcag    5074
aggtggcgaa  acccgacagg  actataaaga  taccaggcgt  ttccccctgg  aagctccctc    5134
gtgcgctctc  ctgttccgac  cctgccgctt  accggatacc  tgtccgcctt  tctcccttcg    5194
ggaagcgtgg  cgctttctca  tagctcacgc  tgtaggtatc  tcagttcggt  gtaggtcgtt    5254
cgctccaagc  tgggctgtgt  gcacgaaccc  cccgttcagc  ccgaccgctg  cgccttatcc    5314
ggtaactatc  gtcttgagtc  aacccggta   agacacgact  tatcgccact  ggcagcagcc    5374
actggtaaca  ggattagcag  agcgaggtat  gtaggcggtg  ctacagagtt  cttgaagtgg    5434
tggcctaact  acggctacac  tagaagaaca  gtatttggta  tctgcgctct  gctgaagcca    5494
gttaccttcg  gaaaaagagt  tggtagctct  tgatccggca  acaaaccac   cgctggtagc    5554
ggtggttttt  ttgtttgcaa  gcagcagatt  acgcgcagaa  aaaaggatc   tcaagaagat    5614
cctttgatct  tttctacggg  gtctgacgct  cagtggaacg  aaaactcacg  ttaagggatt    5674
ttggtcatga  gattatcaaa  aaggatcttc  acctagatcc  ttttgatcct  tccggcgttca   5734
gcctgtgcca  cagccgacag  gatggtgacc  accatttgcc  ccatatcacc  gtcggtactg    5794
atcccgtcgt  caataaaccg  aaccgctaca  ccctgagcat  caaactcttt  tatcagttgg    5854
```

```
atcatgtcgg cggtgtcgcg gccaagacgg tcgagcttct tcaccagaat gacatcacct      5914
tcctccacct tcatcctcag caaatccagc ccttcccgat ctgttgaact gccggatgcc      5974
ttgtcggtaa agatgcggtt agcttttacc cctgcatctt tgagcgctga ggtctgcctc      6034
gtgaagaagg tgttgctgac tcataccagg cctgaatcgc cccatcatcc agccagaaag      6094
tgagggagcc acggttgatg agagctttgt tgtaggtgga ccagttggtg attttgaact      6154
tttgctttgc cacggaacgg tctgcgttgt cgggaagatg cgtgatctga tccttcaact      6214
cagcaaaagt tcgatttatt caacaaagcc gccgtcccgt caagtcagcg taatgctctg      6274
ccagtgttac aaccaattaa ccaattctga ttagaaaaac tcatcgagca tcaaatgaaa      6334
ctgcaattta ttcatatcag gattatcaat accatatttt tgaaaagcc gtttctgtaa       6394
tgaaggagaa aactcaccga ggcagttcca taggatggca agatcctggt atcggtctgc      6454
gattccgact cgtccaacat caatacaacc tattaatttc ccctcgtcaa aaataaggtt      6514
atcaagtgag aaatcaccat gagtgacgac tgaatccggt gagaatggca aaagcttatg      6574
catttctttc cagacttgtt caacaggcca gccattacgc tcgtcatcaa aatcactcgc      6634
atcaaccaaa ccgttattca ttcgtgattg cgcctgagcg agacgaaata cgcgatcgct      6694
gttaaaagga caattacaaa caggaatcga atgcaaccgg cgcaggaaca ctgccagcgc      6754
atcaacaata ttttcacctg aatcaggata ttcttctaat acctggaatg ctgttttccc      6814
ggggatcgca gtggtgagta accatgcatc atcaggagta cggataaaat gcttgatggt      6874
cggaagaggc ataaattccg tcagccagtt tagtctgacc atctcatctg taacatcatt      6934
ggcaacgcta cctttgccat gtttcagaaa caactctggc gcatcgggct cccatacaa      6994
tcgatagatt gtcgcacctg attgcccgac attatcgcga gcccatttat acccatataa      7054
atcagcatcc atgttggaat ttaatcgcgg cctcgagcaa gacgtttccc gttgaatatg      7114
gctcataaca ccccttgtat tactgtttat gtaagcagac agttttattg ttcatgatga      7174
tatatttta tcttgtgcaa tgtaacatca gagattttga gacaccatgt tctttcctgc       7234
gttatcccct gattctgtgg ataaccgtat taccgccttt gagtgagctg ataccgctcg      7294
ccgcagccga acgaccgagc gcagcgagtc agtgagcgag gaagcggaag agcgcccaat      7354
acgcaaaccg cctctccccg cgcgttggcc gattcattaa tgcagctggc acgacaggtt      7414
tcccgactgg aaagcgggca gtgagcgcaa cgcaattaat gtgagttagc tcactcatta      7474
ggcaccccag gctttacact ttatgcttcc ggctcgtatg ttgtgtggaa ttgtgagcgg      7534
ataacaattt cacacaggaa acagctatga ccatgattac gccagattta attaaggcct      7594
taattaggct gcgcgctcgc tcgctcactg aggccgcccg gcaaagccc gggcgtcggg       7654
cgacctttgg tcgcccggcc tcagtgagcg agcgagcgcg cagagaggga gtggccaact      7714
ccatcactag gggttccttg tagttaatga ttaacccgcc atgctactta tctaccaggg      7774
taatggggat cctctagaac tatagctagt cgacattgat tattgactag ttattaatag      7834
taatcaatta cggggtcatt agttcatagc ccatatatgg agttccgcgt tacataactt      7894
acggt                                                                  7899
```

<210> SEQ ID NO 9
<211> LENGTH: 127
<212> TYPE: PRT
<213> ORGANISM: Artificial Sequence
<220> FEATURE:
<223> OTHER INFORMATION: Synthetic Construct

<400> SEQUENCE: 9

Glu Val Gln Leu Val Glu Thr Gly Gly Gly Leu Val Gln Pro Gly Arg
1               5                   10                  15

Ser Leu Arg Leu Ser Cys Ala Ala Ser Gly Phe Ser Phe Asp Glu Tyr
                20                  25                  30

Thr Met His Trp Val Arg Gln Ala Pro Gly Lys Gly Leu Glu Trp Val
            35                  40                  45

Ala Gly Ile Asn Trp Lys Gly Asn Phe Met Gly Tyr Ala Asp Ser Val
        50                  55                  60

Gln Gly Arg Phe Thr Ile Ser Arg Asp Asn Gly Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Arg Leu Glu Ser Ser Ala Met Asp Ile Leu Glu Gly Gly
            100                 105                 110

Thr Phe Asp Ile Trp Gly Gln Gly Thr Met Val Thr Val Ser Ser
        115                 120                 125

<210> SEQ ID NO 10
<211> LENGTH: 107
<212> TYPE: PRT
<213> ORGANISM: Artificial Sequence
<220> FEATURE:
<223> OTHER INFORMATION: Synthetic Construct

<400> SEQUENCE: 10

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His
            100                 105

<210> SEQ ID NO 11
<211> LENGTH: 222
<212> TYPE: PRT
<213> ORGANISM: Artificial Sequence
<220> FEATURE:
<223> OTHER INFORMATION: Synthetic Construct

<400> SEQUENCE: 11

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Asp Pro Glu
            35                  40                  45

Val Lys Phe Asn Trp Tyr Val Asp Gly Val Glu Val His Asn Ala Lys
        50                  55                  60

Thr Lys Pro Arg Glu Glu Gln Tyr Asn Ser Thr Tyr Arg Val Val Ser

```
                65                  70                  75                  80
Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
            115                 120                 125

Pro Ser Arg Glu Glu Met Thr Lys Asn Gln Val Ser Leu Thr Cys Leu
        130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly
    210                 215                 220

<210> SEQ ID NO 12
<211> LENGTH: 113
<212> TYPE: PRT
<213> ORGANISM: Artificial Sequence
<220> FEATURE:
<223> OTHER INFORMATION: Synthetic Construct

<400> SEQUENCE: 12

Asp Ile Val Met Thr Gln Ser Pro Asp Ser Leu Ala Val Ser Leu Gly
1               5                  10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gln Gly Thr Lys Val Glu Ile
            100                 105                 110

Lys

<210> SEQ ID NO 13
<211> LENGTH: 107
<212> TYPE: PRT
<213> ORGANISM: Artificial Sequence
<220> FEATURE:
<223> OTHER INFORMATION: Synthetic Construct

<400> SEQUENCE: 13

Arg Thr Val Ala Ala Pro Ser Val Phe Ile Phe Pro Pro Ser Asp Glu
1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
```

```
                35                  40                  45
Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 14
<211> LENGTH: 2238
<212> TYPE: DNA
<213> ORGANISM: Artificial Sequence
<220> FEATURE:
<223> OTHER INFORMATION: include leader-entire heavy chain-furin-F2A
      linker-leader-entire light chain

<400> SEQUENCE: 14

| | |
|---|---|
| atgtatagaa tgcagttgtt gtcgtgcatc gcactctctc tcgcgcttgt cacaaactcc | 60 |
| caggttcaac tggtggagtc agggggggggg gtggtgcagc cggggcggag tctgaggctg | 120 |
| agctgcgccg cgagtggatt cacgttttcg acatacgcga tgcactgggt ccgccaggcc | 180 |
| cccggaaagg gtctgaatgg gtggccgtga ttagttacg atgcgaatta caagtattac | 240 |
| gccgactcag tgaagggccg gttcacgata tcacgggaca actctaaaaa caccctgtac | 300 |
| cttcaaatga actcactgcg ggcggaggat accgctgtct actattgtgc aaaggactct | 360 |
| cagctgcgat ccttgctgta tttcgagtgg ctgagccagg gttactttga ctactgggga | 420 |
| cagggcaccc tcgtgaccgt gtcctctgcc tcaacgaagg ggccgtccgt ttttccactg | 480 |
| gctccgtcaa gcaaatcaac tagcggcggg actgcagcat gggggtgcct agtgaaggac | 540 |
| tatttccccg agcctgtgac ggtgtcgtgg aactcgggag cactgacgtc cggggtgcac | 600 |
| acattccccg cggtgctgca gagctccggg ctgtattcgt tgagcagtgt cgtgactgtg | 660 |
| cccagctcga gtctggggac tcagacatac atctgcaacg tgaaccataa gccatctaat | 720 |
| acgaaggtgg acaagaaggt cgagccaaag tcgtgcgaca gacccatac atgcccacca | 780 |
| tgtcccgcgc cggagctgtt gggcgggccc tcagtgttcc tgttcccgcc taagccaaag | 840 |
| gacacgctga tgattagccg gacccctgaa gtgacatgcg tggtggtgga tgtatcccac | 900 |
| gaggaacccg acgtgaagtt caattggtac gtggacgggg tggaggtgca caatgctaaa | 960 |
| accaaacccc gggaggagca gtacaactct acgtaccggg tggtgtccgt actgaccgtg | 1020 |
| ctacaccagg actggctgaa cgggaaggag tacaagtgta agtgtcgaa caaggctctg | 1080 |
| ccagccccca ttgagaaaac catatcaaag gctaagggcc agcccaggga gcctcaagtg | 1140 |
| tacacgctgc cgccgagccg cgacgagctg acaaagaacc aggtttcgct gacgtgcctt | 1200 |
| gtcaagggat tctacccaag cgacatcgca gtggagtggg agtctaacgg acagccagag | 1260 |
| aacaactaca aaaccacgcc gcccgtgctg gattcggacg gctccttctt tctgtactct | 1320 |
| aagctgacgg tggacaagtc cagatggcag caggggaacg tattcagctg cagtgtgatg | 1380 |
| cacgaggcct tgcacaatca ctatacgcag aagagtctgt ccttgtcacc gggaaggaag | 1440 |
| cgcagggccc tgtgaagca gacactgaac ttcgacttac tgaagttggc cggcgacgtg | 1500 |
| gagtcgaacc ctgggccgat gtaccggatg cagctcctgc tcctgatcgc gctgtcgctg | 1560 |
| gctttggtta ccaactccga cattgtgatg acgcaaagcc ctgactccct ggcggtgtct | 1620 |

| | |
|---|---|
| ctgggggaga gggccactat caactgcaaa tccagccaga gcgtgctgta ctcgtcaaac | 1680 |
| aacaagaatt acttagcctg gtaccagcag aagccaggac agccgccaaa gttgctgatc | 1740 |
| tattgggcct ctacgcggga gtcgggagtg ccagataggt tcagcgggag tgggagcggt | 1800 |
| acagacttca ccctgaccat aagcagcttg caggcgagg atgtggcagt gtactactgc | 1860 |
| cagcagtact actcgacacc cttgacattc ggccagggga ccaaagtgga gatcaagcgt | 1920 |
| accgtagccg ccccgagcgt gttcatcttt ccaccgtccg acgaacagct gaagtcgggg | 1980 |
| accgccagcg tcgtgtgttt gctgaacaac ttctaccccc gggaagcaaa ggtccagtgg | 2040 |
| aaggtcgaca acgcattgca gtcggggaac tcccaggaaa gcgtgactga gcaggattcc | 2100 |
| aaggacagta catactcact gtcgtcaact ctcacactgt ccaaggcgga ctacgagaag | 2160 |
| cacaaggtgt acgcctgcga ggttacgcac caggggctgt cctctcccgt gacgaaaagc | 2220 |
| ttcaataggg gggagtgc | 2238 |

<210> SEQ ID NO 15
<211> LENGTH: 2238
<212> TYPE: DNA
<213> ORGANISM: Artificial Sequence
<220> FEATURE:
<223> OTHER INFORMATION: 1F16 1leader-entire heavy chain-furin-F2A
    linker-leader-entire light chain

<400> SEQUENCE: 15

| | |
|---|---|
| atgtatagaa tgcaactgct ctcctgtatc gcattgtctc tggctctcgt gacgaattcc | 60 |
| caagtgcaat tggtggagtc tgggggcggc gttgtgcagc ccgggcggag cctcaggttg | 120 |
| tcgtgtgctg ccagcggctt tacgttttca acctatgcca tgcattgggt tcgacaggca | 180 |
| cccggcaaag gcctggaatg ggtcgccgtg attagctatg acgctaacta caagtattat | 240 |
| gctgattccg tgaagggccg cttttacaatc agtcgcgata attccaagaa caccctgtat | 300 |
| ctgcaaatga acagcctgag ggctgaggac acagccgtgt attactgtgc aaaggacagc | 360 |
| cagttgcgga gcctcctgta tttcgagtgg ctgagccagg gctattttga ttattgggcc | 420 |
| cagggcactc tggtcaccgt tagctctgct agtaccaaag gcccaagcgt ctttccactc | 480 |
| gctccatcgt ccaagtctac ctctggggga accgctgctc tgggctgcct agtgaaagac | 540 |
| tatttccccg aaccggttac agtctcctgg aattctggcg cgctgacgag cggtgtacat | 600 |
| acttttccgg cggtgctcca gtcctccggc ctgtatagtc tgagttccgt agtcaccgta | 660 |
| ccatcatcta gtctgggaac ccaaacatat atttgcaacg tgaaccataa gccttccaac | 720 |
| actaaggtcg ataagaaggt tgaacccaaa agctgtgaca gacccacac atgtcctcct | 780 |
| tgtcccgcac cggagttgtt gggcggccct tccgtgtttc tgtttccgcc caagcctaag | 840 |
| gatacactga tgattagcag aaccccagaa gtcacttgcg tggtggtgga tgtgtcccat | 900 |
| gaggaaccag acgtgaagtt taattggtat gtagacgggg tggaggtaca caacgcaaag | 960 |
| accaagccga gggaggagca gtacaacagc acctatcgcg tggtgtcagt gttaacggta | 1020 |
| ctgcaccaag actggctgaa tgggaaggag tataagtgta agtgtcaaa caaggctctg | 1080 |
| ccagctccaa tagaaaagac tattagcaag gctaagggcc agccgaggga accccaggtc | 1140 |
| tacaccctgc cgccgagccg cgacgaactg accaaaaacc aggtttccct gacatgtctg | 1200 |
| gtcaagggtt tctacccttc cgacatcgct gtagaatggg agtccaatgg tcaaccggaa | 1260 |
| aacaactata agactacgcc ccctgtactg gacagcgacg gcagtttctt cttgtattca | 1320 |
| aagcttacag ttgacaagtc aagatggcag cagggcaatg tctttagctg ttccgtgatg | 1380 |

| | |
|---|---|
| catgaggctt tacataacca ctacactcaa aagagtctgt cgttgtctcc tggccggaag | 1440 |
| agaagggcac cagttaagca gaccctgaac tttgaccttc tcaagttggc tggcgatgtg | 1500 |
| gaaagcaacc ccggcccaat gtaccggatg cagctgctgc ttctgattgc cctgtcactg | 1560 |
| gctctagtta ccaactccga tatagtgatg actcagtctc ccgattccct ggctgtatct | 1620 |
| ttgggagagc gagccacgat caattgcaaa tccagccaaa gcgtgctgta tagctctaac | 1680 |
| aacaagaatt atctggcttg gtaccagcaa aaacctggcc aacccccaaa gctgttgatc | 1740 |
| tattgggctt ccacccgtga atccggcgtg cccgaccggt ttagcggttc cggctctgga | 1800 |
| accgatttta ctctgacaat ttccagcctg caagctgaag atgtggccgt ctactattgt | 1860 |
| caacagtatt actctacacc actaacattt gggcagggca cgaaagtaga gattaagagg | 1920 |
| actgtggctg ccccatccgt gtttatcttt cctccctccg acgagcagct gaagagtggc | 1980 |
| acggctagtg ttgtttgtct gttgaacaat ttctatcccc gggaggccaa ggttcagtgg | 2040 |
| aaagtagaca acgcattgca gtccgggaat agccaggaga gtgtgacaga acaggactct | 2100 |
| aaggacagca cttattccct gtcgagcacc ctgaccttga gcaaggccga ctacgaaaag | 2160 |
| cataaggtct acgcctgcga agtgacacat cagggcctga gttcacccgt gacaagagc | 2220 |
| tttaacaggg gcgaatgt | 2238 |

<210> SEQ ID NO 16
<211> LENGTH: 2238
<212> TYPE: DNA
<213> ORGANISM: Artificial Sequence
<220> FEATURE:
<223> OTHER INFORMATION: F16 26

<400> SEQUENCE: 16

| | |
|---|---|
| atgtaccgca tgcagctctt atcgtgtatt gccctgagtc ttgccctcgt gacaaatagc | 60 |
| caggtccagc tcgtggaatc tggcggtggc gtggtgcagc ccggaagaag cttaaggctg | 120 |
| tcatgcgccg ccagcggctt tacgtttagt acttatgcaa tgcactgggt ccgacaggct | 180 |
| cccgggaagg gcttggaatg ggtggccgtg attagctacg acgctaacta caagtattac | 240 |
| gccgactctg tcaagggaag attcacgatc tctcgtgaca attcaaagaa taccttgtac | 300 |
| cttcaaatga acagcctgcg ggctgaagat accgccgtat actactgcgc taaggactca | 360 |
| cagctgcgct ctcttctcta cttcgaatgg ctaagccagg ttactttga ctactgggga | 420 |
| caggggaccc ttgttaccgt gtctagtgcc agcaccaagg gtcccagcgt gttccccctg | 480 |
| gctccaagct ctaaatcaac ctcgggtggt actgcagcac taggctgcct tgtgaaggac | 540 |
| tacttccccg agccagtaac cgtgtcctgg aattctggtg ctctaacctc cggagtgcat | 600 |
| accttcctg ctgtgttgca gtcaagcggg ctgtacagtc tgtcaagtgt cgtgaccgtg | 660 |
| ccttcatctt ccctcggaac tcagacctac atatgtaacg tgaatcacaa gccgtccaat | 720 |
| accaaagtgg acaaaaaggt cgaacccaag tcgtgcgaca agacccatac gtgccccacca | 780 |
| tgccccgctc ccgagctatt gggtggacct tcagtgttct tattccctcc aaaacccaag | 840 |
| gataccttga tgatttcacg gacccctgaa gtgacctgtg tggtggttga cgtgtcacat | 900 |
| gaggaacccg atgtgaagtt taattggtat gtggacggct ggaggttca taacgctaaa | 960 |
| accaagccca gggaagaaca gtacaacagt acttaccgcg tggtgtctgt gcttaccgtg | 1020 |
| ctgcatcagg actggctgaa tggaaaggag tacaagtgca aggtgtccaa taaggctttg | 1080 |
| cccgcgccta tcgaaaagac catatctaag gccaagggcc agccccgaga gcctcaggtc | 1140 |
| tacacactcc ctccatcccg cgacgagctg acaaagaatc aagtgtctct cacctgtctt | 1200 |

```
gtgaagggtt tctatccctc tgacatcgcc gtggagtggg agtcgaacgg ccagcccgaa     1260
aacaactaca agaccacccc tcccgtgctg gactcagacg gttcgttctt tctgtattcc     1320
aagctgaccg tcgacaaaag cagatggcag caggggaacg tcttttcatg ctccgtgatg     1380
cacgaagcac tgcacaatca ctatacccag aaatcactgt ctctgtctcc tggtcggaaa     1440
cgcagggcgc ctgtgaagca gactctcaat ttcgaccttc ttaagctcgc tggagatgtg     1500
gagagcaacc ccgggccaat gtacaggatg cagcttctac tgctgatcgc actgtctctc     1560
gcactcgtga cgaattccga catagtgatg acccagtccc ctgactcact cgctgtgtcc     1620
ctcggtgaac gcgccaccat caactgcaag agttcacagt cagtgttata cagttctaac     1680
aataagaatt acctggcctg gtaccaacag aagcccggtc aaccgcccaa gttacttatc     1740 tatttgggcct ccacccgtga agcggagtg cccgacaggt ttagcggtag tggtagtggt     1800
accgacttta ccctgactat cagtagccta caggcagagg atgtggcggt gtactactgc     1860
cagcagtact actcaactcc attgacattc ggccagggta ccaaagtcga gatcaagcgc     1920
actgtggccg ccccgagcgt gtttattttt ccaccgtctg atgagcagct taagtcaggc     1980
accgctagtg tagtgtgcct gctgaacaac ttttatcctc gggaggccaa agtgcagtgg     2040
aaggtcgaca acgcacttca gagtggcaat agtcaggaat ccgtgacaga acaggattca     2100
aaggactcaa cctactcttt gagttcaacc cttaccctgt cgaaggcaga ctacgagaag     2160
cacaaggttt acgcctgcga agtgacccat cagggcctca gcagcccgt aaccaagtcc     2220 tttaatcggg gggaatgc                                                    2238

<210> SEQ ID NO 17
<211> LENGTH: 2238
<212> TYPE: DNA
<213> ORGANISM: Artificial Sequence
<220> FEATURE:
<223> OTHER INFORMATION: F16 28

<400> SEQUENCE: 17
atgtaccgaa tgcagcttct ttcatgtatc gcactttccc ttgcccttgt tacaaatagt       60
caagtgcagt tggtggagag cggcggcggc gtagtgcagc ccggccgatc tctccgacta      120
tcctgtgccg cgagcggctt taccttctca acctatgcta tgcattgggt cagacaggcc      180
cctggaaagg gtcttgaatg ggtggccgtg atttcctatg acgctaacta caagtattac      240
gcagactctg tgaagggccg tttcacaatt agcagggaca attccaagaa tactctttat      300
ctgcaaatga atagcttaag agccgaggac accgctgtgt actattgtgc aaaggatagt      360
cagctgagga gcctactcta cttcgagtgg ttgagccagg gctattttga ttattggggc      420
cagggcaccc ttgtgaccgt gtcaagtgcc agtaccaagg gccttccgt gttccctctc      480 gcaccctcat ctaagtcaac tagtggcggc acggctgccc ttggttgtct cgtgaaggac      540
tatttccctg agcctgtcac tgtgtcctgg aattctggcg cacttacctc tggcgtgcat      600
accttccccg cggtgcttca gagtagtggt ctttattctc tgagtagcgt ggtcaccgtg      660
cctagttcta gtttgggtac tcagacttat atttgtaacg tgaaccacaa gcccagcaac      720
acaaaagtgg acaagaaggt cgaacctaaa tcttgcgata gacccacac atgccctcct      780 tgccctgcac ctgagctact gggcggtcct agcgtgttcc ttttcccacc caagccaaag      840
gacaccctga tgatatcccg gacgccagaa gttacatgcg tggtggtgga cgtatctcat      900
gaggagcctg atgtgaagtt caattggtac gtggacggcg tggaggtgca caatgctaag      960
```

```
acaaagccta gagaggagca gtacaatagc acctatagag tggtttcagt gcttactgtg    1020
ctgcaccagg actggcttaa tgggaaggag tataagtgca aagtctccaa taaggctctg    1080
cccgcaccca tcgaaaagac aattagcaaa gccaagggcc agcctcgaga gcctcaggtc    1140
tatacactgc cacctagccg ggacgagctg actaagaatc aggtttcgct cacgtgtcta    1200
gtgaagggct tttacccttc cgacattgct gtggagtggg agtctaatgg ccagcccgag    1260
aacaattaca agaccacgcc accggtgttg gactctgacg ggagcttctt cctatactct    1320
aagcttactg tggacaagtc gagatggcag cagggaaacg tgttctcctg ttctgtgatg    1380
catgaggccc tgcacaacca ttatacccag aagtcgctct ccctgagccc tggcagaaaa    1440
agacgcgcgc ctgtgaagca gacacttaac tttgatcttc tgaagctcgc cggcgacgtc    1500
gagagtaatc ctggcccaat gtataggatg cagctgttac ttctgatcgc cttatctctt    1560
gctcttgtga cgaactcaga catagtgatg actcagtccc ccgattctct tgccgtgtct    1620
ctcggggagc gggccacgat caattgcaaa tcaagtcaat cagtgctgta ctctagtaac    1680
aataagaact acctagcctg gtatcagcaa aagcctggcc agcctcctaa gctccttatc    1740
tattgggcgt ctaccagaga gtccggagtg cccgatagat tcagcggatc agggtctggg    1800
accgatttta ccctcacaat tagtagcctt caggcggagg acgtggccgt gtattactgc    1860
cagcagtact actccacgcc tctgacattt gggcagggca ccaaggtcga gatcaaaaga    1920
acagtagcag ccccgtcagt gttcattttt cctccatctg acgaacagct caaaagcggg    1980
actgcgtccg tagtgtgctt gctcaacaac ttttaccccac gagaggccaa ggtccagtgg    2040 aaaagtggata atgcacttca gagcggcaac agtcaggagt ccgtgacgga gcaggattct    2100
aaggactcca catatagtct cagtagtact ttaacgttgt cgaaggccga ttacgagaag    2160
cataaagtgt acgcttgtga agtgacccac cagggcttat caagccctgt gacaaagtcc    2220
ttcaatcgcg gggagtgt                                                   2238

<210> SEQ ID NO 18
<211> LENGTH: 2238
<212> TYPE: DNA
<213> ORGANISM: Artificial Sequence
<220> FEATURE:
<223> OTHER INFORMATION: F16 30 cDNA

<400> SEQUENCE: 18
atgtatagaa tgcaactcct gtcatgtatc gcactgtctc tcgcactcgt cacaaacagc      60
caggtccagc tagtggagtc cggggggggt gtagtgcaac tgggagatc attaaggctg     120 agctgtgccg cttctgggtt cacattttca acatacgcta tgcactgggt ccgtcaggca     180
cctggaaaag gattgaatg ggtggctgtg atctcctatg acgctaacta taagtattat     240
gccgatagcg tgaaggggcg gtttactatc tcgagagata actccaagaa cacgctttat     300
cttcaaatga attccctccg cgccgaggat actgccgtgt actattgtgc taaggatagt     360
cagctgcgaa gccttctata ctttgagtgg ttgagccagg gtattttga ctactgggga     420 caggggacct tagtgaccgt tagcagcgct agtacaaagg gaccttctgt tttcccctctt     480 gcccccctcct ctaaatccac tagcggcggg acagctgctc taggatgcct tgtcaaggat     540
tactttcccg agcctgttac agtctcctgg aactccggcg ctcttacatc cggggtgcac     600
acttttcctg cggtcctcca aagctccggg ctttatagtt tgagtagcgt cgtgacagtg     660
ccttcgagtt ctctggggac acaaacatac atctgtaatg tcaaccacaa gcccagtaac     720
acaaaggttg acaagaaagt ggagccaaaa agttgtgaca agacacacac atgtcctccc     780
```

```
tgccctgccc ctgaattgct cggagggcca tccgtgtttc ttttccccc aaaacccaag      840 gatactctca tgatttcccg aaccctgag gtcacatgcg tggtcgtcga tgtcagccat      900
gaggaaccag acgtgaagtt caattggtac gtagatgggg tagaggtgca caatgccaaa    960
accaagcctc gggaggaaca gtataacagc acatacagag ttgtgtcagt gctcaccgtg   1020
ctgcaccagg attggctgaa tggcaaagag tataagtgca agtctccaa caaggccctt    1080 cctgctccta tcgaaaagac aatatcaaag gccaagggcc agccacgaga gcctcaagtc   1140
tacactcttc ccccatcgag agatgaactt acgaaaaacc aggtttcact cacatgcctc   1200
gtgaaaggct tttacccttc tgatattgct gtggaatggg agtcaaatgg ccagcctgaa   1260
aacaactata agacaacgcc cccagtcctt gatagcgacg ggtccttttt cctgtattcg   1320
aagctgaccg tggataagtc aagatggcag cagggcaacg tgttctcatg ttccgtcatg   1380
cacgaggcgc ttcataatca ttatacacag aaaagcctga gtcttagccc tgggcgaaaa   1440
cgaagggctc ccgtgaaaca gacactgaat tttgatcttc ttaagcttgc cggggatgtc   1500
gaatcaaacc ctgggcctat gtatcggatg cagctacttc tacttattgc actttccctg   1560
gcattagtaa caaattcaga tatcgtgatg acacagtcgc ctgatagtct cgctgtgtct   1620
cttggggaga gggccaccat taactgcaag agctcacaga gtgtgctgta ctcaagcaac   1680
aacaagaact atcttgcttg gtatcagcag aagcctgggc agcctcccaa gctcctcata   1740
tactgggctt caacaagaga atccggtgta cctgatcgat tttctggctc ggggtcgggg   1800
acagatttca ccttaactat ctctagcctg caagctgagg acgtggctgt ctattactgt   1860
cagcagtact actccactcc gctcacgttt ggccagggga caaaagtgga aatcaagaga   1920
actgttgctg ctccatccgt ctttatattt ccgccttctg acgaacagct caagagtggt   1980
acagcatccg tggttgcct gctgaacaac ttctacccac gcgaagctaa agtgcagtgg   2040
aaggttgata atgctctgca atcggggaat agccaggaaa gcgttacaga acaggattct   2100
aaggattcga catactccct ttcatctaca cttacattga gcaaggctga ctatgagaaa   2160
cacaaggtct acgcttgcga agtcacacat caggggcttt ctagccctgt cacaaagagc   2220
tttaacagag gagaatgt                                                 2238
```

<210> SEQ ID NO 19
<211> LENGTH: 2238
<212> TYPE: DNA
<213> ORGANISM: Artificial Sequence
<220> FEATURE:
<223> OTHER INFORMATION: F16 35 cDNA

<400> SEQUENCE: 19

```
atgtatcgga tgcaactttt gtcctgcatt gccctatctc tcgccctggt taccaacagt     60
caggttcagc ttgttgaaag cggcggtggc gtcgtccaac ctggtcgctc attgcggctg    120
agctgcgccg cttccggctt tactttctca acttacgcca tgcattgggt tagacaagcc    180
cctggcaaag gcttggaatg ggttgccgtt attagctatg acgcgaacta caagtactat    240
gctgattccg taaaggggcg cttcactatt tcacgagaca actccaaaaa caccctatac    300
cttcaaatga actcattacg ggctgaggac accgcagttt actattgcgc aaaggactcg    360
cagctccgga gctcctccta ttttgaatgg ctgtcccaag atatttcga ctactggggc    420 cagggtacac tggttaccgt gtcatccgca agcaccaaag gcccctctgt atttcctctc    480
gctccgtcgt ccaagtcaac ctcaggcggc accgctgcac tgggctgcct ggtcaaggac    540
```

```
tatttccccg aacccgtgac cgtttcctgg aacagtggtg ctctgacatc tggggtccat      600
acctttcccg ccgtgctcca atcaagtgga ctgtatagcc tctcgagtgt tgtaaccgtg      660
ccttcttcat cgctcggtac ccaaacctac atttgtaacg tcaatcacaa gcccagcaac      720
accaaagtcg ataagaaggt tgaacctaag tcctgtgata agacgcacac gtgcccaccc      780
tgtcccgctc ccgaactgtt aggcggcccc tctgtgtttc tgtttccccc taaaccaaag      840
gacaccttga tgattagcag gacacccgag gttacctgtg tcgttgttga cgtgtcgcat      900
gaggaacccg acgtaaagtt caattggtat gtagacgggg ttgaagtgca aacgccaag       960 accaaacccc gggaggaaca gtacaacagt acctatcggg ttgttagcgt tttgacggtc     1020
ctgcatcaag actggctgaa cggaaaggag tacaaatgca aagtgtcgaa caaggccctg     1080
cccgcaccta tcgaaaagac catcagcaag gctaagggac agcctagaga gccccaagtt     1140
tataccttgc ccccgtcccg ggatgaacta accaagaatc aagtttcgct gacctgtcta     1200
gtcaaaggct tttaccccctc cgacattgct gtggagtggg aaagcaatgg gcaacccgag     1260
aacaactata agactactcc acccgttctg gactctgacg gatccttttt cctgtactcg     1320
aaattgacag ttgacaagag ccggtggcag cagggcaacg tgttctcgtg ttccgttatg     1380
catgaggcac tacacaacca ctacacccag aagtcactgt cgcttagccc cggaaggaag     1440
aggagggccc ctgtgaagca aaccctgaac ttcgacctct tgaaattagc cggcgatgta     1500
gaatccaatc ccgggcccat gtataggatg caactgctgt tgctgattgc actgtcactg     1560
gcattagtta ctaattctga cattgttatg acccagtcgc cggactctct cgctgtctcg     1620
ctgggcgaaa gagccaccat taactgtaaa agctcgcagt cagtgctgta ctcctctaac     1680
aacaagaact atcttgcttg gtatcagcaa aaacccggcc agccccaaa gctgctgata      1740 tactgggcca gcaccaggga agcggcgtt cccgaccgtt ttagtggctc cggcagtggt     1800
accgacttta ccctgaccat ctcgtcactc aagccgaag atgtcgctgt gtactattgc     1860
cagcagtact attccacccc actgacgttt ggacaaggga ccaaagtgga gatcaagcgc     1920
acagtagccg cgccctcggt ctttatcttt ccccccctcgg acgaacaact caagtctggc     1980
accgcttccg ttgtttgtct gttgaacaac ttctatcccc gggaagctaa ggttcagtgg     2040
aaggttgaca acgcgctgca agcgggaac agtcaggaat cagtcaccga acaggactct     2100
aaggacagca cctatagcct gagcagcact ttgaccctgt cgaaggcgga ttacgaaaag    2160
cataaagtct atgcatgcga agtgacccac caagggctgt cctccccgt gaccaaaagc     2220 ttcaataggg gcgaatgt                                                   2238
```

<210> SEQ ID NO 20  
<211> LENGTH: 2238  
<212> TYPE: DNA  
<213> ORGANISM: Artificial Sequence  
<220> FEATURE:  
<223> OTHER INFORMATION: an engineered F16 DNA sequence

<400> SEQUENCE: 20

```
atgtatcgaa tgcagctctt gtcatgtatc gctctctcac tcgctctcgt cacgaacagt       60
caggttcagt tagtggagag tggaggggga gtagtgcagc caggaagaag cttgagacta     120
tcttgcgccg cttccggttt cacatttttcc acatatgcta tgcattgggt ccgccaggcc     180
cccggcaaag gccttgagtg ggtggcggtc ataagctatg acgccaacta caagtactat     240
gccgactcag ttaaaggccg gtttacaatt tctcgagata actcgaaaaa cacgctgtat     300
ttgcaaatga attcactcag ggccgaggat accgctgttt actattgcgc taaagattct     360
```

```
cagctaagaa gtctgctgta ttttgaatgg ctgtcacaag gatatttcga ttactgggga    420
cagggcacgc tggtcaccgt gtcatcagcc tcaacgaaag ggccatctgt tttccccctc    480
gctccctcat caaaatcaac ctcaggaggg accgccgccc ttggttgcct cgttaaggat    540
tactttcccg aacctgtcac ggtgtcatgg aacagtggtg cactgacgtc aggggtgcat    600
actttcccgg ctgtgctaca gtccagtggg ctgtactctc tgagctcagt cgtgacggtg    660
cccagctcat ccctgggcac acagacctat atctgcaacg tcaaccacaa accatcaaat    720
accaaggttg ataagaaggt tgagcccaaa tcgtgcgaca aaacacacac ctgtccccct    780
tgcccggccc ccgagctcct cggaggtcct tctgtgttct tatttccccc taaacccaag    840
gatactctga tgatatcacg cacacccgag gtcacatgcg ttgtagtgga tgtcagccat    900
gaggagcccg atgtgaaatt caattggtac gtcgacgggg tggaggttca taacgcaaag    960
accaaaccca gagaggagca gtataactca acatatcgag tcgtatcagt cttgactgtg   1020
cttcatcaag actggctgaa tggaaaggag tataagtgta agtgtcaaa caaagctttg   1080 cctgctccca tcgagaaaac gatatcgaag gctaaagggc agccccgaga gccccaggtt   1140
tacaccctgc ctccctcccg tgacgagctg acaaagaatc aggtttcact gacgtgccta   1200
gtcaagggat tctatccatc cgacattgct gtagaatggg agagtaacgg ccagccggag   1260
aacaattaca aaaccacgcc acccgtgctg gactcagacg gttcattctt cctctactca   1320
aaactgacag tggacaaatc acggtggcag cagggcaatg tattctcctg ctccgttatg   1380
catgaggcac tccacaacca ctatacgcag aaatctctct cgctgtcacc cggccgtaaa   1440
agacgggctc ccgtgaaaca gactctgaat tttgaccttc ttaagctggc tggagatgtc   1500
gagtccaatc ccggacctat gtataggatg cagctcctct tattgattgc actgagtctg   1560
gctcttgtaa cgaatagcga tattgtcatg actcagagtc ccgattcact cgctgtatca   1620
cttggggaga gggccaccat caattgcaaa tcatcacagt cagtgttgta cagctctaac   1680
aacaaaaact acctggcttg gtaccagcag aaacccggac agccccctaa actcctcatc   1740
tactgggctt ctacccgcga atctggggtg cccgatagat tcagcggctc tgggagtggc   1800
accgatttca ccctgacgat aagcagtctc caggccgagg acgttgctgt gtactattgc   1860
cagcagtatt acagtacgcc cctgacattc ggacagggta ccaaagttga gatcaaacgg   1920
actgtggctg caccctctgt tttcattttt cctccctccg acgagcagct gaaaagtggt   1980
accgcatccg ttgtgtgcct tctcaacaac ttttatcccc gggaagcgaa agtacagtgg   2040
aaagttgata acgccctcca gtctgggaac tcgcaggaga gcgtaaccga acaggactca   2100
aaagattcaa catatagttt gtcatctacg cttaccctgt ctaaggctga ttacgagaaa   2160
cataaggtct atgcttgcga ggttacgcat caaggattgt caagccccgt gactaagagc   2220 ttcaatagg gagagtgt                                                 2238
```

<210> SEQ ID NO 21  
<211> LENGTH: 2238  
<212> TYPE: DNA  
<213> ORGANISM: Artificial Sequence  
<220> FEATURE:  
<223> OTHER INFORMATION: F16 cDNA

<400> SEQUENCE: 21

```
atgtaccgaa tgcagctcct gtcttgtatt gctttaagct tagcccttgt cactaattca     60
caagtgcagt tggtagagtc cggtggcggc gtggtacagc cggggcgctc ccttcgtctg    120
```

```
agctgtgctg catccggctt tacatttttcc acttatgcca tgcattgggt cagacaggcc      180
cctgggaaag gtcttgaatg ggttgccgtg atatcttacg atgccaatta caagtactac      240
gccgactccg tcaaaggacg ctttacaatc agccgggaca acagcaagaa cacactgtat      300
ctgcaaatga attccctgcg cgcggaggac acagccgtct actattgcgc taaggattcc      360
cagttgagaa gtctgctata ctttgagtgg ctaagccagg ggtactttga ctactggggc      420 cagggacac tagtgacagt ctctagcgcg tccacgaagg gaccctctgt gtttcctctg       480
gccccaagct ccaagtcaac atccgggggg actgcagcct aggatgtct ggttaaagac       540 tacttccctg aacctgtgac cgtgtcctgg aacagcgggg cactgacaag cggcgtgcac      600
acatttccgg cggtgttaca gtctagcgga ctgtacagcc tctcgagcgt agttacagtg      660
cccagcagtt cccttgggac acaaacttac atttgcaatg tcaatcataa gccaagcaac      720
accaaagtcg ataagaaggt tgagcctaag agctgcgata agacccatac ttgtccgccc      780
tgccctgccc ctgagttgct gggggggccc agtgttttc ttttccctcc aaaacccaag       840
gatacgctca tgatatcccg tactcctgaa gttacatgcg tagtagtgga cgtgtcccat      900
gaggaacccg acgtgaaatt caattggtac gtggacggag tcgaggttca caatgctaag      960
acaaaacctc gagaggagca gtacaatagc acataccgtg tggtatccgt gctgacagtg      1020
ctacaccagg attggctgaa cgggaaggag tataagtgta aagtctccaa taaggccctg     1080
ccagctccca ttgagaaaac catatccaag gccaagggcc agccccgaga gccccaggtc     1140
tatacactgc ccccatcccg ggacgagctg acaaagaatc aagtgtccct tacatgtctt     1200
gtaaaaggat tctatccctc ggatatagcc gtagagtggg aaagcaacgg ccagcccgag    1260
aacaattaca aaacaacacc ccctgtgctg gatagcgacg gcagcttttt tctgtactcc    1320
aaattgacag ttgacaaaag cagatggcag caggggaatg tgttcagttg ctccgtgatg    1380
catgaggcct tgcataatca ttacacacag aagtcactgt ccctgtcccc cgggcgcaaa    1440
agaagggccc ccgtaaaaca gaccttgaat tttgatttgc tcaaattagc cggcgatgtg    1500
gagagcaacc caggaccgat gtacaggatg cagctattgt tactcatcgc ccttttctctg   1560 gcactcgtta ctaattccga catagtgatg actcagagcc ccgacagcct ggccgtatcc    1620 ctggggaaa gggccaccat caattgcaaa tctagtcaga gcgtattgta ctcctccaac    1680
aacaagaact acctcgcatg gtatcagcag aagcctgggc agccccccaa actgctgata    1740
tactgggctt ccacaagaga gtccggggtt ccagaccgtt ttagcgggag tgggagcggg    1800
acagatttta cgctcaccat cagcagccta caggctgagg acgtggccgt gtactactgt    1860
cagcagtact actcgactcc actaacattt gggcagggca caaagttga gataaaacgc    1920 acagtggctg cgccgagcgt gttcattttt ccaccctctg acgaacagct aaagagcggg   1980
accgcctccg tcgtgtgttt actcaacaat ttctacccc gggaggctaa agtgcagtgg    2040
aaagtagaca cgcacttca gtctgggaac agtcaggaga gcgtgacaga gcaggactca    2100
aaggacagca catatagcct cagcagcacg ctgacactgt ccaaagccga ctacgagaaa    2160
cacaaagtgt acgcctgcga ggtcacacat cagggcttgt cctccccgt tacaaaaagc     2220 tttaatcgtg gagagtgt                                                  2238
```

<210> SEQ ID NO 22
<211> LENGTH: 2238
<212> TYPE: DNA
<213> ORGANISM: Artificial Sequence
<220> FEATURE:
<223> OTHER INFORMATION: F16 42 cDNA

<400> SEQUENCE: 22

```
atgtatagaa tgcagctcct ttcttgcatt gccctatcac tagcattagt cacgaattca        60
caagtgcagc ttgttgaatc aggaggcggc gttgtgcagc ctggccgttc acttcgcctg       120
agttgcgctg caagcggttt cacattttca acttacgcaa tgcattgggt cagacaggct       180
ccaggaaaag gtctagaatg ggtggctgtg atctcatacg acgctaacta taagtactac       240
gccgattcag tgaaaggcag attcacaatt tctcgtgata actcaaagaa taccctgtac       300
ctacagatga actcactgag ggcagaggat accgcagttt actactgtgc aaaagacagc       360
cagttacggt cgttgctgta cttcgagtgg ctgtcacaag gctacttcga ttattgggga       420
cagggcaccc tagttaccgt gtccagtgca agcaccaaag ggcccagcgt tttccctctc       480
gcccctcat caaaatcaac ctcaggggc actgcagcat tgggttgcct ggtcaaagat        540
tactttcctg agcctgtcac cgtttcctgg aattctggcg cactaactag tggcgtgcac       600
acatttccag cggtcttaca agttcaggc ctctattcat tgtcatccgt cgttaccgtc        660
ccttcatcat ctctgggcac ccagacgtac atctgtaatg ttaaccacaa accttcgaac       720
acaaaagttg acaaaaaggt tgaacccaaa tcatgcgata agacacatac gtgtcccccg       780
tgccctgcac cggagctgct cggtggccca tcagtgtttc ttttcccacc caaaccaaaa       840
gatactctga tgatctcacg gacaccagaa gtgacctgtg ttgtggttga tgtcagccac       900
gaggaacccg atgttaagtt caattggtac gttgatggcg ttgaggttca caacgccaaa       960
acgaaaccca gagaggagca gtacaacagt acttaccgtg ttgtatcagt tttgactgta      1020
ctgcaccagg actggctgaa tggcaaagag tacaaatgca agtttctaa taaggctctc       1080
cccgcgccca tcgaaaagac catctcaaaa gcaaagggc agccccgcga acctcaagtt        1140
tacaccttgc ccccatcccg tgatgaactg acgaaaaatc aagtgtctct cacatgtttg      1200
gttaagggct ctacccgtc tgatatagcc gtcgaatggg aatccaacgg ccagcccgag       1260
aacaactata agacgacgcc accgtactg gatagtgacg gcagctttt cttatactca        1320
aaactgacag ttgacaaatc aagatggcag cagggcaacg tatttcttg ctctgtgatg        1380
cacgaggcac tccacaatca ctacactcag aaatcactat ctctgagccc tgggcgaaaa      1440
cgccgcgccc ccgtaaaaca gaccttgaac ttcgatctac tgaagctggc tggagatgta      1500
gagagtaatc ccgcccaat gtaccggatg cagttgttat tactgatagc actttccctg       1560
gcactggtta ccaacagcga tattgttatg actcagtccc ccgactctct ggctgtgtca      1620
ttaggggaaa gggcaaccat caattgtaaa agtagtcagt cagtgttgta ctcatcaaac      1680
aacaagaact acctcgcgtg gtaccaacag aaacctggcc agccccctaa actgcttatc      1740
tactgggcat cgacgcgaga gtcaggcgtt cccgatcgat tcagtggcag cggcagtggc      1800
acagatttta cacttacgat ttcatccctg caagccgagg acgtcgctgt ctattactgt      1860
cagcagtatt acagcacacc tctgacattc ggccagggca ctaaggttga atcaaaagg       1920
accgtcgctg caccctcggt attcattttt ccaccctctg atgaacagct gaagtctggg      1980
accgcctcag ttgtctgtct gctcaacaat ttctacccgc gtgaagcaaa agttcagtgg      2040
aaagtggaca acgcacttca gtccgggaac tcacaggaat cggttacaga gcaggatagc      2100
aaagattcaa cctattcact ctcatctaca ctgaccctgt ctaaagcaga ttacgagaag      2160
cacaaggttt acgcatgcga agtgacacac cagggcctgt cctcccccgt tactaagagc      2220
ttcaaccgcg gcgaatgt                                                    2238
```

<210> SEQ ID NO 23
<211> LENGTH: 2238
<212> TYPE: DNA
<213> ORGANISM: Artificial Sequence
<220> FEATURE:
<223> OTHER INFORMATION: F16 B42

<400> SEQUENCE: 23

| | | | | | |
|---|---|---|---|---|---|
| atgtaccgga | tgcagctttt | atcttgtatt | gcactttctc | tcgctcttgt | tacgaatagt | 60 |
| caggtccagc | tcgtggagag | tggagggggc | gtcgtgcagc | ccggaagatc | tctacggcta | 120 |
| tcctgcgccg | ctagtggttt | cacgttttct | acgtatgcga | tgcactgggt | cagacaggct | 180 |
| ccgggcaaag | gtcttgaatg | ggttgctgtc | atctcttatg | acgctaatta | caagtactac | 240 |
| gccgattctg | tgaaaggtcg | ctttaccata | tctagggaca | cagcaagaa | taccctttac | 300 |
| cttcaaatga | attccttacg | cgctgaagat | actgccgtct | actactgcgc | taaggatagc | 360 |
| cagctgcgtt | ctttactgta | ctttgaatgg | ctgagtcagg | gttactttga | ctactgggga | 420 |
| caggggaccc | tagtgacagt | gtctagcgcc | tctacaaagg | gtcccagtgt | ctttccccctt | 480 |
| gctccctctt | caaaatctac | ctccggcggt | accgctgctc | ttggatgcct | cgtgaaggac | 540 |
| tatttcccgg | aacctgtgac | tgtgtcttgg | aatagtggcg | cactcacatc | gggggtacac | 600 |
| acatttccgg | ctgtccttca | atcatctggg | ctgtatagcc | tgagttccgt | ggtcactgtg | 660 |
| cccagtagct | cccttggaac | ccagacatac | atttgcaacg | tcaatcataa | gccttctaac | 720 |
| acgaaagtag | ataagaaagt | tgaaccaaag | tcttgcgata | agacccatac | gtgtccccca | 780 |
| tgtccggccc | ctgaacttct | ggcggcccc | tctgtctttc | ttttcccacc | aaagccaaaa | 840 |
| gatacgctca | tgattagtcg | cacccccgga | gttacctgtg | tggtggtcga | cgtgtcacat | 900 |
| gaggagccag | atgttaagtt | taattggtat | gtcgacggcg | tggaagtcca | taatgctaaa | 960 |
| accaagcccc | gcgaggaaca | gtataatagc | acatacaggg | tagtgtctgt | gctcaccgtg | 1020 |
| ctgcatcagg | actggctgaa | tggaaaagaa | tacaagtgta | agtgtcaaa | taaggcactt | 1080 |
| ccggctccga | tagagaaaac | aattagcaag | gccaagggtc | aaccgcgaga | accacaagtt | 1140 |
| tacacactgc | ccccgtcacg | cgacgaactc | acgaagaatc | aggtttcctt | gacttgcctg | 1200 |
| gtcaagggat | tttacccgag | tgacatcgcg | gtagaatggg | agagtaatgg | acagcctgag | 1260 |
| aacaattaca | agaccactcc | gcccgttctg | gactccgacg | gctcattttt | cttgtactcc | 1320 |
| aaactgacgg | tcgacaaaag | tcggtggcag | caggggaatg | tgttttcctg | ctctgtgatg | 1380 |
| catgaagcac | ttcacaatca | ctatacccag | aaaagtctta | gccttagtcc | cgggaggaag | 1440 |
| cgcagagctc | ccgtaaagca | gacccttaac | tttgatcttc | taaaacttgc | tggcgatgtg | 1500 |
| gagtccaatc | ctggtccgat | gtaccgcatg | caacttctcc | tcctgatcgc | cctgagtcta | 1560 |
| gctctcgtca | caaattctga | catcgtgatg | actcagtctc | cggactctct | tgctgtctca | 1620 |
| ctcggagaga | gggctactat | caattgcaag | agcagtcaga | gtgtgctgta | ttcatctaac | 1680 |
| aataagaact | atcttgcttg | gtaccagcag | aagcctgggc | aaccccccaaa | gttactgatc | 1740 |
| tactgggcca | gcacacgcga | atcgggcgtc | ccggaccggt | ttagtggtag | tggatctggc | 1800 |
| acagatttta | ccctgaccat | aagttccctg | caagccgaag | atgtggctgt | ttactattgc | 1860 |
| cagcagtact | acagtacccc | attgacgttc | ggccagggga | ctaaggtcga | aatcaagcgc | 1920 |
| acggtggcag | ctccttctgt | gtttatcttc | ccaccgagtg | acgagcagct | caagagcggt | 1980 |
| actgctagtg | tcgtgtgctt | gcttaacaat | ttttatcccc | gcgaggctaa | ggtccagtgg | 2040 |
| aaagttgaca | acgcccttca | gtccggcaat | agtcaggaat | ctgtgaccga | acaggactct | 2100 |

```
aaggacagca cttattctct ttcctcaaca ctcacactca gcaaggccga ctatgaaaaa    2160
cataaggttt acgcatgcga agtgacacat cagggtcttt cttctcccgt cacaaagagc    2220
ttcaaccgcg gcgaatgt                                                  2238

<210> SEQ ID NO 24
<211> LENGTH: 20
<212> TYPE: PRT
<213> ORGANISM: Homo sapiens

<400> SEQUENCE: 24

Met Tyr Arg Met Gln Leu Leu Ser Cys Ile Ala Leu Ser Leu Ala Leu
1               5                   10                  15

Val Thr Asn Ser
            20

<210> SEQ ID NO 25
<211> LENGTH: 19
<212> TYPE: PRT
<213> ORGANISM: Artificial Sequence
<220> FEATURE:
<223> OTHER INFORMATION: mutated IL2

<400> SEQUENCE: 25

Met Arg Met Gln Leu Leu Leu Leu Ile Ala Leu Ser Leu Ala Leu Val
1               5                   10                  15

Thr Asn Ser
```

AAV-MEDIATED EXPRESSION OF ANTI-INFLUENZA ANTIBODIES AND METHODS OF USE THEREOF

STATEMENT OF FEDERALLY SPONSORED RESEARCH

This invention was made in part with government support under W911NF-13-2-0036 awarded by Defense Advanced Research Projects Agency (DARPA). The government has certain rights in the invention.

INCORPORATION-BY-REFERENCE OF MATERIAL SUBMITTED IN ELECTRONIC FORM

Applicant hereby incorporates by reference the Sequence Listing material filed in electronic form herewith. This file is labeled "UPN_15-7484PCT_ST25.txt".

BACKGROUND OF THE INVENTION

Influenza infections are the seventh leading cause of death in the US, equating to 49,000 deaths per year, a significant proportion of almost 500,000 deaths worldwide [Prevention, C.f.D.C.a. Estimates of deaths associated with seasonal influenza: United States, 1976-2007. 2010; Available from: MMWR Morb. Mortal. Wkly. Rep. 59:1057-1062]. The economic burden of annual influenza epidemics is estimated to be in the order of $87 billion. More than half of this cost covers the hospital care required for almost 1 million patients, of which 70% are elderly patients (>65 years of age) [Molinari, N. A., et al., Vaccine, 2007. 25(27): p. 5086-96]. In addition, immunocompromised individuals, such as patients with HIV/AIDS, organ transplant recipients, or those suffering from an autoimmune disease are considered high-risks groups for influenza and have an increased susceptibility to infection, as well as its complications, which include fatal pneumonia and acute respiratory distress syndrome [Oliveira, E. C., et al., J Intensive Care Med, 2003. 18(2): p. 80-91.]. Influenza is an RNA virus that belongs to the Orthomyxoviridae family. There are three influenza virus genera; A [Medina, R. A. and A. Garcia-Sastre, Nat Rev Microbiol, 2011. 9(8): p. 590-603.], B [Paul Glezen, W., et al., Am J Public Health, 2013. 103(3): p. e43-51] and C. These types of influenza are categorized based on antigenic differences between the matrix and nucleoproteins. In the US, influenza A and B are responsible for seasonal epidemics during the winter months. Influenza C is not known to cause epidemics and is associated with mild respiratory disease.

Human-to-human transmission of influenza A or B typically occurs as a result of aerosol or fine droplets that are spread through sneezing or coughing of the infected subject. The influenza virus typically enters the nasal airway passages. There the hemagglutinin (HA) binds to the sialic acid receptors present on respiratory epithelial cells and the viral envelope fuses with the host cell membrane. Subsequently the viral RNA enters the cytosol and eventually the host cell nucleus where it replicates. Following viral replication, the host cell then lyses and several thousand viruses are released. This cycle continues, the virus replicates and eventually disseminates to the lower airways where it causes severe disease that may be fatal in certain high-risk subject groups [Medina, cited above].

While influenza vaccine coverage in the US has increased in the last decade, studies have demonstrated low efficacy of seasonal influenza vaccines in elderly patients and immunocompromised patients [Ljungman, P., Clin Microbiol Infect, 2012. 18 Suppl 5: p. 93-9]. Several aspects of the influenza virus and the immune response of the human host to an influenza infection conspire against a simple prophylaxis remedy. Key targets of the adaptive immune response such as the HA protein of the virus evolve rapidly rendering immune memory responses only partially protective to new infections [Medina, cited above]. The response of humans to a natural infection or an influenza vaccine is usually limited in breadth, providing protection only against closely related influenza subtypes. This has led to annual vaccination of subjects aged 6 months and over against seasonal strains of influenza viruses that are predicted to emerge during the upcoming season.

Influenza A viruses can infect humans and various other mammals including pigs, horses, dogs as well as birds [Medina, cited above]. These viruses are divided into two subtypes based on the structure of the two surface proteins hemagglutinin (HA) and neuraminidase (NA). There are 18 known HA subtypes and 11 known NA subtypes [CDC. Types of Influenza Viruses. 2014; Available from: http://www_cdc_gov/flu/about/viruses/-types_htm]. Influenza A has been linked to large epidemics and pandemics, notably the 1918 pandemic that have been associated with significant morbidity and loss of life. Epidemic influenza, also known as seasonal influenza, is typically uncomplicated and remains confined to the upper respiratory tract of only humans [Molinari, cited above; Glezen, cited above]. Viral pneumonia rarely occurs but susceptible subject populations, including pregnant women, the elderly, patients with pre-existing cardiovascular and lung disease, are considered high risk groups for complications from influenza B. Typically seasonal influenza is considered to result in mild disease.

The emergence of a new influenza pandemic remains a threat that could result in substantial loss of life and worldwide economic disruption. It is believed that the repertoire of immune memory generated from previous influenza infections and vaccinations helps to blunt the sequelae of a new infection and augments the efficacy of a vaccine. This is not the case when an influenza virus residing in animal reservoirs acquires a human respiratory tropism and is transmitted to humans [Juno, J., et al., Clin Dev Immunol, 2012. 2012: p. 797180]. These zoonotic strains are quite distinct from those that normally circulate in the human population and can lead to pandemics with lethal consequences as they are not effectively controlled by vaccines developed to human strains of the virus [Juno, cited above]. As was learned from the 2009 H1N1 pandemic [Shapshak, P., et al., Mol Diagn Ther, 2011. 15(2): p. 63-81], the vaccine development time is not fast enough to support population vaccination in response to an emerging pandemic. Unlike epidemics, influenza pandemics are infrequent but can result in significant loss of life. Pandemic influenza viruses arise from genetic assortment between nonhuman (i.e., avian) and human viruses. Reassortment of segmented viruses is a key mechanism for rapid novel virus creation. These "antigenic shift" events introduce an immunologically novel influenza virus into the human population, to which there is no pre-existing immunity. Two human influenza pandemics in the last century were linked to lineages that arose from reassortment of genomic segments with a genome of non-human origin. During the most recent pandemic (2009), younger people were disproportionately affected by lower respiratory tract disease requiring hospitalization, relative to inter-pandemic years [Dawood, F. S., et al., Lancet Infect Dis, 2012. 12(9): p. 687-95.].

Influenza vaccines are not always effective at protecting from influenza. In early 2013, an influenza outbreak was reported in a vaccinated US Navy minesweeper population of 102 young (21-44 years of age) healthy men. Almost 25% of these vaccinated subjects presented with influenza symptoms that required medical care. PCR analysis showed that the influenza strain was H3N2 and shared 99% homology to the strains circulating in the 2013-2014 influenza season, similar to the H3N2 antigenic component of the 2013-2014 influenza vaccine [T. L. Aquino, et al., Influenza Outbreak in a Vaccinated Population—USS Ardent. mmwr 63(42);947-949 2014].

Two monoclonal antibodies have emerged as candidates as prophylactics for influenza. For influenza A, FI6 [Oliveira, et al, cited above] that was discovered by the Lanzavecchia group [US2010/0080813] and for influenza B, CR8033 [Dreyfus, C., et al., Science, 2012. 337(6100): p. 1343-8; U.S. Pat. No. 8,852,595] an antibody discovered by the Wilson (The Scripps Research Institute) and Friesen (Crucell) groups. FI6 has been reported to be highly effective against several strains of influenza A (including pandemic strains A/H1N1/1918 and A/H1N1/2009) and has a broad and potent reactivity and neutralizing profile across all Group 1 and Group 2 HAs [Corti, D., et al., Science, 2011. 333(6044): p. 850-6]. Importantly, these Abs have been shown not to generate escape mutants even after multiple serial passages [Oliveira, cited above; Paul Glezen cited above]. It has been reported that when this antibody was delivered via a vector it protected mice and ferrets from lethal challenge from multiple influenza A strains [Limberis, M. P., et al., Sci Transl Med, 2013. 5(187): p. 187ra72; Limberis, M. P., et al., Clin Vaccine Immunol, 2013. 20(12): p. 1836-7; Adam et al. Clin Vaccine Immunol. 2014 Nov.; 21(11):1528-33;].

There is one universal antibody, CR9114 [Dreyfus., C. et al, Science, 2012, 337(6100): p1343-8], that binds to both Group 1 and Group 2 influenza A and influenza B viruses. However, the utility of this antibody is hampered by the relatively high antibody concentrations required for neutralization of the various influenza A and B strains. The IC50 for Group 1 viruses ranged from 0.1 to 100 µg/ml, with only two strains falling between 0.1 and 1 µg/ml, and the remaining between 1 and 100 µg/ml. The IC50 for Group 2 viruses was even less favorable, with just one strain falling below 1 µg/ml[Dreyfus, cited above]. Relatively high concentrations of CR8071 were required for in vivo protection against influenza B and suboptimal doses resulted in higher weight loss compared to non-immunized mice (Figure S2, and escape mutants were generated after just 15 passages [Dreyfus, cited above]. Another Influenza B antibody CR8020 resulted in generation of escape mutants after just four passages [Dreyfus, cited above].

There is currently one approved therapy (FluMist Quadrivalent) which is delivered intranasally. However, it is not suitable for subjects that have a severe allergy to eggs and subjects who are 2 through 17 and take aspirin or medicines taking aspirin [Shapiro R J, S. K., et al. "The potential American market for generic biological treatments and the associated cost savings". 2008; Available from: http://www_sonecon_com/docs/studies-/0208 _Generic-BiologicsStudy.pdf].

Adeno-associated viruses (AAVs) are members of the family parvoviridae. These small DNA viruses have shown substantial promise as vectors for achieving stable transgene expression following in vivo delivery. AAVs were initially discovered as contaminants in laboratory preparations of adenovirus [Melnick, J. L., et al., Association of 20-Millimicron Particles with Adenoviruses. J Bacteriol, 1965. 90(1): p. 271-4] Immunological characterization of these isolates suggested the existence of six serotypes of AAV. Sero-epidemiologic studies indicate a broad exposure of humans to the various AAV serotypes, with greater than 60% of the population demonstrating NAbs to most of the six AAV serotypes by the age of 10 [Calcedo, R., et al., J Infect Dis, 2009. 199(3): p. 381-90]. In the early 2000s, the repertoire of AAV vectors was expanded through the isolation of several hundred new AAV viruses from human and non-human primates [Gao, G., et al., J Virol, 2004. 78(12): p. 6381-8]. More than 120 genotypes of AAV vectors, including the original six serotypes from human and NHP tissue sources were isolated, characterized phylogenetically and organized in six different clades [Gao, G., et al., J Virol, 2004. 78(12): p. 6381-8].

There remains a need in the art for anti-influenza therapies effective for therapeutic and/or prophylactic use.

SUMMARY OF THE INVENTION

In one aspect the invention provides a composition useful for passive immunization against influenza infection. The composition comprises an anti-influenza A antibody expressed from an AAV vector and an anti-influenza B antibody expressed from a second AAV vector. In one embodiment, a first non-replicating recombinant AAV has an AAV9 capsid (rAAV9) and a vector genome which comprises nucleic acid sequences encoding: (a) an AAV inverted terminal repeat (ITR) (b) an enhancer, (b) a chicken beta-actin promoter, (c) an intron (d) a 5' UTR, (e) a leader peptide operably linked to a FI6v3 heavy chain, (f) a FI6v3 heavy variable chain; (g) human IgG1 Fc chain (CH2-3); (h) a leader peptide operably linked to a immunoglobulin kappa light variable chain; (i) an immunoglobulin constant light chain; (j) a furin recognition site; (k) an F2A linker; (1) a polyadenylation signal; and (m) an AAV inverted terminal repeat. In certain embodiments, the composition contains a second non-replicating rAAV9 which has a vector genome which comprises nucleic acid sequences encoding: (a) an AAV inverted terminal repeat (ITR) (b) an enhancer, (b) a chicken beta-actin promoter, (c) an intron (d) a 5' UTR, (e) a leader peptide operably linked to a CR8033 heavy chain, (f) a CR8033 heavy variable chain; (g) a human IgG1 Fc chain (CH2-3); (h) a leader peptide operably linked to an immunoglobulin light variable kappa chain; (i) a constant light chain cDNA; (j) a furin recognition site; (k) an F2A linker; (1) a polyadenylation signal; and (m) an AAV inverted terminal repeat, and an aqueous liquid suspension base.

In another aspect, a method for protecting human patients against influenza is provided which involves administering an effective amount of an anti-influenza composition as provided herein. Suitably, the patient is administered a dose in an amount of about $1 \times 10^{10}$ to about $3 \times 10^{13}$ genome copies. In certain embodiments, the composition is administered intranasally. In other embodiments, the composition is administered intramuscularly or intravenously.

In a further aspect, a product is provided which comprises a container comprising an anti-influenza composition as described here in, an optional diluent, and instructions for administration.

In still a further aspect, the invention provides a method of preventing influenza comprising administering a vector expressing a synthetic anti-influenza antibody as described herein. Such a therapy may be in combination with other vectors expressing different antibodies, or other anti-viral compositions. Optionally, the method may be used as a vaccine, i.e., prior to influenza exposure.

Still other aspects and advantages of the invention will be readily apparent from the following detailed description of the invention.

BRIEF DESCRIPTION OF THE DRAWINGS

FIG. 1A is a schematic representation of AAV-FI6 mAb and FIG. 1B is a representation of AAV-CR8033 mAb.

FIGS. 3A and 3B provide the determination of the minimum effective dose (MED) of AAV2/9.CB7.FI6 required for protection against challenge with PR8. (A) Weights of mice treated intranasal (IN or i.n.) with varying doses of AAV2/9.CB7.FI6 following challenge with $5LD_{50}$ PR8. (B) Survival of challenged mice. Mice were euthanized when they appeared in distress or their body weight declined ≥30%.

FIGS. 4A and 4B show the determination of the FI6 expression at the lung (BALF) and nasal (NLF) surfaces. Mice were given IN various doses of AAV2/9.CB7.FI6 and the level of antibody expressed in the surface liquid lining the lung and nose harvested at necropsy was assessed. FIG. 4A provides results for FI6 expression in BALF and FIG. 4B provides results for FI6 expression in NLF surfaces.

FIG. 5 shows quantification of viral load in lung of naïve and mice vaccinated with AAV2/9.CB7.FI6. Three mice from the non-vaccinated (naïve) and the AAV2/9.CB7.FI6 vaccinated groups were necropsied at day 6 to quantify viral load in the lung.

FIG. 6A shows weights of mice following challenge at day 0. FIG. 6B shows survival of challenged mice. Mice were euthanized when they appeared in distress or their body weight declined ≥30%.

FIG. 7A shows weights of mice pretreated IN with varying doses of AAV2/9.CB7.CR8033 following challenge with $5LD_{50}$ B/Lee/40. FIG. 7B shows survival of challenged mice. Mice were euthanized when they appeared in distress or their body weight declined ≥30%.

FIGS. 11A, 11D and 11G show the weights of mice overtime; black circles represent mice that received the vector via a pipette (liquid delivery), dark grey squares represent mice that received vector that was processed through the IMAD and light grey triangles represent mice that did not receive vector (naïve mice) and served as controls for the PR8 challenge. The naïve mice were euthanized by day 8 due to severe weight loss. At the conclusion of the experiment (day 21), the survivors were sacrificed, BALF harvested for antibody expression and lungs processed for quantification of AAV9 genomes by Taqman PCR. FIGS. 11B, 11E, and 11H show antibody expression by protein A ELISA was quantified in the BALF of mice given a mixture of $10^9$ GC each of AAV2/9.CB7.CR8033 and AAV2/9.CB7.FI6 formulated in PBS-pH 6.8, PBS-pH 7.2. and PBS-pH 7.4, respectively. Results are shown in ng/mL for the device (IMAD) and pipette control (liquid). FIG. 11C, FIG. 11F, and FIG. 11-I show AAV9 genomes quantified by Taqman PCR in the lung of mice given a mixture of $10^9$ GC each of AAV2/9.CB7.CR8033 and AAV2/9.CB7.FI6 formulated in PBS-pH 6.8, PBS-pH 7.2. and PBS-pH 7.4, respectively.

FIGS. 12A-12G show vector-mediated prophylaxis against challenge with PR8 and influenza B (B/Lee/40) virus. 6 week old female BALB/c mice (n=5/group) were given i.n. a mixture of $1\times10^9$ genome copies (GC) of AAV2/9.CB7.CR8033 and $1\times10^9$ GC of AAV2/9.CB7.FI6 in a total volume of 50 µl PBS. The vector was formulated in PBS-pH 7.4. Mice were challenged with $5LD_{50}$ of PR8 (FIG. 12A) or B/Lee/40 (FIG. 12D) virus seven days later. The weights of the animals were recorded daily and mice were euthanized when they appeared in distress or when they lost ≤30% of their pre-challenge body weight. Shown are the weights of mice challenged with PR8 (FIG. 12A) or B/Lee/40 (FIG. 12D) overtime; black circles represent mice that received the vector via a pipette (liquid delivery), dark grey squares represent mice that received vector that was processed through the IMAD and light grey triangles represent mice that did not receive vector (naïve mice) and served as controls for the PR8 challenge. With the exception of one survivor, naïve mice (4 of 5) were euthanized by day 8. At the conclusion of the experiment (day 21), the survivors were sacrificed, BALF harvested for antibody expression and lungs processed for quantification of AAV9 genomes by Taqman PCR. FIG. 12B shows antibody expression by protein A ELISA quantified in the BALF and FIG. 12C shows AAV9 genomes present in the lung quantified by Taqman PCR in mice given a mixture of $10^9$ GC each of AAV2/9.CB7.CR8033 and AAV2/9.CB7.FI6 formulated in PBS-pH 7.4 and challenged with PR8. FIG. 12E shows antibody expression in the BALF quantified by protein A ELISA and FIG. 12F shows AAV9 genomes present in the lung quantified by Taqman PCR in mice given a mixture of $1\times10^9$ GC each of AAV2/9.CB7.CR8033 and AAV2/9.CB7.FI6 formulated in PBS-pH 7.4 and challenged with B/Lee/40. FIG. 12G shows the amount of vector suspension (0.5 mL) plunged through the IMAD to evaluate physical loss of vector solution. As shown, a physical liquid loss of 4-6.6% of initial volume was observed when the vector solution was plunged through the IMAD.

DETAILED DESCRIPTION OF THE INVENTION

Figure 1A:
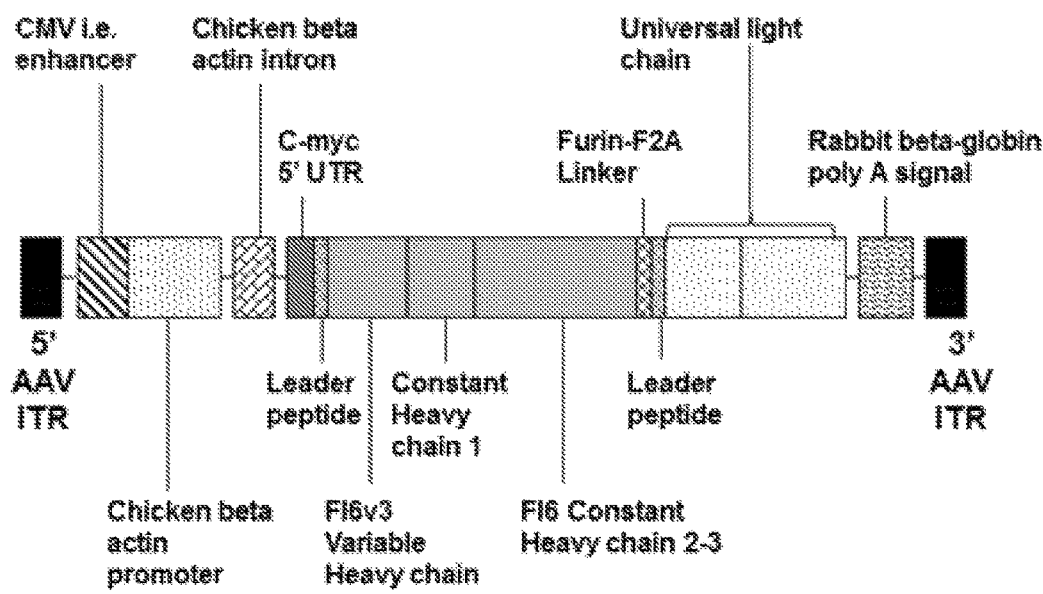
FIGS. 1A-1B provide as a schematic representation of the GTP101 vector components.
Figure 1B:
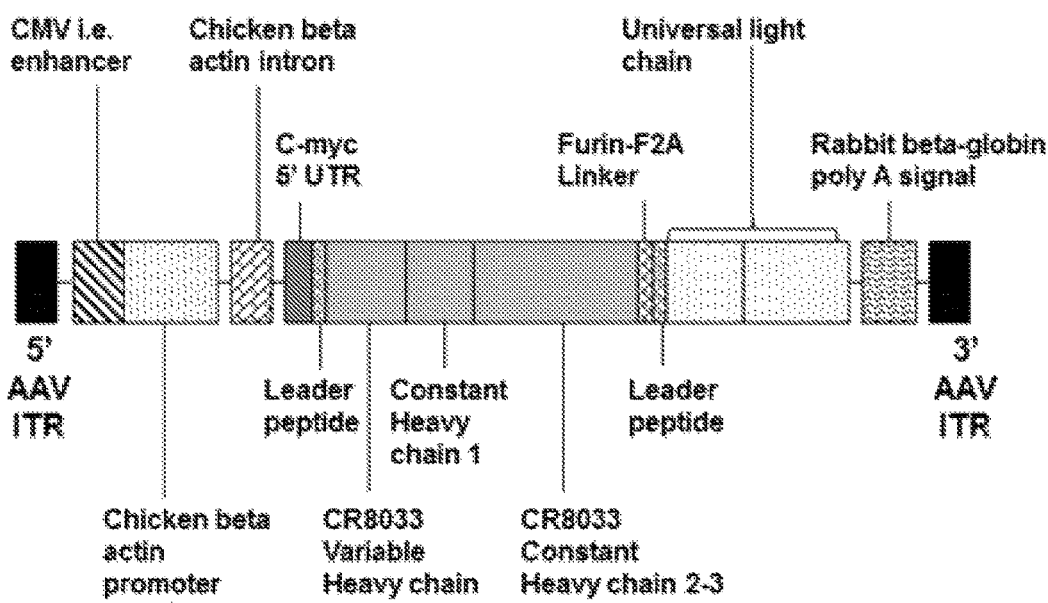

A composition is provided herein which is a bipartite drug product composed of two non-replicating recombinant adeno-associated virus (AAV) vectors of serotype 9 expressing recombinant antibodies which confer passive immunization against influenza A and influenza B, respectively.

The composition provided herein has several advantages over currently available influenza vaccines. The anti-influenza A and anti-influenza B antibody constructs co-expressed in vivo provide passive immunization against influenza A and influenza B infection. In other words, in contrast to a traditional vaccine which delivers an influenza antigen and relies upon the patient's immune system to mount an immune response and generate antibodies, the composition provided herein delivers the anti-influenza antibodies to the patient. Thus, the vaccine is useful for patients who have immune systems which are not capable of generating a satisfactory protective immune response following immunization with an influenza antigen. Further, the composition provided herein may provide a more rapid onset of protection post-administration than an antigen-based vaccine approach.

Other advantages include the fact that the composition may be delivered intranasally; thus, the approach is minimally invasive and is without the risk of mild infection or other side effects associated with delivery of current intranasal vaccines having an attenuated virus. Still another advantage is that the composition is useful for patients having egg allergies. Nor is the composition contraindicated for patients taking aspirin or medicines containing aspirin. Further, the rAAV compositions provided herein substantially reduce the number of repeated parental administrations which are required for protein therapeutics to be effective. In certain embodiments, readministration is required only about 1 time per year following delivery to nasal epithelial cells. In still another advantage, the compositions provided herein may be produced in a shorter time frame than many traditional viral-based influenza vaccines. Thus, the composition of the invention provides a more practical method for protecting at-risk populations.

In certain embodiments, the vectors provided herein express effective levels of functional antibody when delivered intranasally a dose of about 3 mL or less, 2 mL or less, or 1 mL or less, 0.5 mL, or less, e.g., in the range of about 100 µL to 250 µL. In general, the compositions are formulated at a pH of about 5.5 to about 8.5, 6 to 8, or 6.5 to 7.5, or 6.8, 7.2, or 7.4. Thus, the vectors provided herein are highly efficient at providing therapeutic levels of antibody at doses which are convenient for metered doses, or in products or kits containing pre-measured doses. In certain embodiments, the compositions are formulated for intranasal delivery in a manner that the volume and droplet size of the spray preferentially targets the cells of the intranasal epithelium. Expression in the nasal epithelium has been shown to confer protective passive immunity. The compositions may also be formulated for intranasal delivery which targets the lung. The lung may be targeted in addition to the nasal epithelium, or preferentially to the nasal epithelium, e.g., by adjusting the volume and/or droplet size delivered intranasally. When compared to conventional flu vaccine delivered intramuscularly, AAV delivered intranasally results in faster onset of Ab expression (within hrs or a couple of days). However, in certain embodiments, the compositions described herein may be formulated for delivery by other routes, e.g., intramuscular injection, intravenous injection, or other suitable routes. In such instances, suitable formulations and volumes may be determined by one of skill in the art.

Antibody Constructs

In certain embodiments, a composition provided herein delivers two influenza antibodies which are expressed in a cell in vivo via a non-replicating viral vector and secreted therefrom to provide protective immunity. As illustrated in the examples herein, the viral vector is an rAAV and the composition contains two different rAAV stocks, each of which has a different vector genome. In a first stock, the vector genome contains the coding sequences for an influenza A antibody. In a second stock, the vector genome contains the coding sequences for an influenza B antibody.

The influenza A antibody is a synthetic FI6 construct. See, e.g., US Patent Publication No. 2010/0080813, for amino acid sequences of the FI6v3 heavy chain, light chain variable chain, variable regions, and complementarity determining regions. See, also, U.S. Pat. No. 8,124,092. In certain embodiments, the F16v3 expression cassette is constructed encoding the F16 light variable regions of FI6 (GenBank Accession Numbers PDB: AEL31310.1, GI: 342674599 and 342674581), linked to the constant (CH1, CH2 and CH3) domains of human IgG1 and light chain germline kappa sequence linked to human CL domain, generating a monoclonal antibody architecture. In another embodiment, the FI6 expression cassette contains the full-length heavy chain of FI6v3 (see, nt 2440-2760 (CH1), nt2761-3426 (CH2-CH3) of SEQ ID NO:1). The cDNA encoding an illustrative light chain is provided at nt 3511-3909 of SEQ ID NO: 1. (leader nt 3511-3510, kappa chain nt 3571-3909) In still another embodiment, the synthetic FI6 construct contains, at a minimum, the FI6v3 heavy chain variable region, heavy chain constant regions CH1, CH2 and CH3), and an immunoglobulin light chain.

In certain embodiments, the nucleic acid sequence encoding the immunoglobulin domains which compose the anti-influenza A antibody are designed for expression in human cells. Such sequences may include, e.g., FI6v3 heavy chain variable region (nt 2053-2439 of SEQ ID NO:1) and constant regions CH2 and CH3 (nt 2761-3426 of SEQ ID NO:1). However, other coding sequences for the FI6v3 amino acid sequences provided herein may be engineered and are encompassed by the present invention. See, e.g., other sequences encoding the heavy chain variable region (e.g., amino acids of SEQ ID NO:2), the CH1 (e.g., amino acids of SEQ ID NO:3), and/or the CH2-CH3 (e.g., amino acids of SEQ ID NO:4). See, also, SEQ ID NO: 14, 15, 16, 17, 18, 19, 20, 21 22, or 23.

In certain embodiments, the "variable" light chain is a kappa chain derived from a germ line source. For example, the examples provided herein utilize 1c1IIGKV4-1*01 germline gene [*Homo sapiens*] (see, e.g., nt 3571-3909 of SEQ ID NO:1 or nt 3265-3606 of SEQ ID NO:8). Optionally, another nucleic acid sequence encoding the amino acid sequence of the kappa light chain (SEQ ID NO: 6) and/or constant light chain (SEQ ID NO: 7) may be selected. In another alternative, another suitable germline sequence may be selected. In another embodiment, the light chain is a lambda chain. Preferably, a germline sequence which does not alter antigenic specificity of the heavy chain partner is selected as the source of the light chain. Sources of such immunoglobulin germline sequences are provided, e.g., in Kabat database, ncbi.nlm.nih.gov/ and imgt.org/genedb/table?mode=3d&selectGenes=IGKV4-1&selectSpecies=Homo %20sapiens.

The influenza B antibody is a synthetic CR8033 antibody. See, e.g., U.S. Pat. No. 8,852,595, for amino acid sequences of the CR8033 heavy chain, light chain, variable regions, and complementarity determining regions. The antibody has a heavy chain which is an engineered sequence derived from the CR8033 anti-influenza antibody. In one embodiment, the engineered antibody provided herein contains a codon optimized heavy chain variable (e.g., nt 1753-2133 of SEQ ID NO:8), CH1 (e.g., nt 2134-2454 of SEQ ID NO:8), and CH2-CH3 (e.g., nt 2455-3120 of SEQ ID NO:8). In certain embodiments, the CH1 region may be omitted. In other embodiments, different nucleic acid sequences encoding the heavy chain variable region (e.g., SEQ ID NO:9), CH1 (e.g., SEQ ID NO:10), and/or CH2-3 (e.g., SEQ ID NO: 11) may be selected.

In still other embodiments, the light chains may be derived from the F16 antibody. See, e.g., Corti et al, Science, 2011 Aug. 12; 333(6044):860-6, Epub 2011 Jul. 28.

In certain embodiments, a synthetic F16 antibody construct provided herein may be expressed in vitro and used, e.g., a protein therapy or for generating anti-idiotype antibodies. This antibody construct is composed of, at a minimum, an F16 heavy chain combination with a light chain from a germline source.

In other embodiments, a synthetic CR8033 antibody construct provided herein may be expressed in vitro and used, e.g., in a protein therapy or for generating anti-idiotype antibodies. This antibody construct is composed of, at a minimum, a CR8033 heavy chain in combination with a light chain from a germline source.

Such expression methods and uses are known in the art.

Vector Genomes

In order to express a selected immunoglobulin domain, a nucleic acid molecule may be designed which contains codons which have been selected for optimal expression of the immunoglobulin polypeptides in a selected mammalian species, e.g., humans. Further, the nucleic acid molecule may include a heterologous leader sequence for each heavy chain and light chain of the selected antibody, which encodes the IL-2 signal leader peptide fused upstream of the heavy and chain polypeptides composed of the variable and constant regions. However, another heterologous leader sequence may be substituted for one or both of the IL-2 signal/leader peptide. Signal/leader peptides may be the same or different for each the heavy chain and light chain immunoglobulin constructs. These may be signal sequences which are natively found in an immunoglobulin (e.g., IgG), or may be from a heterologous source. Such heterologous sources may be a cytokine (e.g., IL-2, IL12, IL18, or the like), insulin, albumin, β-glucuronidase, alkaline protease or the fibronectin secretory signal peptides, or sequences from tissue specific secreted proteins, amongst others.

As used herein, an "expression cassette" refers to a nucleic acid sequence which comprises at least a first open reading frame (ORF) and optionally a second ORF. An ORF may contain two, three, or four antibody domains. For example, the ORF may contain a full-length heavy chain Alternatively, an ORF may contain one or two antibody domains. For example, the ORF may contain a heavy chain variable domain and a single heavy chain constant domain. In another example, the ORF may contain a light chain variable and a light chain constant region. Thus, an expression cassette may be designed to be bicistronic, i.e., to contain regulatory sequences which direct expression of the ORFs thereon from shared regulatory sequences. In this instance, the two ORFs are typically separated by a linker. Suitable linkers, such as an internal ribozyme binding site (IRES) and/or a furin-2a self-cleaving peptide linker (F2a) [see, e.g., Radcliffe and Mitrophanous, Gene Therapy (2004), 11, 1673-1674] are known in the art. Suitably, the ORF are operably linked to regulatory control sequences which direct expression in a target cell. Such regulatory control sequences may include a polyA, a promoter, and an enhancer. In order to facilitate co-expression from an AAV vector, at least one of the enhancer and/or polyA sequence may be shared by the first and second expression cassettes.

In one embodiment, the rAAV has packaged within the selected AAV capsid, a nucleic acid molecule comprising: an expression cassette comprising: a 5' AAV inverted terminal repeat sequence (ITR), a 5' UTR, an optional promoter, an optional Kozak sequence, a first signal peptide operably linked to a first immunoglobulin chain comprising a heavy chain, a linker sequence, a second signal peptide operably linked to a second immunoglobulin chain, and a 3' AAV ITR wherein one of and the second immunoglobulin is an immunoglobulin light chain, wherein said expression cassette co-expresses the immunoglobulin chains in a host cell under conditions which permit the chains to assemble into a functional antibody construct having the specificity of the antibody providing the heavy chain. In one embodiment, the heavy chain is a synthetic anti-influenza FI6v3 heavy chain immunoglobulin and the light chain is a kappa light chain from a germline.

In one embodiment, the expression cassette comprises AAV ITRs from a source different than the AAV capsid to form a pseudotyped AAV. In one embodiment, the expression cassette further comprises a constitutive promoter and an RGB polyA. Other suitable vector elements such as promoters and polyA sequences may be selected. For example, a minimal promoter and/or a minimal polyA may be selected in order to conserve space. Typically, in this embodiment, each promoter is located either adjacent (either to the left or the right (or 5' or 3')) to the enhancer sequence and the polyA sequences are located adjacent to the ITRs, with the ORFs there between. While it is preferred to express the heavy chain sequences first, the order of the ORFs may be varied, as may the immunoglobulin domains encoded thereby. For example, the light chain constant and variable sequences may be located to the left of the enhancer and the heavy chain may be encoded by ORFs located to the right of the enhancer. Alternatively, the heavy chain may be located to the left of the enhancer and the ORFs to the right of the enhancer by encode a light chain Alternatively, the opposite configuration is possible.

In another embodiment, the rAAV has packaged within the selected AAV capsid, a nucleic acid molecule comprising: a 5' AAV inverted terminal repeat sequence (ITR), a promoter, a 5' UTR, an optional Kozak sequence, an IL-2 signal peptide operably linked to an Fi6 immunoglobulin heavy chain, an F2a, an IL-2 signal peptide operably linked to a germline kappa light chain, and a 3' AAV ITR. In one embodiment, the AAV capsid is AAV9 or AAV8. In a further embodiment, the ITRs are from AAV2, or a different source which is different from the AAV capsid source.

Suitable regulatory control sequences may be selected and obtained from a variety of sources. In one embodiment, a minimal promoter and/or a minimal polyA may be utilized to conserve size.

As used herein, the term "minimal promoter" means a short DNA sequence comprised of a TATA-box and other sequences that serve to specify the site of transcription initiation, to which regulatory elements are added for control of expression. In one embodiment, a promoter refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. In one embodiment, the minimal promoter is a Cytomegalovirus (CMV) minimal promoter. In another embodiment, the minimal promoter is derived from human CMV (hCMV) such as the hCMV immediate early promoter derived minimal promoter (see, US 20140127749, and Gossen and Bujard (Proc. Natl. Acad. Sci. USA, 1992, 89: 5547-5551), which are incorporated herein by reference). In another embodiment, the minimal promoter is derived from a viral source such as, for example SV40 early or late promoters, cytomegalovirus (CMV) immediate early promoters, or Rous Sarcoma Virus (RSV) early promoters; or from eukaryotic cell promoters, for example, beta actin promoter (Ng, Nuc. Acid Res. 17:601-615, 1989; Quitsche et al., J. Biol. Chem. 264:9539-9545, 1989), GADPH promoter (Alexander, M. C. et al., Proc. Nat. Acad. Sci. USA 85:5092-5096, 1988, Ercolani, L. et al., J. Biol. Chem. 263:15335-15341, 1988), TK-1 (thymidine kinase) promoter, HSP (heat shock protein) promoters, UbB or UbC promoter, PGK, Ef1-alpha promoter or any eukaryotic promoter containing a TATA box (US Published Application No. 2014/0094392). In another embodiment, the minimal promoter includes a mini-promoter, such as the CLDNS mini-promoter described in US Published Application No. 2014/0065666. In another embodiment, the minimal promoter is the Thymidine Kinase (TK) promoter. In one embodiment, the minimal promoter is tissue specific, such as one of the muscle-cell specific promoters minimal TnISlow promoter, a minimal TnIFast promoter or a muscle creatine kinase promoter (US Published Application No. 2012/0282695). Each of these documents is incorporated herein by reference.

A recombinant AAV vector (AAV viral particle) may comprise, packaged within an AAV capsid, a nucleic acid molecule expressing a functional antibody as described in this specification. An expression cassette may contain regulatory elements for an open reading frame(s) within each expression cassette and the nucleic acid molecule may optionally contain additional regulatory elements.

The AAV vector may contain a full-length AAV 5' inverted terminal repeat (ITR) and a full-length 3' ITR. A shortened version of the 5' ITR, termed AITR, has been described in which the D-sequence and terminal resolution site (trs) are deleted. The abbreviation "sc" refers to self-complementary. "Self-complementary AAV" refers a construct in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

Where a pseudotyped AAV is to be produced, the ITRs are selected from a source which differs from the AAV source of the capsid. For example, AAV2 ITRs may be selected for use with an AAV capsid having a particular efficiency for a selected cellular receptor, target tissue or viral target. In one embodiment, the ITR sequences from AAV2, or the deleted version thereof (AITR), are used for convenience and to accelerate regulatory approval. However, ITRs from other AAV sources may be selected. Where the source of the ITRs is from AAV2 and the AAV capsid is from another AAV source, the resulting vector may be termed pseudotyped. However, other sources of AAV ITRs may be utilized.

A variety of AAV capsids have been described. Methods of generating AAV vectors have been described extensively in the literature and patent documents, including, e.g., WO 2003/042397; WO 2005/033321, WO 2006/110689; U.S. Pat. No. 7,588,772 B2. The source of AAV capsids may be selected from an AAV which targets a desired tissue. For example, suitable AAV may include, e.g., AAV9[U.S. Pat. No. 7,906,111; US 2011-0236353-A1], rh10 [WO 2003/042397] and/or hu37 [see, e.g., U.S. Pat. No. 7,906,111; US 2011-0236353-A1]. However, other AAV, including, e.g., AAV1, AAV2, AAV3, AAV4, AAV5, AAV6, AAV7, AAV8, [U.S. Pat. Nos. 7,790,449; 7,282,199] and others. However, other sources of AAV capsids and other viral elements may be selected, as may other immunoglobulin constructs and other vector elements.

Methods for generating and isolating AAV viral vectors suitable for delivery to a subject are known in the art. See, e.g., U.S. Pat. Nos. 7,790,449; 7,282,199; WO 2003/042397; WO 2005/033321, WO 2006/110689; and U.S. Pat. No. 7,588,772 B2]. In one system, a producer cell line is transiently transfected with a construct that encodes the transgene flanked by ITRs and a construct(s) that encodes rep and cap. In a second system, a packaging cell line that stably supplies rep and cap is transiently transfected with a construct encoding the transgene flanked by ITRs. In each of these systems, AAV virions are produced in response to infection with helper adenovirus or herpesvirus, requiring the separation of the rAAVs from contaminating virus. More recently, systems have been developed that do not require infection with helper virus to recover the AAV—the required helper functions (i.e., adenovirus E1, E2a, VA, and E4 or herpesvirus ULS, ULB, UL52, and UL29, and herpesvirus polymerase) are also supplied, in trans, by the system. In these newer systems, the helper functions can be supplied by transient transfection of the cells with constructs that encode the required helper functions, or the cells can be engineered to stably contain genes encoding the helper functions, the expression of which can be controlled at the transcriptional or posttranscriptional level. In yet another system, the transgene flanked by ITRs and rep/cap genes are introduced into insect cells by infection with baculovirus-based vectors. For reviews on these production systems, see generally, e.g., Zhang et al., 2009, "Adenovirus-adeno-associated virus hybrid for large-scale recombinant adeno-associated virus production," Human Gene Therapy 20:922-929, the contents of each of which is incorporated herein by reference in its entirety. Methods of making and using these and other AAV production systems are also described in the following U.S. patents, the contents of which is incorporated herein by reference in its entirety: U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065.

In one embodiment, the polyadenylation (poly(A)) signal is a minimal poly(A) signal, i.e., the minimum sequence required for efficient polyadenylation. In one embodiment, the minimal poly(A) is a synthetic poly(A), such as that described in Levitt et al, Genes Dev., 1989 Jul., 3(7):1019-25; and Xia et al, Nat Biotechnol. 2002 Oct.; 20(10):1006-10. Epub 2002 Sep 16. In another embodiment, the poly(A) is derived from the rabbit beta-globin poly(A). In one embodiment, the polyA acts bidirectionally (An et al, 2006, PNAS, 103(49): 18662-18667. In one embodiment, the poly(A) is derived from the SV40 early poly A signal sequence. Each of these documents is incorporated herein by reference.

Optionally, a single enhancer, or the same enhancer, may regulate the transcription of multiple heterologous genes in the plasmid construct. Various enhancers suitable for use in the invention are known in the art and include, for example, the CMV early enhancer, Hoxc8 enhancer, nPE1 and nPE2. Additional enhancers useful herein are described in Andersson et al, Nature, 2014 March, 507(7493):455-61, which is incorporated herein by reference. Still other enhancer elements may include, e.g., an apolipoprotein enhancer, a zebrafish enhancer, a GFAP enhancer element, and tissue specific enhancers such as described in WO 2013/1555222, woodchuck post hepatitis post-transcriptional regulatory element. Additionally, or alternatively, other, e.g., the hybrid human cytomegalovirus (HCMV)-immediate early (IE)-PDGR promoter or other promoter—enhancer elements may be selected. To enhance expression the other elements can be introns (like promega intron or chimeric chicken globin-human immunoglobulin intron). Other enhancers useful herein can be found in the Mammalian Promoter/Enhancer Database found at http://promoter_cdb_riken.ip/.

The constructs described herein may further contain other expression control or regulatory sequences such as, e.g., include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence; sequences that enhance protein stability; and when desired, sequences that enhance secretion of the encoded product. In the working examples below, the Kozak sequence used is: CCACCATG (nt (1988).(1992) of SEQ ID NO:1); however, other suitable sequences may be selected. A promoter may be selected from amongst a constitutive promoter, a tissue-specific promoter, a cell-specific promoter, a promoter responsive to physiologic cues, or a regulatable promoter [see, e.g., WO 2011/126868 and WO 2013/049492].

These control sequences are "operably linked" to the immunoglobulin construct gene sequences. As used herein, the term "operably linked" refers to both expression control sequences that are contiguous with the gene of interest and expression control sequences that act in trans or at a distance to control the gene of interest.

Examples of constitutive promoters suitable for controlling expression of the antibody domains include, but are not limited to chicken β-actin (CB) or beta actin promoters from other species, human cytomegalovirus (CMV) promoter, the early and late promoters of simian virus 40 (SV40), U6 promoter, metallothionein promoters, EFIα promoter, ubiquitin promoter, hypoxanthine phosphoribosyl transferase (HPRT) promoter, dihydrofolate reductase (DHFR) promoter (Scharfmann et al., Proc. Natl. Acad. Sci. USA 88:4626-4630 (1991), adenosine deaminase promoter, phosphoglycerol kinase (PGK) promoter, pyruvate kinase promoter phosphoglycerol mutase promoter, the β-actin promoter (Lai et al., Proc. Natl. Acad. Sci. USA 86: 10006-10010 (1989), UbB, UbC, the long terminal repeats (LTR) of Moloney Leukemia Virus and other retroviruses, the thymidine kinase promoter of Herpes Simplex Virus and other constitutive promoters known to those of skill in the art. Examples of tissue- or cell-specific promoters suitable for use in the present invention include, but are not limited to, endothelin-I (ET-I) and Flt-I, which are specific for endothelial cells, FoxJ1 (that targets ciliated cells).

Although less desired, inducible promoters suitable for controlling expression of the antibody domains include promoters responsive to exogenous agents (e.g., pharmacological agents) or to physiological cues may be utilized. These response elements include, but are not limited to a hypoxia response element (HRE) that binds HIF-Iα and β, a metal-ion response element such as described by Mayo et al. (1982, Cell 29:99-108); Brinster et al. (1982, Nature 296:39-42) and Searle et al. (1985, Mol. Cell. Biol. 5:1480-1489); or a heat shock response element such as described by Nouer et al. (in: Heat Shock Response, ed. Nouer, L., CRC, Boca Raton, Fla., pp167-220, 1991).

In one embodiment, expression of an open reading frame is controlled by a regulatable promoter that provides tight control over the transcription of the ORF (gene), e.g., a pharmacological agent, or transcription factors activated by a pharmacological agent or in alternative embodiments, physiological cues. Examples of regulatable promoters which are ligand-dependent transcription factor complexes that may be used include, without limitation, members of the nuclear receptor superfamily activated by their respective ligands (e.g., glucocorticoid, estrogen, progestin, retinoid, ecdysone, and analogs and mimetics thereof) and rTTA activated by tetracycline. Examples of such systems, include, without limitation, the ARGENT™ Transcriptional Technology (ARIAD Pharmaceuticals, Cambridge, Mass.). Examples of such promoter systems are described, e.g., in WO 2012/145572, which is incorporated by reference herein. In other embodiments, small RNA based switches are described in http://www_ncbi_nlm_nih_gov/pubmed/25605380.

Still other promoters may include, e.g., human cytomegalovirus (CMV) immediate-early enhancer/promoter, the SV40 early enhancer/promoter, the JC polymovirus promoter, myelin basic protein (MBP) or glial fibrillary acidic protein (GFAP) promoters, herpes simplex virus (HSV-1) latency associated promoter (LAP), rouse sarcoma virus (RSV) long terminal repeat (LTR) promoter, neuron-specific promoter (NSE), platelet derived growth factor (PDGF) promoter, hSYN, melanin-concentrating hormone (MCH) promoter, CBA, glial fibrilallary acidic protein (GFAP) promoter, matrix metalloprotein promoter (MPP), and the chicken beta-actin promoter. The promoters may the same or different for each expression cassette.

In cetain embodiments, the vector genomes each contain an immunoglobulin expression cassette flanked by inverted terminal repeats (ITRs). The expression cassettes contain coding sequences driven by a CB7 promoter, a hybrid between a cytomegalovirus (CMV) immediate early enhancer (C4) and the chicken beta actin promoter. Transcription from this promoter is enhanced by the presence of the chicken beta actin intron (CI). The 5' untranslated region (UTR) of the human c-myc gene is positioned upstream of the mAb coding region as a translational enhancer. The polyadenylation signal for the expression cassette is the rabbit beta-globin (RBG) polyA. Leader (signal) peptides precede both the heavy and light chains of the antibody and mediate the secretion of the antibody from the transduced cell. The heavy and light chains are separated by a linker containing the furin cleavage site and the FMDV 2A sequence. This linker mediates the post-translational cleavage of heavy and light chains and with the exception of a single amino acid substitution (the terminal lysine in the heavy chain is substituted with an arginine residue), is completely removed from the final mAb product.

In one embodiment, the vector comprises a constitutive promoter. In another embodiment, the 5' UTR is a truncated UTR from human c-myc gene. The linker sequence may be F2A or an IRES. The heavy signal peptide and the light signal peptide may be the same or different. In one embodiment the leader sequence is an interleukin (IL) IL-2 leader sequence, which may be the wild-type IL2 (MYRMQLLSCIALSLALVTNS, SEQ ID NO:24), such as used in the FI6v3 heavy chain, or a synthetic leader, such as the mutated IL2 used in the germline kappa light chain (MYRMQLLLLIALSLALVTNS, SEQ ID NO:5) or the mutated IL2 leader used for the CR8033 heavy chain (MRMQLLLLIALSLALVTNS, SEQ ID NO: 25). Other leader sequences including innate antibody signal peptides can be used, or other heterologous leaders. In one embodiment, a wild-type or synthetic polyA may be selected. As used herein a vector may be any suitable genetic element which transfects, transduces or infects a host cell and expresses the immunoglobulins which assemble into a functional antibody. Such vectors may be selected from a lentiviral vector, a baculovirus vector, a parvovirus vector, a plasmid, modified RNA, and a DNA molecule where mRNA and DNA may be in a form of nanoparticles.

In one embodiment, the vector genome for an AAV vector carrying the influenza A antibody comprises:

Inverted terminal repeats (ITR): AAV2 ITRs (GenBank #NC001401) represent the only cis sequences required for vector genome replication and packaging. An AAV having ITRs from a different source than its capsid are termed "pseudotyped". In certain embodiments, ITRs from a source other than AAV2 may be selected for this construct to generate another pseudotyped AAV. Alternatively, ITRs from the same source as the capsid may be selected.

Cytomegalovirus (CMV) immediate early enhancer (260 bp, C4; GenBank #K03104.1). In another embodiment, another enhancer may be selected. See, discussion of enhancers below.

Chicken beta-actin promoter (281 bp; CB; GenBank #X00182.1). In certain embodiments, another promoter may be selected. See, discussion of promoters below. In still other embodiments, multiple enhancers and/or promoters may be included. Chicken beta-actin intron: The 875 bp intron from the chicken beta actin gene (GenBank #X00182.1) is present in the vector expression cassette.

C-myc 5' UTR: Nucleotides 381-428 of Homo sapiens v-myc avian myelocytomatosis viral oncogene homolog (MYC) mRNA GenBank Accession #NM002467).

Leader (signal) peptide cDNA: A codon optimized cDNA sequence (http://www.uniprot.org/uniprot/P60568) preceding and in frame with the FI6 heavy chain. FI6v3 heavy variable chain cDNA: A codon optimized human cDNA sequence encoding a human heavy chain variable region anti-influenza variable region (GenBank Accession #AEL31303.1).

Constant heavy 1 (CH1) chain: A codon optimized cDNA encoding the protein sequence of human immunoglobulin heavy chain GenBank Accession #BAF64540.1 was synthesized.

FI6 Fc chain (CH2-3): A codon optimized cDNA encoding the human immunoglobulin fraction of GenBank Accession #2J6E_A with the exception of C-terminal lysine which was replaced with arginine and position 57, where aspartic acid was replaced glutamic acid).

Leader (signal) peptide cDNA: A codon optimized cDNA sequence which precedes the universal light chain (ILhyl described in [Zhang et al, cited above) was synthesized.

Universal light chain cDNA: A codon optimized human cDNA sequence (GeBank Accession #ACJ71709.1) was synthesized.

Constant light chain cDNA: A codon human sequence (GenBank Accession #AGH70219.1) was synthesized.

Furin recognition site: An Arginine-Lysine-Arginine-Arginine and codon optimized cDNA was synthesized. F2A linker: A 24 amino acid peptide derived from FMDV (GenBank #CAA2436.1) and codon optimized cDNA was synthesized.

Polyadenylation Signal: The 127 bp rabbit beta-globin polyadenylation signal (GenBank #V00882.1) provides cis sequences for efficient polyadenylation of the antibody mRNA.

In certain embodiments, the vector genome for an AAV vector carrying the influenza B antibody comprises: inverted terminal repeats (ITR): AAV2 ITRs; cytomegalovirus (CMV) immediate early enhancer; chicken beta-actin promoter; chicken beta-actin intron; truncated c-myc 5' UTR; leader (signal) peptide cDNA; CR8033 heavy variable chain cDNA; constant heavy 1 (CH1) chain: A codon optimized cDNA; CR8033 Fc chain (CH2-3); leader (signal) peptide cDNA; universal light chain cDNA; constant light chain cDNA; furin recognition site; F2A linker; polyadenylation signal.

In certain embodiments, the vector elements of the influenza A and/or influenza B may be varied. For example, the vector genome as illustrated above, but without the AAV ITRs, may be used in a different expression system (e.g., baculovirus, lentivirus, plasmid, naked DNA). Other suitable vector elements, including, e.g., promoters, enhancers, linkers, polyA, introns, for use in an AAV or non-AAV expression system are described herein.

The two or more ORF(s) carried by the nucleic acid molecule packaged within the vector may be expressed from two expression cassettes, one or both of which may be bicistronic.

The coding sequences for the selected immunoglobulin (e.g., heavy and/or light chain(s)) or other elements (e.g., leader sequences) may be obtained and/or synthesized. Methods for sequencing a nucleic acid (e.g., RNA and DNA) are known to those of skill in the art. Once the sequence of a nucleic acid is known, there are web-based and commercially available computer programs, as well as service based companies which back translate the amino acids sequences to nucleic acid coding sequences. See, e.g., backtranseq by EMBOSS, http://www_ebi_ac_uk/Tools/st/; Gene Infinity (http://www_geneinfinity_org/sms/sms_backtranslation_html); ExPasy (http://www_expasy_org/tools/). In one embodiment, the RNA and/or cDNA coding sequences are designed for optimal expression in human cells. Methods for synthesizing nucleic acids are known to those of skill in the art and may be utilized for all, or portions, of the nucleic acid constructs described herein.

Codon-optimized coding regions can be designed by various different methods. This optimization may be performed using methods which are available on-line (e.g., GeneArt,), published methods, or a company which provides codon optimizing services, e.g., as DNA2.0 (Menlo Park, Calif.). One codon optimizing algorithm is described, e.g., in US Patent Application No. WO 2015/012924, which is incorporated by reference herein. See also, e.g., US Patent Publication No. 2014/0032186 and US Patent Publication No. 2006/0136184. Suitably, the entire length of the open reading frame (ORF) for the product is modified. However, in some embodiments, only a fragment of the ORF may be altered. By using one of these methods, one can apply the frequencies to any given polypeptide sequence, and produce a nucleic acid fragment of a codon-optimized coding region which encodes the polypeptide.

For use in producing an AAV viral vector (e.g., a recombinant (r) AAV), the expression cassettes can be carried on any suitable vector, e.g., a plasmid, which is delivered to a packaging host cell. The plasmids useful in this invention may be engineered such that they are suitable for replication and packaging in prokaryotic cells, mammalian cells, or both. Suitable transfection techniques and packaging host cells are known and/or can be readily designed by one of skill in the art.

Methods for generating and isolating AAVs suitable for use as vectors are known in the art. See generally, e.g., Grieger & Samulski, 2005, "Adeno-associated virus as a gene therapy vector: Vector development, production and clinical applications," *Adv. Biochem. Engin/Biotechnol.* 99: 119-145; Buning et al., 2008, "Recent developments in adeno-associated virus vector technology," *J. Gene Med.* 10:717-733; and the references cited below, each of which is incorporated herein by reference in its entirety. For packaging a transgene into virions, the ITRs are the only AAV components required in cis in the same construct as the nucleic acid molecule containing the expression cassettes. The cap and rep genes can be supplied in trans.

In one embodiment, the expression cassettes described herein are engineered into a genetic element (e.g., a shuttle plasmid) which transfers the immunoglobulin construct sequences carried thereon into a packaging host cell for production a viral vector. In one embodiment, the selected genetic element may be delivered to an AAV packaging cell by any suitable method, including transfection, electroporation, liposome delivery, membrane fusion techniques, high velocity DNA-coated pellets, viral infection and protoplast fusion. Stable AAV packaging cells can also be made. Alternatively, the expression cassettes may be used to generate a viral vector other than AAV, or for production of mixtures of antibodies in vitro. The methods used to make such constructs are known to those with skill in nucleic acid manipulation and include genetic engineering, recombinant engineering, and synthetic techniques. See, e.g., Molecular Cloning: A Laboratory Manual, ed. Green and Sambrook, Cold Spring Harbor Press, Cold Spring Harbor, N.Y. (2012).

AAV Vectors

As used herein, "AAV9 capsid" refers to the AAV9 having the amino acid sequence of GenBank accession:AAS99264, which is incorporated by reference herein. Some variation from this encoded sequence is encompassed by the present invention, which may include sequences having about 99% identity to the referenced amino acid sequence in GenBank accession:AAS99264 and U.S. Pat. No. 7,906,111 (also WO 2005/033321) (i.e., less than about 1% variation from the referenced sequence. However, in other embodiments, other variants of AAV9, or AAV9 capsids having at least about 95% identity to the above-referenced sequences may be selected. Methods of generating the capsid, coding sequences therefore, and methods for production of rAAV viral vectors have been described. See, e.g., Gao, et al, Proc. Natl. Acad. Sci. U.S.A. 100 (10), 6081-6086 (2003) and US 2013/0045186A1.

The term "AAV9 intermediate" or "AAV9 vector intermediate" refers to an assembled rAAV capsid which lacks the desired genomic sequences packaged therein. These may also be termed an "empty" capsid. Such a capsid may contain no detectable genomic sequences of an expression cassette, or only partially packaged genomic sequences which are insufficient to achieve expression of the gene product. These empty capsids are non-functional to transfer the gene of interest to a host cell.

The recombinant adeno-associated virus (AAV) described herein may be generated using techniques which are known. See, e.g., WO 2003/042397; WO 2005/033321, WO 2006/110689; U.S. Pat. No. 7,588,772 B2. Such a method involves culturing a host cell which contains a nucleic acid sequence encoding an AAV capsid; a functional rep gene; a expression cassette composed of, at a minimum, AAV inverted terminal repeats (ITRs) and a transgene; and sufficient helper functions to permit packaging of the expression cassette into the AAV capsid protein.

Briefly, cells are manufactured in a suitable cell culture (e.g., HEK 293) cells. Methods for manufacturing the gene therapy vectors described herein include methods well known in the art such as generation of plasmid DNA used for production of the gene therapy vectors, generation of the vectors, and purification of the vectors. In some embodiments, the gene therapy vector is an AAV vector and the plasmids generated are an AAV cis-plasmid encoding the AAV genome and the gene of interest, an AAV trans-plasmid containing AAV rep and cap genes, and an adenovirus helper plasmid. The vector generation process can include method steps such as initiation of cell culture, passage of cells, seeding of cells, transfection of cells with the plasmid DNA, post-transfection medium exchange to serum free medium, and the harvest of vector-containing cells and culture media. The harvested vector-containing cells and culture media are referred to herein as crude cell harvest.

The crude cell harvest may thereafter be subject method steps such as concentration of the vector harvest, diafiltration of the vector harvest, microfluidization of the vector harvest, nuclease digestion of the vector harvest, filtration of microfluidized intermediate, crude purification by chromatography, crude purification by ultracentrifugation, buffer exchange by tangential flow filtration, and/or formulation and filtration to prepare bulk vector.

A two-step affinity chromatography purification at high salt concentration followed anion exchange resin chromatography are used to purify the vector drug product and to remove empty capsids. These methods are described in more detail in US Patent Application No. 62/322,071, filed Apr. 13, 2016 and US Patent Application No. 62/226,357, filed Dec. 11, 2015 and entitled "Scalable Purification Method for AAV9", which is incorporated by reference herein. Purification methods for AAV8 are US Patent Application No. 62/322,098, filed Apr. 13, 2016 and US Patent Application No. 62/266,341, filed Dec. 11, 2015, and rh10, US Patent Application No. 62/322,055, filed Apr. 13, 2016 and US Patent Application No. 62/266,347, entitled "Scalable Purification Method for AAVrh10", filed Dec. 11, 2015, and for AAV1, US Patent Application No. 62/322,083, filed Apr. 13, 2016 and US Patent Application No 62/26,351, for "Scalable Purification Method for AAV1", filed Dec. 11, 2015, are all incorporated by reference herein.

To calculate empty and full particle content, VP3 band volumes for a selected sample (e.g., in examples herein an iodixanol gradient-purified preparation where #of GC=#of particles) are plotted against GC particles loaded. The resulting linear equation (y=mx+c) is used to calculate the number of particles in the band volumes of the test article peaks. The number of particles (pt) per 20 µL loaded is then multiplied by 50 to give particles (pt)/mL. Pt/mL divided by GC/mL gives the ratio of particles to genome copies (pt/GC). Pt/mL—GC/mL gives empty pt/mL. Empty pt/mL divided by pt/mL and ×100 gives the percentage of empty particles.

Generally, methods for assaying for empty capsids and AAV vector particles with packaged genomes have been known in the art. See, e.g., Grimm et al., *Gene Therapy* (1999) 6:1322-1330; Sommer et al., *Molec. Ther.* (2003) 7:122-128. To test for denatured capsid, the methods include subjecting the treated AAV stock to SDS-polyacrylamide gel electrophoresis, consisting of any gel capable of separating the three capsid proteins, for example, a gradient gel containing 3-8% Tris-acetate in the buffer, then running the gel until sample material is separated, and blotting the gel onto nylon or nitrocellulose membranes, preferably nylon. Anti-AAV capsid antibodies are then used as the primary antibodies that bind to denatured capsid proteins, preferably an anti-AAV capsid monoclonal antibody, most preferably the B1 anti-AAV-2 monoclonal antibody (Wobus et at. *J. Vivol.* (2000) 74:9281-9293). A secondary antibody is then used, one that binds to the primary antibody and contains a means for detecting binding with the primary antibody, more preferably an anti-IgG antibody containing a detection molecule covalently bound to it, most preferably a sheep anti-mouse IgG antibody covalently linked to horseradish peroxidase. A method for detecting binding is used to semi-quantitatively determine binding between the primary and secondary antibodies, preferably a detection method capable of detecting radioactive isotope emissions, electromagnetic radiation, or colorimetric changes, most preferably a chemiluminescence detection kit. For example, for SDS-PAGE, samples from column fractions can be taken and heated in SDS-PAGE loading buffer containing reducing agent (e.g., DTT), and capsid proteins were resolved on pre-cast gradient polyacrylamide gels (e.g., Novex). Silver staining may be performed using SilverXpress (Invitrogen, Calif.) according to the manufacturer's instructions or other suitable staining method, i.e. SYPRO ruby or coomassie stains. In one embodiment, the concentration of AAV vector genomes (vg) in column fractions can be measured by quantitative real time PCR (Q-PCR). Samples are diluted and digested with DNase I (or another suitable nuclease) to remove exogenous DNA. After inactivation of the nuclease, the samples are further diluted and amplified using primers and a TaqMan™ fluorogenic probe specific for the DNA sequence between the primers. The number of cycles required to reach a defined level of fluorescence (threshold cycle, Ct) is measured for each sample on an Applied Biosystems Prism 7700 Sequence Detection System. Plasmid DNA containing identical sequences to that contained in the AAV vector is employed to generate a standard curve in the Q-PCR reaction. The cycle threshold (Ct) values obtained from the samples are used to determine vector genome titer by normalizing it to the Ct value of the plasmid standard curve. End-point assays based on the digital PCR can also be used.

In one aspect, an optimized q-PCR method is used which utilizes a broad spectrum serine protease, e.g., proteinase K (such as is commercially available from Qiagen). More particularly, the optimized qPCR genome titer assay is similar to a standard assay, except that after the DNase I digestion, samples are diluted with proteinase K buffer and treated with proteinase K followed by heat inactivation. Suitably samples are diluted with proteinase K buffer in an amount equal to the sample size. The proteinase K buffer may be concentrated to 2 fold or higher. Typically, proteinase K treatment is about 0.2 mg/mL, but may be varied from 0.1 mg/mL to about 1 mg/mL. The treatment step is generally conducted at about 55° C. for about 15 minutes, but may be performed at a lower temperature (e.g., about 37° C. to about 50° C.) over a longer time period (e.g., about 20 minutes to about 30 minutes), or a higher temperature (e.g., up to about 60° C.) for a shorter time period (e.g., about 5 to 10 minutes). Similarly, heat inactivation is generally at about 95° C. for about 15 minutes, but the temperature may be lowered (e.g., about 70 to about 90° C.) and the time extended (e.g., about 20 minutes to about 30 minutes). Samples are then diluted (e.g., 1000 fold) and subjected to TaqMan analysis as described in the standard assay.

Additionally, or alternatively, droplet digital PCR (ddPCR) may be used. For example, methods for determining single-stranded and self-complementary AAV vector genome titers by ddPCR have been described. See, e.g., M. Lock et al, Hu Gene Therapy Methods, Hum Gene Ther Methods. 2014 April; 25(2):115-25. doi: 10.1089/hgtb.2013.131. Epub 2014 Feb. 14.

In brief, the method for separating rAAV9 particles having packaged genomic sequences from genome-deficient AAV9 intermediates involves subjecting a suspension comprising recombinant AAV9 viral particles and AAV 9 capsid intermediates to fast performance liquid chromatography, wherein the AAV9 viral particles and AAV9 intermediates are bound to a strong anion exchange resin equilibrated at a pH of 10.2, and subjected to a salt gradient while monitoring eluate for ultraviolet absorbance at about 260 and about 280. Although less optimal for rAAV9, the pH may be in the range of about 10.0 to 10.4. In this method, the AAV9 full capsids are collected from a fraction which is eluted when the ratio of A260/A280 reaches an inflection point. In one example, for the Affinity Chromatography step, the diafiltered product may be applied to a Capture Select™ Poros-AAV2/9 affinity resin (Life Technologies) that efficiently captures the AAV2/9 serotype. Under these ionic conditions, a significant percentage of residual cellular DNA and proteins flow through the column, while AAV particles are efficiently captured.

A suitable formulation is an aqueous suspension buffered to a physiologically compatible pH and salt concentration. Optionally, one or more surfactants are present in the formulation.

A suitable surfactant, or combination of surfactants, may be selected from among non-ionic surfactants that are non-toxic. In one embodiment, a difunctional block copolymer surfactant terminating in primary hydroxyl groups is selected, e.g., such as Pluronic® F68 [BASF], also known as Poloxamer 188, which has a neutral pH, has an average molecular weight of 8400. Other surfactants and other Poloxamers may be selected, i.e., nonionic triblock copolymers composed of a central hydrophobic chain of polyoxypropylene (poly(propylene oxide)) flanked by two hydrophilic chains of polyoxyethylene (poly(ethylene oxide)), SOLUTOL HS 15 (Macrogol-15 Hydroxystearate), LABRASOL (Polyoxy capryllic glyceride), polyoxy 10 oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits×100 give the approximate molecular mass of the polyoxypropylene core, and the last digit×10 gives the percentage polyoxyethylene content. In one embodiment Poloxamer 188 is selected. The surfactant may be present in an amount up to about 0.0005% to about 0.001% of the suspension.

Uses and Regimens

In one embodiment, a method of treating influenza and/or preventing infection with influenza virus comprising co-administering the synthetic FI6v3 antibody and synthetic CR8033 antibody provided herein. Optionally, such a passive immunization regimen may be combined with a traditional vaccine, with an additional anti-influenza antibody, or with other anti-viral ingredients may be selected.

In certain embodiments, the two antibodies are co-expressed from different rAAV9 vectors. In another embodiment, an rAAV-mediated artificial antibody delivery is combined with a different antibody expression system.

The vectors are preferably suspended in a physiologically compatible carrier, for administration to a human or non-human mammalian patient. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, maltose, and water. The selection of the carrier is not a limitation of the present invention. Optionally, the compositions of the invention may contain, in addition to the rAAV and carrier(s), other conventional pharmaceutical ingredients, such as preservatives, or chemical stabilizers.

In certain embodiments, the two different vector stocks (e.g., rAAV9.FI6v3+rAAV9.CR8033) are formulated separately. In such an embodiment, they may be delivered separately, but substantially simultaneously with each other, e.g., within minutes to about 1 hour. In certain embodiments, the two different vector stocks are admixed and combined into a single composition for administration. Whether delivered separately or in a combination suspension, the two vector stocks are admixed in a ratio of about 1:1 based on genome copies. In other embodiments, this ratio may be altered, e.g., from about 3:1, about 2:1, to about 1:2, based on total genome copies.

In certain embodiments, the rAAV9 formulation is a suspension containing an effective amount of AAV vector suspended in phosphate-buffered saline (PBS) with total concentration of about 200 mM, 0.001% (w/v) Pluronic F68 and 5% glycerol. Suitably, the formulation is adjusted to a physiologically acceptable pH, e.g., in the range of pH 6 to 9, or pH 6.5 to 8, pH 7.0 to 7.7, or pH 7.2 to 7.8. However, other pHs within the broadest ranges and these subranges may be selected for other route of delivery.

In one embodiment, the formulation may contain, e.g., a concentration of at least about $1 \times 10^9$ GC/mL to $3 \times 10^{13}$ GC/mL as measured by oqPCR or digital droplet PCR (ddPCR) as described in, e.g., M. Lock et al, Hu Gene Therapy Methods, Hum Gene Ther Methods. 2014 April; 25(2):115-25. doi: 10.1089/hgtb.2013.131. Epub 2014 Feb. 14, which is incorporated herein by reference.

In certain embodiments, a composition as provided herein is formulated for intranasal delivery. The invention encompasses products including kits which include an intranasal delivery device and a container for the composition of the invention, optionally with other components, e.g., diluents, etc.

In certain embodiments, the intranasal delivery device provides an spay atomizer which delivers a mist of particles having an average size range of about 30 microns to about 100 microns in size. In certain embodiments, the average size range is about 10 microns to about 50 microns. Suitable devices have been described in the literature and some are commercially available, e.g., the LMA MAD NASAL™ (Teleflex Medical; Ireland); Teleflex VaxlNator™ (Teleflex Medical; Ireland); Controlled Particle Dispersion® (CPD) from Kurve Technologies. See, also, PG Djupesland, Drug Deliv and Transl. Res (2013) 3: 42-62. In certain embodiments, the particle size and volume of delivery is controlled in order to preferentially target nasal epithelial cells and minimize targeting to the lung. In other embodiments, the mist of particles is about 0.1 micron to about 20 microns, or less, in order to deliver to lung cells. Such smaller particle sizes may minimize retention in the nasal epithelium.

Any suitable method or route can be used to administer an AAV-containing composition as described herein, and optionally, to co-administer other active drugs or therapies in conjunction with the AAV-mediated antibodies described herein. Routes of administration include, for example, systemic, oral, intravenous, intraperitoneal, subcutaneous, or intramuscular administration.

In one embodiment, a frozen composition is provided which contains an rAAV in a buffer solution as described herein, in frozen form. Optionally, one or more surfactants (e.g., Pluronic F68), stabilizers or preservatives is present in this composition. Suitably, for use, a composition is thawed and titrated to the desired dose with a suitable diluent, e.g., sterile saline or a buffered saline.

Optionally, a composition described herein may be used in combination with other anti-viral medications and/or vaccines against other viral targets, including other influenza vaccines, including: Influenza A, Influenza B, and Influenza C. The type A viruses are the most virulent human pathogens. The serotypes of influenza A which have been associated with pandemics include, H1N1, which caused Spanish Flu in 1918, and Swine Flu in 2009; H2N2, which caused Asian Flu in 1957; H3N2, which caused Hong Kong Flu in 1968; H5N1, which caused Bird Flu in 2004; H7N7; H1N2; H9N2; H7N2; H7N3; and H1ON7. Broadly neutralizing antibodies against influenza A have been described. As used herein, a "broadly neutralizing antibody" refers to a neutralizing antibody which can neutralize multiple strains from multiple subtypes. For example, CR6261 [The Scripps Institute/Crucell]has been described as a monoclonal antibody that binds to a broad range of the influenza virus including the 1918 "Spanish flu" (SC1918/H1) and to a virus of the H5N1 class of avian influenza that jumped from chickens to a human in Vietnam in 2004 (Viet04/H5). CR6261 recognizes a highly conserved helical region in the membrane-proximal stem of hemagglutinin, the predominant protein on the surface of the influenza virus. This antibody is described in WO 2010/130636, incorporated by reference herein. Another neutralizing antibody, F10 [XOMA Ltd] has been described as being useful against H1N1 and HSN1. [Sui et al, Nature Structural and Molecular Biology (Sui, et al. 2009, 16(3):265-73)] Other antibodies against influenza, e.g., Fab28 and Fab49, may be selected. See, e.g., WO 2010/140114 and WO 2009/115972, which are incorporated by reference. Still other antibodies, such as those described in WO 2010/010466, US Published Patent Publication US/2011/076265, and WO 2008/156763, may be readily selected.

Methods for using these rAAV, e.g., for passive immunization are described, e.g., in WO 2012/145572. Other methods of delivery and uses will be apparent to one of skill in the art. For example, a regimen as described herein may comprise, in addition to one or more of the combinations described herein, further combination with one or more of a biological drug, a small molecule drug, a chemotherapeutic agent, immune enhancers, radiation, surgery, and the like. A biological drug as described herein, is based on a peptide, polypeptide, protein, enzyme, nucleic acid molecule, vector (including viral vectors), or the like.

In a combination therapy, the AAV-delivered immunoglobulin construct described herein is administered before, during, or after commencing therapy with another agent, e.g., anti-viral therapy, antibiotics, as well as any combination thereof, i.e., before and during, before and after, during and after, or before, during and after commencing the therapy. For example, the AAV can be administered between 1 and 30 days, preferably 3 and 20 days, more preferably between 5 and 12 days before commencing therapy.

As described above, the term "about" when used to modify a numerical value means a variation of ±10%, unless otherwise specified.

As used throughout this specification and the claims, the terms "comprise" and "contain" and its variants including, "comprises", "comprising", "contains" and "containing", among other variants, is inclusive of other components, elements, integers, steps and the like. The term "consists of" or "consisting of" are exclusive of other components, elements, integers, steps and the like.

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, 91%, 92%, 93%, 94%, 95%, 96%, 97%, 98%, 99%, or higher identity over a specified region (e.g., any one of the modified ORFs provided herein when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). As another example, polynucleotide sequences can be compared using Fasta, a program in GCG Version 6.1. Fasta provides alignments and percent sequence identity of the regions of the best overlap between the query and search sequences. For instance, percent sequence identity between nucleic acid sequences can be determined using Fasta with its default parameters (a word size of 6 and the NOPAM factor for the scoring matrix) as provided in GCG Version 6.1, herein incorporated by reference. Generally, these programs are used at default settings, although one skilled in the art can alter these settings as needed. Alternatively, one of skill in the art can utilize another algorithm or computer program that provides at least the level of identity or alignment as that provided by the referenced algorithms and programs. This definition also refers to, or can be applied to, the compliment of a sequence. The definition also includes sequences that have deletions and/or additions, as well as those that have substitutions. As described below, the preferred algorithms can account for gaps and the like. Preferably, identity exists over a region that is at least about 25, 50, 75, 100, 150, 200 amino acids or nucleotides in length, and oftentimes over a region that is 225, 250, 300, 350, 400, 450, 500 amino acids or nucleotides in length or over the full-length of an amino acid or nucleic acid sequences.

Typically, when an alignment is prepared based upon an amino acid sequence, the alignment contains insertions and deletions which are so identified with respect to a reference AAV sequence and the numbering of the amino acid residues is based upon a reference scale provided for the alignment. However, any given AAV sequence may have fewer amino acid residues than the reference scale. In the present invention, when discussing the parental sequence, the term "the same position" or the "corresponding position" refers to the amino acid located at the same residue number in each of the sequences, with respect to the reference scale for the aligned sequences. However, when taken out of the alignment, each of the proteins may have these amino acids located at different residue numbers. Alignments are performed using any of a variety of publicly or commercially available Multiple Sequence Alignment Programs. Sequence alignment programs are available for amino acid sequences, e.g., the "Clustal X", "MAP", "PIMA", "MSA", "BLOCKMAKER", "MEME", and "MatchBox" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, *Nucl. Acids. Res*., "A comprehensive comparison of multiple sequence alignments", 27(13): 2682-2690 (1999).

As used herein, an "effective amount" refers to the amount of the rAAV9 composition which delivers and expresses in the target cells an amount of anti-influenza antibodies sufficient to reduce or prevent influenza infection. An effective amount may be determined based on an animal model, rather than a human patient. Examples of a suitable murine model are described herein.

As used herein, the term "patient" generally refers to a human diagnosed or at-risk for infection with influenza. Such a patient may also be referred to herein as a "subject". The term "subject" may also refer to non-human animals, e.g., cats, dogs, and non-human primates.

A "functional antibody" may be an antibody or immunoglobulin which binds to a selected target (e.g., an antigen on a cancer cell or a pathogen, such as a virus, bacteria, or parasite) with sufficient binding affinity to effect a desired physiologic result, which may be protective (e.g., passive immunization) or therapeutic.

As used herein, an "immunoglobulin domain" refers to a domain of an antibody heavy chain or light chain as defined with reference to a conventional, full-length antibody. More particularly, a full-length antibody contains a heavy (H) chain polypeptide which contains four domains: one N-terminal variable (VH) region and three C-terminal constant (CH1, CH2 and CH3) regions and a light (L) chain polypeptide which contains two domains: one N- terminal variable (VL) region and one C-terminal constant (CL) region. An Fc region may contain two domains (CH2-CH3). A Fab region may contain one constant and one variable domain for each the heavy and light chains. Constant domain allotypes suitable for those constructs may include, e.g., G1m17.1 and Glm3.

As used herein, "different specificities" indicates that the referenced immunoglobulin constructs (e.g., a full-length antibody, a heavy chain, or other construct capable of binding a specific target) bind to different target sites. These may refer to different targets on the same antigen, different strains of the same pathogen (e.g., different viral strains) or to different antigens.

The "same specificity" refers to the ability of the immunoglobulin to bind to specific target site which may be present on multiple strains of a pathogen (e.g., influenza virus) or for a single, or subset of strains, of the virus or other pathogen. Suitably, these specificities are such that there is no significant or measurable binding to non-target sites.

The term "heterologous" when used with reference to a protein or a nucleic acid indicates that the protein or the nucleic acid comprises two or more sequences or subsequences which are not found in the same relationship to each other in nature. For instance, the nucleic acid is typically recombinantly produced, having two or more sequences from unrelated genes arranged to make a new functional nucleic acid. For example, in one embodiment, the nucleic acid has a promoter from one gene arranged to direct the expression of a coding sequence from a different gene. Thus, with reference to the coding sequence, the promoter is heterologous. The term "heterologous light chain" is a light chain containing a variable domain and/or constant domain from an antibody which has a different target specificity from the specificity of the heavy chain.

As used throughout the specification, the term "a" or "an" refers to one or more. As such, the terms "a" (or "an"), "one or more," and "at least one" are used interchangeably herein.

Unless defined otherwise in this specification, technical and scientific terms used herein have the same meaning as commonly understood by one of ordinary skill in the art and by reference to published texts, which provide one skilled in the art with a general guide to many of the terms used in the present application.

The following examples illustrate methods for production and use of a mixture of AAV2/9 vectors in which one expresses a broadly neutralizing antibody to influenza A, called FI6; the other expresses a broadly neutralizing antibody to influenza B, called CR8033. In one embodiment, the composition termed herein GTP101 is formulated in phosphate-buffered saline (PBS) with total salt concentration brought to 200 mM, 0.001% (w/v) pluronic F68 and 5% glycerol. AAV2/9 will be administered intranasally (IN) after dilution into sterile buffer solution at 4 dose levels. The initial dose levels have been chosen based on preclinical efficacy data, and will be refined based on nonclinical safety assessments, with the highest dose limited by the concentration that can be achieved without AAV vector particle aggregating. Doses range from $3 \times 10^{12}$ to $2.4 \times 10^{13}$ genome copies (GC) administered as 4×0.2 ml per nostril via an intranasal mucosal atomization device (IMAD). It will be understood that the invention encompasses variations on these illustrative studies. For example, other means for intranasal administration may be used, other doses, volumes, and other regimens. Additionally, the composition may be adapted for other routes of administration.

The following examples are illustrative only and are not a limitation on the invention described herein.

EXAMPLE 1

AAV Vectors

AAV9 vectors expressing the heavy and light chains of FI6v3 and CR8033 monoclonal antibodies under the control of a hybrid cytomegalovirus enhancer chicken β-actin promoter were designed, cloned and packaged. The cis-plasmids used to construct each vector used in the following studies are provided in SEQ ID NO: 1 (FI6v3) and SEQ ID NO: 8 (CR8033), which are incorporated by reference with their features. The AAV9 vectors were generated using triple transfection of human HEK 293 MCB cells using techniques which were previously described, e.g., in US Patent Published Application No. US 2009/0275107; see, also, M. Lock et al, Hum Gene Ther, 2010; 21(10):1259-1271

The human HEK 293 MCB cells are transfected with: (i) the vector genome plasmids, (ii) an AAV helper plasmid termed pAAV2/9.KanR containing the AAV rep2 and cap 9 wild-type genes and (iii) a helper adenovirus plasmid termed pAdAF6(Kan). The size of the GTP101 packaged vector genomes are 1) AAV-FI6: 4650nt. and 2) AAV-CR8033: 4585nt. Other methods can also be used, utilizing producer cell lines of baculovirus systems. Alternative cis-plasmids and vectors may be generated using the other coding sequences provided herein.

A. GTP101 AAV Vector Genome Plasmid 1: pAAV.CB7.CI.F16.RBG

Figure 7A:
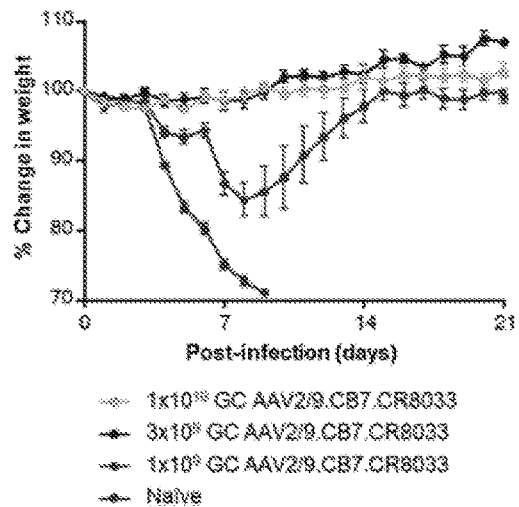
FIG. 7A and FIG. 7B show the determination of the MED of AAV2/9.CB7.CR8033 required for protection against challenge with B/Lee/40.
Figure 7B:
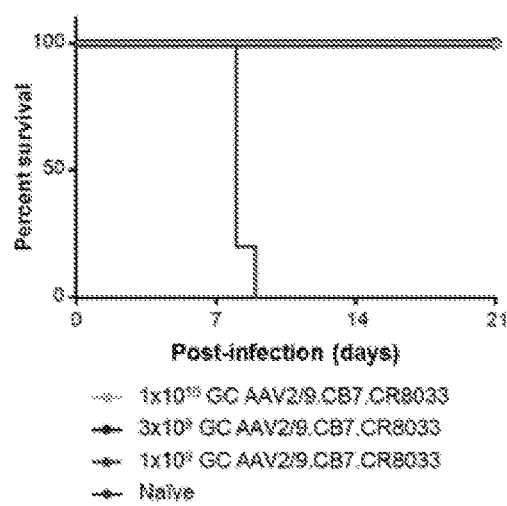
Figure 8:
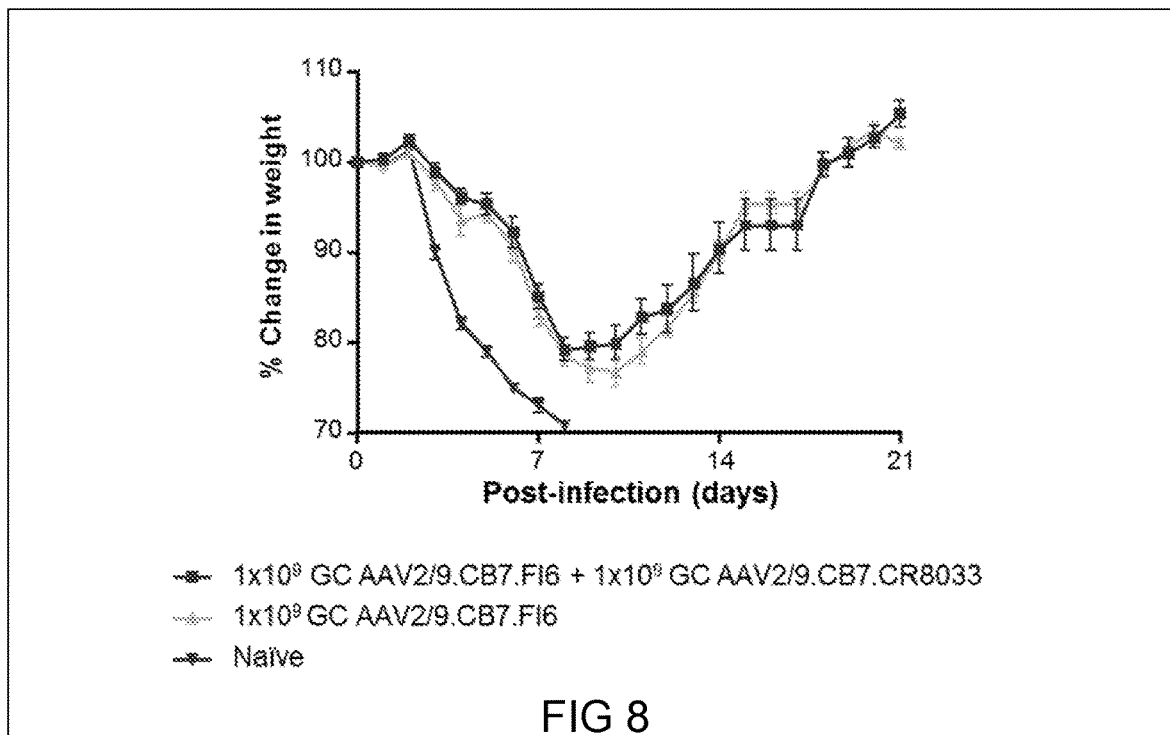
FIG. 8 shows the effect of mixing two AAV vectors on protection against challenge with influenza A (PR8). Mice were dosed with either $1\times10^9$ GC of AAV2/9.CB7.FI6 (triangles) or with a mixture of $1\times10^9$ GC of AAV2/9.CB7.FI6 and $1\times10^9$ GC of AAV2/9.CB7.CR8033 (squares). Mice were challenged 14 days later with $5LD_{50}$ PR8 (influenza A). Mice were euthanized when they appeared in distress or their body weight declined ≥30%.
Figure 9:
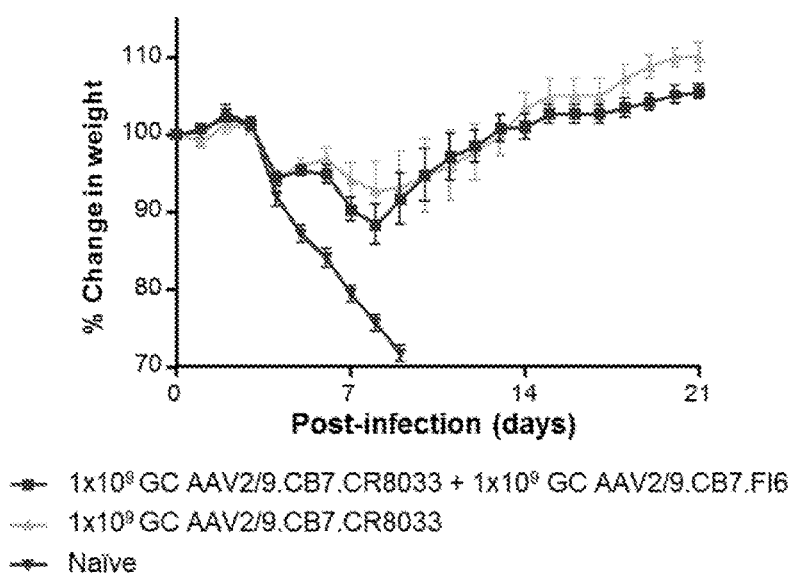
FIG. 9 shows the effect of mixing two AAV vectors on protection against challenge with influenza B. Mice were dosed with either $1\times10^9$ GC of AAV2/9.CB7.CR8033 (triangles) or with a mixture of $1\times10^9$ GC of AAV2/9.CB7.CR8033 and $1\times10^9$ GC AAV2/9.CB7.FI6 (squares). Mice were challenged 14 days later with $5LD_{50}$ B/Lee/40 (influenza B). Mice were euthanized when they appeared in distress or their body weight declined ≥30%.

The AAV-FI6 mAb vector genome plasmid pAAV.CB7.CI.FI6.RBG (p3193) is 7,471 bp in size (FIG. 7.2). The vector genome derived from this plasmid is a single-stranded DNA genome with AAV2 derived ITRs flanking the mAb expression cassette. The FI6 coding sequences encode a mAb specific for influenza A. Expression from the transgene cassettes is driven by a CB7 promoter, a hybrid between a cytomegalovirus (CMV) immediate early enhancer (C4) and the chicken beta actin promoter, while transcription from this promoter is enhanced by the presence of the chicken beta actin intron (CI). The 5' untranslated region (UTR) of the human c-myc gene is positioned upstream of the mAb coding region as a translational enhancer. The polyA signal for the expression cassette is the rabbit beta-globin (RBG) polyA. Leader (signal) peptides precede both the heavy and light chains of the antibody and mediate the secretion of the antibody from the transduced cell. The heavy and light chains are separated by a linker containing the furin cleavage site and the FMDV 2A sequence. This linker mediates the post-translational cleavage of heavy and light chains and with the exception of a single amino acid substitution (the terminal lysine in the heavy chain is substituted with an arginine residue), is completely removed from the final mAb product. The antibody translation cassette including 5' UTR and codon optimized mAb coding sequence was de novo synthesized and subcloned into pZac2.1 to make p3191. The gene cassette was subsequently shuttled into CB7 backbone, pN406 using NheI/NotI enzymes to replace the polylinker with the antibody translation cassette to give pAAV.CB7.CI.FI6.RBG (p3193). All component parts of the plasmid have been verified by direct sequencing by Qiagen Genomic Services.

B. GTP101 AAV Vector Genome Plasmid 2: pAAV.CB7.CI.CR8033.RBGG

The AAV-CR8033 mAb vector genome plasmid pAAV.CB7.CI.CR8033.RBG (p3523) will be 7,462 bp in size. The vector genome derived from this plasmid is a single-stranded DNA genome with AAV2 derived inverted terminal repeats (ITR) flanking the mAb expression cassette. The CR8033 coding sequences encode a mAb specific for influenza B. Expression from the transgene cassettes is driven by a CB7 promoter, a hybrid between a cytomegalovirus (CMV) immediate early enhancer (C4) and the modified chicken beta actin promoter, while transcription from this promoter is enhanced by the presence of the chicken beta actin intron (CI). The truncated 5' UTR of the human c-myc gene is positioned upstream of the mAb coding region as a translational enhancer. The polyA signal for the expression cassette is the rabbit beta-globin (RBG) polyA. Leader (signal) peptides precede both the heavy and light chains of the antibody and mediate the secretion of the antibody from the transduced cell. The heavy and light chains are separated by a linker containing the furin cleavage site and the FMDV 2A sequence. This linker mediates the post-translational cleavage of heavy and light chains and with the exception of a single amino acid substitution (the 5 terminal lysine in the heavy chain is substituted with an arginine residue), is completely removed from the final mAb product. The antibody translation cassette including the 5' untranslated region and codon optimized mAb coding sequence encoding the TCN032 mAb was de novo synthesized, and subcloned into pZac2.1 to make p3187. The light chain of TCN032 was replaced with the "universal" light chain sourced from pAAV.CB7.CI.FI6.RBG (p3193) described above using EcoRV/BsiWI enzyme sites. The CR8033 heavy variable chain coding sequence has been codon optimized, de-novo synthesized and will be used to replace the TCNO32 heavy variable chain via SphI/SalI restriction sites. The entire translational cassette will be shuttled into a CB7 promoter backbone plasmid, pN437 using SphI/NotI enzymes to replace the TCNO32 translational cassette with CR8033 translation cassette and generate the plasmid pAAV.CB7.CI.CR8033.RBG (p3523). All component parts of the plasmid were verified by direct sequencing by Qiagen Genomic Services.

C. Kanamycin Backbone Cloning

The transgene cassettes from both (pAAV.CB7.CI.FI6.RBG (p3193) and pAAV.CB7.CI.CR8033.RBG (p3523) will be cloned into an AAV2 ITR-flanked construct. The plasmid backbone in this construct is derived from, pZac2.1, a pKSS-based plasmid and contains the kanamycin resistance gene. The final vector genome plasmids will be pAAV.CB7.CI.FI6.RGB.KanR and pAAV.CB7.CI.CR8033.RBG.Kan. All component parts of the final vector genome plasmids will be verified by sequencing and the sequences confirmed as part of the GMP manufacturing process.

D. Description of the Sequence Elements

1. Inverted terminal repeats (ITR): AAV ITRs (GenBank #NC001401) are sequences that are identical on both ends, but in opposite orientation. The AAV2 ITR sequences function as both the origin of vector DNA replication and the packaging signal of the vector genome, when AAV and adenovirus helper functions are provided in trans. As such, the ITR sequences represent the only cis sequences required for vector genome replication and packaging.
2. Cytomegalovirus (CMV) immediate early enhancer (260 bp, C4; GenBank #K03104.1). This element is present in both vector genome plasmids.
3. Chicken beta-actin promoter (281 bp; CB; GenBank #X00182.1) promoter and is used to drive high-level antibody expression. This element is present in both vector genome plasmids.
4. Chicken beta-actin intron: The 875 bp intron from the chicken beta actin gene (GenBank #X00182.1) is present in the vector expression cassette. The intron is transcribed, but removed from the mature mRNA by splicing, bringing together the sequences on either side of it. The presence of an intron in an expression cassette has been shown to facilitate the transport of mRNA from the nucleus to the cytoplasm, thus enhancing the accumulation of the steady level of mRNA for translation. This is a common feature in gene vectors intended for increased level of gene expression. This element is present in both vector genome plasmids.
5. C-myc 5' UTR: Nucleotides 381-428 of Homo sapiens v-myc avian myelocytomatosis viral oncogene homolog (MYC) mRNA GenBank Accession #NM002467). This element is present in both vector genome plasmids.
6. Leader (signal) peptide cDNA: A codon optimized cDNA sequence (GenBank Accession #AAB8686.1) preceding and in frame with the FI6 heavy chain was synthesized.
7. FI6v3 heavy variable chain cDNA: A codon optimized human cDNA sequence (GenBank Accession #AEL31303.1) was synthesized.
8. Leader (signal) peptide cDNA: A codon optimized cDNA sequence (ILco2 described in [Zhang, L., Q. Leng, and A. J. Mixson, J Gene Med, 2005. 7(3): p. 354-6]) preceding and in frame with the CR8033 heavy chain was synthesized.
9. CR8033 heavy variable chain cDNA: A codon optimized human cDNA sequence (GenBank Accession #AFP87542.1) was synthesized.
10. Constant heavy 1 (CH1) chain: A codon optimized cDNA (GenBank Accession #BAF64540.1) was synthesized. This element is present in both vector genome plasmids.
11. CR8033 Fc chain (CH2-3): A codon optimized cDNA (GenBank Accession #226787 with the exception of C-terminal lysine which was replaced with arginine) was synthesized.
12. F16 Fc chain (CH2-3): A codon optimized cDNA (GenBank Accession #2J6E_A with the exception of C-terminal lysine which was replaced with arginine and position 57, where aspartic acid was replaced glutamic acid) was synthesized by GeneArt.
13. Leader (signal) peptide cDNA: A codon optimized cDNA sequence which precedes the universal light chain (ILhy1 described in [Zhang et al, cited above) was synthesized.
14. Universal light chain cDNA: A codon optimized human cDNA sequence (GeBank Accession #ACJ71709.1) was synthesized. This element is present in both vector genome plasmids.
15. Constant light chain cDNA: A codon human sequence (GenBank Accession #AGH70219.1) was synthesized. This element is present in both vector genome plasmids.
16. Furin recognition site: An Arginine-Lysine-Arginine-Arginine and codon optimized cDNA was synthesized. This element is present in both vector genome plasmids.
17. F2A linker: A 24 amino acid peptide derived from FMDV (GenBank #CAA2436.1) and codon optimized cDNA was synthesized. This element is present in both vector genome plasmids.
18. Polyadenylation Signal: The 127 bp rabbit beta-globin polyadenylation signal (GenBank #V00882.1) provides cis sequences for efficient polyadenylation of the antibody mRNA. This element functions as a signal for transcriptional termination, a specific cleavage event at the 3' end of the nascent transcript and addition of a long polyadenyl tail. This element is present in both vector genome plasmids.

E. AAV2/9 Helper Plasmid pAAV2.9.KanR

This AAV2/9 helper plasmid p5E18.AAV2/9n (p0061; 7330bp) is an AAV helper plasmid that encodes the 4 wild-type AAV2 rep proteins and the 3 wild-type AAV VP capsid proteins from AAV serotype 9 [J Virol. 2004 Ju; 78(12): 6381-8].

To create the chimeric packaging construct, the AAV2 cap gene from plasmid p5E18, containing the wild type AAV2 rep and cap genes, was removed and replaced with a PCR fragment of the AAV2/9 cap gene amplified from liver DNA to give plasmid p5E18VD2/AAV2/9. Note that the AAV p5 promoter which normally drives rep expression is moved in this construct from the 5' end of rep to the 3' end of cap. This arrangement serves to introduce a spacer between the promoter and the rep gene (i.e. the plasmid backbone), downregulate expression of rep and increase the ability to support vector production. The plasmid backbone in p5E18 is from pBluescript KS. All component parts of the plasmid have been verified by direct sequencing. The ampicillin resistance gene will be replaced by the kanamycin resistance gene to give pAAV2/9n.KanR.

F. pAdDeltaF6(Kan) Adenovirus Helper Plasmid

Plasmid pAdDelta (A)F6(Kan) is 15,774 bp in size. The plasmid contains the regions of adenovirus genome that are important for AAV replication, namely E2A, E4, and VA RNA (the adenovirus E1 functions are provided by the 293 cells), but does not contain other adenovirus replication or structural genes. The plasmid does not contain the cis elements critical for replication such as the adenoviral inverted terminal repeats and therefore, no infectious adenovirus is expected to be generated. It was derived from an E1, E3 deleted molecular clone of Ad5 (pBHG10, a pBR322 based plasmid). Deletions were introduced in the Ad5 DNA to remove expression of unnecessary adenovirus genes and reduce the amount of adenovirus DNA from 32 Kb to 12 kb). Finally the ampicillin resistance gene was replaced by the kanamycin resistance gene to give pAdΔF6(Kan). The E2, E4 and VAI adenoviral genes which remain in this plasmid, along with E1, which is present in HEK293 cells, are necessary for AAV vector production.

EXAMPLE 2

Manufacturing Process

Cells are cultivated in Corning 10 layer Cell Stacks (CS-10) and HS-36 and all open manipulations are performed in class II biosafety cabinets in an ISO Class 5 environment. The purification process is performed in a closed system where possible however, column chromatography manipulations are not viewed as a completely closed system. To minimize this risk, single-use disposable flow paths are utilized as part of the GE ReadyMate column chromatography production skid platform. After column chromatography purification, the product is diafiltered with final formulation buffer (1×PBS (200 mM NaCl) 0.001% Pluronic F68, 5% glycerol) and sterile filtered to yield the BDS, which is frozen at ≤−60° C. After BDS testing, the BDS is thawed, pooled, and diluted as necessary with sterile final formulation buffer and filled at SAFC in their Fill Suite. In the case where the two vector components of GTP101 are manufactured separately, the components are mixed at a 1:1 ratio prior to fill.

Figure 2:
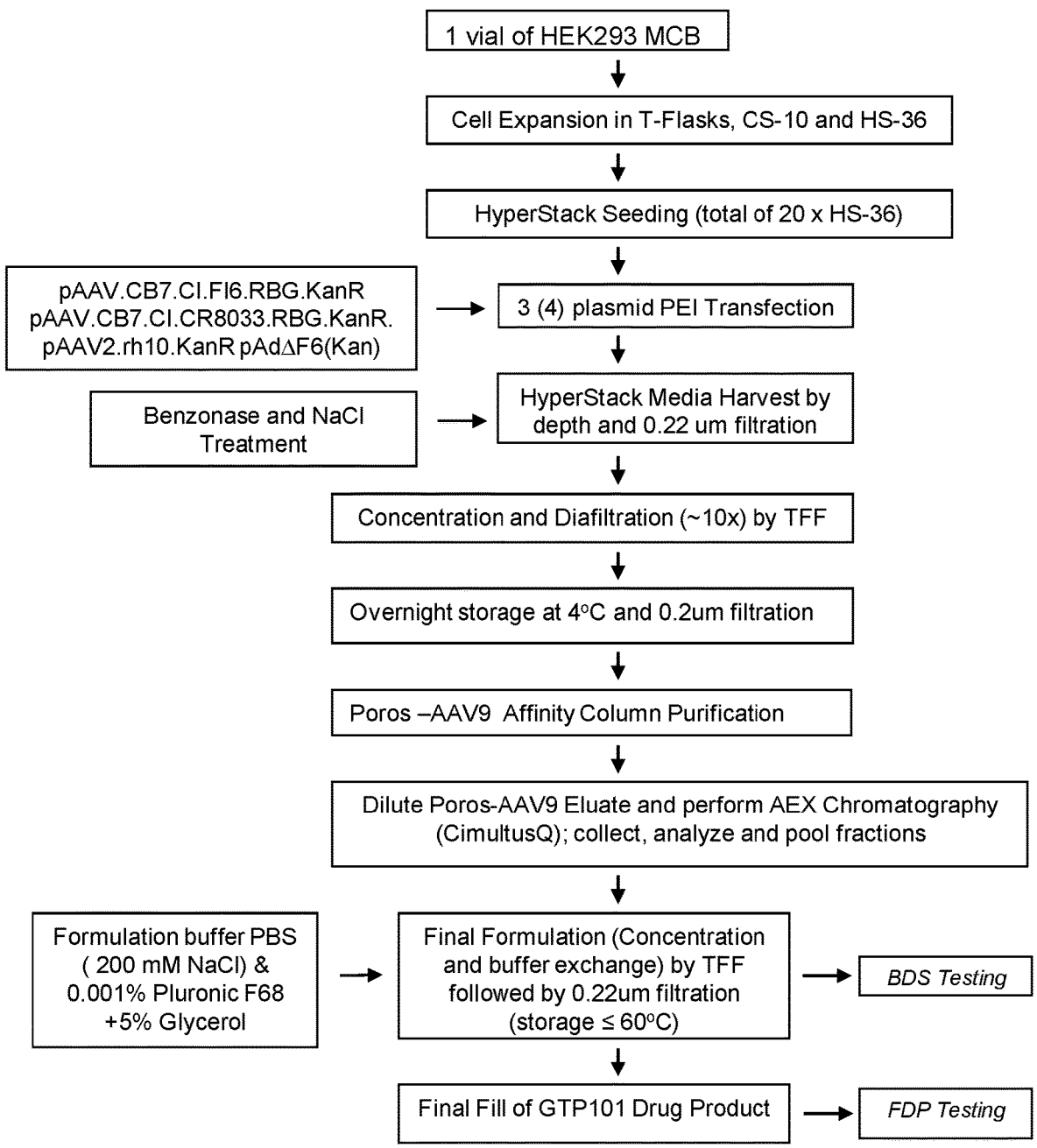
FIG. 2 is a flow diagram providing an overview of the manufacturing process.
Figure 6A:
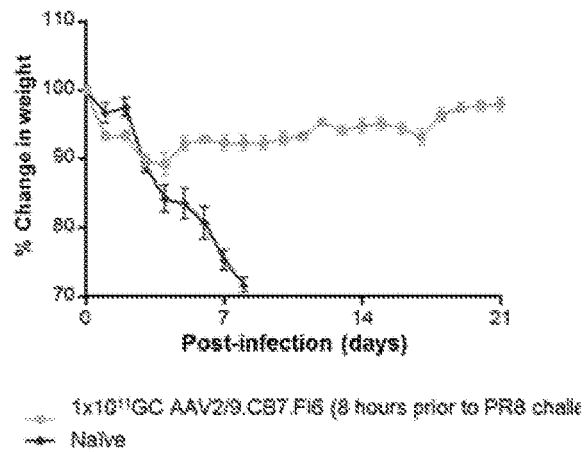
FIG. 6A and FIG. 6B show rapid onset of protection against influenza challenge. $1\times10^{11}$ GC of AAV2/9.CB7.FI6 was delivered IN in BALB/c mice and 8 hours later mice were challenged with $5LD_{50}$ of PR8.
Figure 6B:
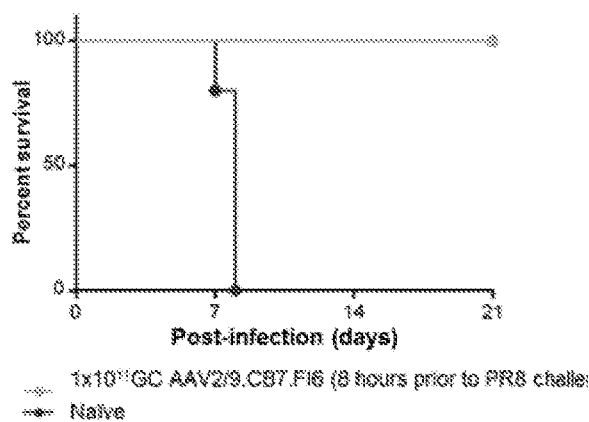

An overview of the manufacturing process is given in FIG. 2.

A. Cell Seeding: HEK 293 cells express the E1a and E1b gene products required for high-titer rAAV production. HEK293 cells are adherent and highly transfectable yielding high-titers of rAAV upon DNA plasmid transfection. Cells will be expanded to $5 \times 10^9$-$5 \times 10^{10}$ cells using Corning T-flasks and CS-10, which will allow sufficient cell mass to be generated for seeding twenty HS-36 for vector production per BDS lot. Cells will be cultivated in medium composed of Dulbecco's Modified Eagle Medium (DMEM), supplemented with 10% gamma irradiated, New Zealand-sourced, Fetal Bovine Serum (FBS). The cells are anchorage dependent and cell disassociation will be accomplished using TrypLE Select, a non-animal cell dissociation reagent. Cell seeding is accomplished using sterile, single-use disposable bioprocess bags and tubing sets. The cells will be maintained at 37° C. (±1° C.), in 5% (±0.5%) $CO_2$ atmosphere.

B. Transient Transfection: Following 3 days of growth (DMEM media+10% FBS), HS-36 cell culture media will be replaced with fresh, serum free DMEM media and transfected with the three production plasmids using an optimized PEI-based transfection method. All plasmids used in the production process will be produced by Aldevron Inc. under its GMP-Source™ quality system and infrastructure utilizing the most salient features of cGMP manufacturing; traceability, document control, and materials segregation.

Sufficient DNA plasmid transfection complex will be prepared in the BSC to transfect twenty HS-36 (per BDS lot). Initially a DNA/PEI mixture will be prepared containing 3.0 mg of pAAV.CB7.CI.FI6.RBG.KanR or pAAV.CB7.CI.CR8033.RBG.KanR vector genome plasmid, 60 mg of pAdDeltaF6(Kan), 30 mg of pAAV2.rh10.KanR AAV helper plasmid and GMP grade PEI (PEIPro, PolyPlus Transfection SA). In the alternate case where mixed vector genome plasmid transfections are employed, 1.5 mg of each of the two cis plasmids will be used. After mixing well, the solution is allowed to sit at room temperature for 25 min. and then added to serum-free media to quench the reaction and then added to the HS-36's. The transfection mixture is equalized between all 36 layers of the HS-36 and the cells are incubated at 37° C. (±2° C.) in a 5% (±0.5%) $CO_2$ atmosphere for 5 days.

C. Cell Media Harvesting: Transfected cells and media will be harvested from each HS-36 using disposable bioprocess bags by aseptically draining the medium out of the units. Following the harvest of media, the ~80 liter volume will supplemented with $MgCl_2$ to a final concentration of 2 mM (co-factor for Benzonase) and Benzonase nuclease (Cat #: 1.016797.0001, Merck Group) added to a final concentration of 25 units/ml. The product (in a disposable bioprocess bag) will incubated at 37° C. for 2 hr in an incubator to provide sufficient time for enzymatic digestion of residual cellular and plasmid DNA present in the harvest as a result of the transfection procedure. This step is performed to minimize the amount of residual DNA in the final vector FDP. After the incubation period, NaCl will be added to a final concentration of 500 mM to aid in the recovery of the product during filtration and downstream tangential flow filtration (see below steps 4 and 5).

D. Clarification: Cells and cellular debris will be removed from the product using a depth filter capsule (1.2 μm/0.22 um) connected in series as a sterile, closed tubing and bag set that is driven by a peristaltic pump. Clarification assures that downstream filters and chromatography columns will be protected from fouling and bioburden reduction filtration ensures that at the end of the filter train, any bioburden potentially introduced during the upstream production process will be removed before downstream purification. The media will be passed through a Sartorius Sartoguard PES capsule filter (1.2/0.22 μm) (Sartorius Stedim Biotech Inc.).

E. Large-scale Tangential Flow Filtration: Volume reduction (10-fold) of the clarified product will be achieved using Tangential Flow Filtration (TFF) using a custom sterile, closed bioprocessing tubing, bag and membrane set produced by Spectrum Labs. The principle of TFF is to flow a solution under pressure parallel to a membrane of suitable porosity (100 kDa). The pressure differential drives molecules of smaller size through the membrane and effectively into the waste stream while retaining molecules larger than the membrane pores. By recirculating the solution, the parallel flow sweeps the membrane surface preventing membrane pore fouling. By choosing an appropriate membrane pore size and surface area, a liquid sample may be rapidly reduced in volume while retaining and concentrating the desired molecule. Diafiltration in TFF applications involves addition of a fresh buffer to the recirculating sample at the same rate that liquid is passing through the membrane and to the waste stream. With increasing volumes of diafiltration, increasing amounts of the small molecules are removed from the recirculating sample. This results in a modest purification of the clarified product, but also achieves buffer exchange compatible with the subsequent affinity column chromatography step. Accordingly, a 100 kDa, PES membrane (Spectrum Labs) is used for concentration that is then diafiltrated with 4 volumes of a buffer composed of: 20 mM Tris pH 7.5 and 400 mM NaCl. The diafiltered product will be stored overnight at 4° C. and then further clarified with a 1.2 µm/0.22 um depth filter capsule to remove any precipitated material.

F. Affinity Chromatography: The diafiltered product will be applied to a Capture Select™ Poros- AAV2/9 affinity resin (Life Technologies) that efficiently captures the AAV2/9 serotype. Under these ionic conditions, a significant percentage of residual cellular DNA and proteins flow through the column, while AAV particles are efficiently captured. Following application, the column is washed to remove additional feed impurities followed by a low pH step elution (400 mM NaCl, 20 mM Sodium Citrate; pH 2.5) that is immediately neutralized by collection into a $1/10^{th}$ volume of a neutralization buffer (Bis Tris Propane, 200 mM, pH 10.2).

G. Anion Exchange Chromatography: To achieve further reduction of in-process impurities including empty AAV particles, the Poros-AAV2/9 elution pool is diluted 50-fold (20 mM Bis Tris Propane, 0.001% Pluronic F68; pH 10.2) to reduce ionic strength to enable binding to a ClMultus Q monolith matrix (BIA Separations). Following a low-salt wash, vector product is eluted using a 60 CV NaCl linear salt gradient 10-180 mM NaCl). This shallow salt gradient effectively separates capsid particles without a vector genome (empty particles) from particles containing vector genome (full particles) and results in a preparation largely devoid of empty capsids. Fractions will be collected into tubes containing $1/100^{th}$ volume of 0.1% pluronic F68 and $1/27^{th}$ volume of Bis Tris pH 6.3 to minimize non-specific binding to tubes and the length of exposure to high pH respectively. Peak purity and yield elution fractions are identified by qPCR, pooled and stored at 4° C. until final formulation using TFF. AEX pool qPCR titer data will be used to estimate the target final volume to achieve a titer of $2 \times 10^{13}$ GC/ml for final formulation (step immediately below).

H. Final Formulation and Sterile Filtration to yield the BDS: TFF will be used to achieve final formulation on the pooled AEX fractions with a 100 kDa membrane (Spectrum Labs, Inc.). This will be achieved by diafiltration with 4 volumes of formulation buffer (1×PBS (200 mM NaCl) 0.001% Pluronic F68, 5% glycerol) and concentrated to the calculated volume to achieve the target concentration. Following diafitration, the product will be terminally filtered through a 0.22 um filter (Millipore, Billerica, Mass.) to yield the BDS. Samples will be removed for BDS testing (described in the section below). The filtered Purified Bulk will be stored in sterile polypropylene tubes and frozen at ≤−60° C. in a quarantine location until release for Final Fill.

I. Final Fill: The frozen BDS will be thawed (and pooled as required) and filled into West Pharmaceutical's "Ready-to-Use" (pre-sterilized) 2 ml glass vials and 13 mm stoppers and seals at a fill volume ≥0.6 ml to ≤2.0 ml per vial. Fill operations will occur according to standardized Fill operations supported by technician and process qualification at SAFC. At the completion of Final Fill, all operators working in the Fill suite will be monitored with RODAC plates (to detect viable particulates) on their sterile gloves as they leave the BSC. The BSC surface will also be monitored for viable organisms at the conclusion of Fill. SAFC QC will inspect the vials for appearance, particulates, volume and integrity. Individually labeled vials will be labeled to include protocol number, product name, lot number, allocation number and stored in labeled boxes. Labeled vials are transferred to quarantine ≤−60° C. until release.

J. ddPCR GC Titer: The accuracy and reliability of the quantitative PCR (qPCR) genome copy (GC) titration is paramount for AAV quality control and vector dosing. Genome titers will be measured by a new qPCR technique based on droplet digital PCR [Lock, M., et al., Absolute determination of single-stranded and self-complementary adeno-associated viral vector genome titers by droplet digital PCR. Hum Gene Ther Methods, 2014. 25(2): p. 115-25] which gives unparalleled accuracy and reproducibility. DNA detection will be accomplished using sequence specific primers and fluorescently labelled probes targeting the FI6 and CR8033 coding regions to allow for quantification of component genomes in the FDP. In addition primers and probes targeting the RBG polyA region will be used to determine the total genome content of the FDP. A number of standards, validation samples and controls (for background and DNA contamination) have been introduced into the assay. The assay will be qualified by establishing and defining assay parameters including sensitivity, limit of detection, range of qualification and intra and inter assay precision. An internal AAV2/9 reference lot produced using the newly developed production process will be established and used to perform the qualification studies. Note that our previous experience suggests that the titer obtained by droplet digital PCR is generally 2-fold higher than that achieved by our standard pPCR technique. Once this new method of tittering is qualified, all previous test articles used in pilot studies described in sections 6 and 8 will be re-assayed and the dosing will be adjusted. This may impact on the actual dosing used in the nonclinical and clinical studies although the expectation is that the difference will be no greater than 2-fold.

L. Infectious Titer: The infectious unit (IU) assay is used to determine the productive uptake and replication of GTP101 vector in RC32 cells (rep2 expressing HeLa cells). A 96-well end-point format has been employed similar to that previously published. Briefly, RC32 cells are co-infected by serial dilutions of GTP101 BDS and a uniform dilution of Ad5 with 12 replicates at each dilution of rAAV. Seventy-two hours after infection the cells are lysed, and qPCR performed to detect rAAV vector amplification over input. An end-point dilution $TCID_{50}$ calculation (Spearman-Karber) is performed to determine a replicative titer expressed as IU/ml. Since "infectivity" values are dependent on particles coming into contact with cells, receptor binding, internalization, transport to the nucleus and genome replication, they are influenced by assay geometry and the presence of appropriate receptors and post-binding pathways in the cell line used. Receptors and post-binding pathways are not usually maintained in immortalized cell lines and thus infectivity assay titers are not an absolute measure of the number of "infectious" particles present. However, the ratio of encapsidated GC to "infectious units" (described as GC/IU ratio) can be used as a measure of product. consistency from lot to lot.

M. Host Cell (human) DNA

A qPCR assay will be used to detect residual human 293 DNA in the BDS. After spiking with a "non-relevant DNA", total DNA (non-relevant, vector and residual genomic) is extracted from ~1 ml of product. The Host Cell DNA is quantified using qPCR targeting the 18S rDNA gene. The quantities of DNA detected are normalized based on the recovery of the spiked non-relevant DNA.

N. Host Cell (Human) Protein

An ELISA will be performed on a BDS sample to measure levels of contaminating host HEK293 cell proteins. The Cygnus Technologies HEK 293 Host Cell Proteins 2nd Generation ELISA kit will be used. Samples and pre-diluted HEK 293 HCP standards are added to microtiter wells pre-coated with an affinity purified anti-HEK 293 HCP capture antibody, along with a peroxidase conjugated polyclonal anti-HEK 293 HCP detection antibody. Following incubation, the wells are washed to remove unbound reactants, and TMB, a peroxidase substrate, is added. After development, the reaction will be stopped using a sulfuric acid solution. The absorbance of the resulting colored product will be measured using a microplate reader, and the amount of HEK 293 HCP in each sample calculated from the standard curve.

O. Replication-Competent AAV (rcAAV)

As part of the BDS test plan, a sample of GTP101 FDP will be analyzed for the presence of replication competent AAV2/9 (rcAAV) that can potentially arise during the production process. A three passage assay has been developed consisting of cell-based amplification and passage followed by detection of rcAAV DNA by real-time qPCR (cap 9 target). The cell-based component consists of inoculating monolayers of HEK293 cells (P1) with dilutions of the test sample and wild-type human adenovirus type 5 (Ad5). $10^{10}$ DRP of the vector product will be the maximal amount of the product tested. Due to the presence of adenovirus, replication competent AAV will amplify in the cell culture. After two days, a cell lysate is generated and Ad5 heat inactivated. The clarified lysate is then passed onto a second round of cells (P2) to maximize sensitivity (again the presence of Ad5). After 2 days, a cell lysate is generated and Ad5 heat inactivated. The clarified lysate is then passed onto a third round of cells (P3) to maximize sensitivity (again the presence of Ad5). After 2 days, cells are lysed to release DNA which is then subjected to qPCR to detect AAV2/9 cap sequences. Amplification of AAV2/9 cap sequences in an Ad5 dependent manner indicates the presence of rcAAV. The use of a AAV2/9 surrogate positive control containing AAV2 rep and AAV2/9cap genes enables the Limit of Detection (LOD) of the assay to be determined (0.1, 1 10 and 100 IU) and using a serial dilution of GTP101 vector ($1\times10^{10}$, $1\times10^{9}$, $1\times10^{8}$, $1\times10^{7}$ DRP) the approximate level of rcAAV present in the test sample can be quantitated.

P. In Vitro BioPotency

To relate the qPCR GC titer to gene expression, an in vitro bioassay will be performed by transducing HEK293 cells with a known multiplicity of GCs per cell and measuring secreted FI6 and CR8033 expression 72 hours post transduction using anti-idiotype ELISA's specific for the two mAbs. Comparison to highly active pre-clinical and tox vector preparations will enable interpretation of product activity.

Q. Total Protein, Capsid protein and Protein Purity Determination

The vector samples are first quantified for total protein against a Bovine Serum Albumin (BSA) protein standard curve using a bicinchoninic acid assay. The determination is made by mixing equal parts of sample with a Micro-BCA reagent provided in the kit. The same procedure is applied to dilutions of a BSA Standard. The mixtures are incubated at 60° C. and absorbance measured at 562 nm. A standard curve is generated from the standard absorbance of the known concentrations using a 4-Parameter fit. Unknown samples are quantified according to the 4-Parameter regression.

To provide a semi-quantitative determination of AAV purity, the samples will then be normalized for genome titer and $5\times10^{9}$ GC separated on an SDS-polyacrylamide (SDS-PAGE) gel. The gel is then stained with SYPRO Ruby dye. Any impurity bands are quantified by comparison to co-electrophoresed BSA standards of 25, 50, and 100 ng of protein per lane. These quantities represent 1%, 2% and 4% of the total AAV protein sample. Stained bands that appear in addition to the three AAV specific proteins VP1, VP2 and VP3 are considered protein impurities. All impurity bands are compared to the reference proteins and the impurity mass percent as well as approximate molecular weight are reported. The SDS—PAGE gels will also be used to quantify the VP1, VP2 and VP3 proteins and determine their ratio.

R. BSA Protein

This assay is performed for Release Testing using the Bovine Albumin ELISA kit obtained from Bethyl Laboratories. This kit is a sandwich ELISA. BSA present in the test sample is captured by anti-Bovine Albumin antibody that has been pre-adsorbed on the surface of microtiter wells. After sample binding, unbound proteins and molecules are washed off, and a biotinylated detection antibody is added to the wells to bind the captured albumin A strepavidin-conjugated horseradish peroxidase (SA-HRP) is then added to catalyze a colorimetric reaction with the chromogenic substrate TMB (3,3',5,5'-tetramethylbenzidine). The colorimetric reaction produces a blue product, which turns yellow when the reaction is terminated by addition of dilute sulfuric acid. The absorbance of the yellow product at 450 nm is proportional to the amount of albumin analyte present in the sample and a four-parameter standard curve can be generated. The albumin concentrations in the test samples can then be quantified by interpolating their absorbance from the standard curve generated in parallel with the samples. After factoring sample dilutions, the albumin concentrations in the original sample can finally be calculated.

S. Benzonase Endonuclease

Benzonase is used in the production process to degrade nucleic acids to facilitate vector purification and as such represents a process impurity. For Release Testing a commercial ELISA is used to measure the concentration of residual Benzonase. Since the amount of benzonase is likely to be in trace amounts if at all, it is necessary to perform an ELISA with a range of standards that includes concentrations <1 ng/ml.

T. Ratio of GC to 1U

The GC/IU ratio is a measure of product consistency. The qPCR titer (GC/ml) is divided by the "infectious unit assay (IU/ml) to give the calculated GC/IU ratio.

U. Osmolality, pH, and Appearance Testing

These assays are performed for Release Testing by BREL using test protocols for Osmolality by freezing point depression. Appearance of the product is determined by visual inspection for transparency, color and the absence/presence of foreign particles. The product is inspected against white and black backgrounds. The pH of the FDP is determined using a calibrated pH micro-electrode with temperature compensation.

EXAMPLE 3

Assessment of Individual Components of GTP101

Figure 10:
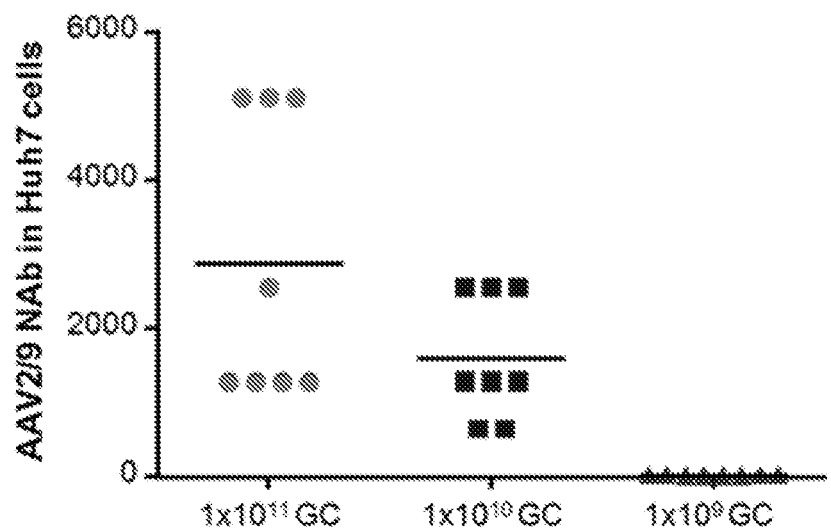
FIG. 10 shows levels of serum-circulating AAV2/9-specific NAb. Mice were given intranasal (i.n.) AAV2/9 vector at doses ranging from $1\times10^9$ to $1\times10^{11}$ GC/mouse and AAV2/9 neutralizing antibody in serum assayed at day 28 following AAV2/9 delivery.
Figure 11A:
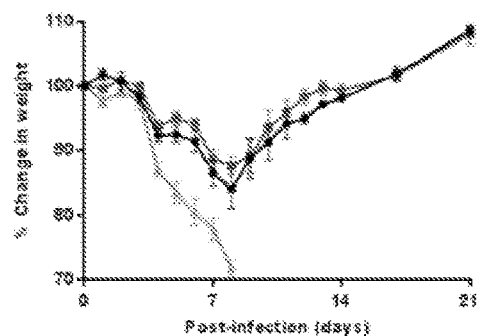
FIGS. 11A-11G shows vector-mediated prophylaxis against challenge with influenza A (PR8). 6 week old female BALB/c mice (n=5/group) were given i.n. a mixture of $1\times10^9$ GC of AAV2/9.CB7.CR8033 and $1\times10^9$ GC of AAV2/9.CB7.FI6 in a total volume of 50 µl PBS. The vector was formulated in three different solutions: PBS-pH 6.8, PBS-pH 7.2 or PBS-pH 7.4. Mice were challenged with $5LD_{50}$ of PR8 7 days after vector administration. The weights of the animals were recorded daily and mice were euthanized when they appeared in distress or when they lost <30% of their pre-challenge body weight. Mice were given i.n. $1\times10^9$ GC AAV2/9.CB7.CR8033 and $1\times10^9$ GC of AAV2/9.CB7.FI6 in PBS-pH 6.8 (FIG. 11A), PBS-pH 7.2 (FIG. 11D or PBS-pH 7.4 (FIG. 11G and challenged with PR8 seven days later.
Figure 11B:
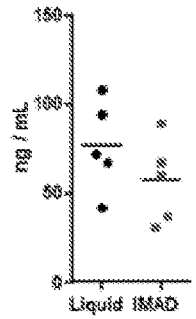
Figure 11C:
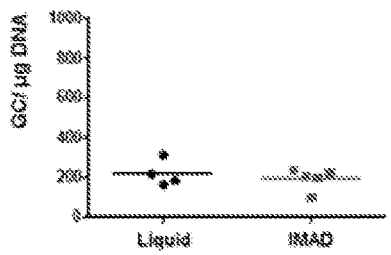
Figure 11D:
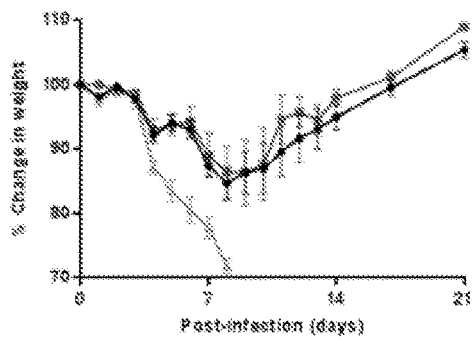
Figure 11E:
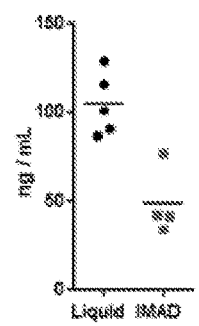
Figure 11F:
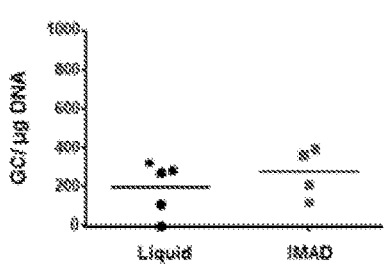
Figure 11G:
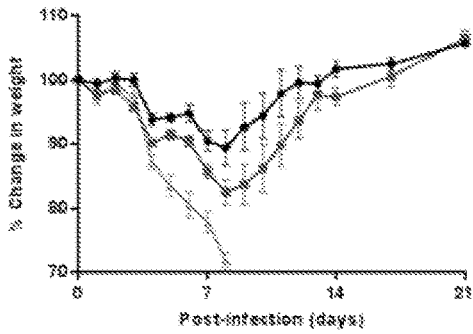
Figure 11H:
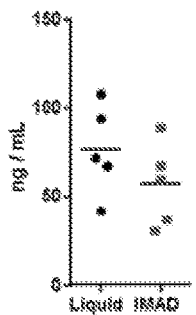
Figure 11I:
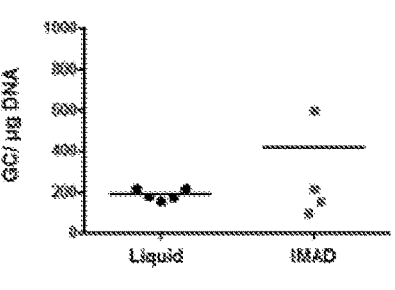

A. Determination of Minimum Effective Dose (MED) of AAV2/9.CB7.FI6 Required to Protect Against Lethal Challenge with Influenza A AAV2/9.CB7.FI6 was delivered intranasally (IN) in 6 week old female BALB/c mice at doses ranging from $1 \times 10^7$ to $1 \times 10^{10}$ GC/mouse and challenged IN with $5LD_{50}$ of mouse adapted H1N1 (PR8) 14 days later. As shown in FIGS. 3A-3B, the MED (defined as the dose required for 100% of challenged mice to survive challenge with $5LD_{50}$ of PR8) for AAV2/9.CB7.FI6 in mice was found to be $1\times10^9$ GC/mouse with partial protection conferred with a half log reduced dose ($3\times10^8$ GC/mouse).

At day 14, 3 mice per treatment group that were not challenged were sacrificed to assess the level of FI6 expression at the airway surfaces, namely the bronchoalveolar lavage fluid (BALF) and nasal lavage fluid (NLF). As shown in FIGS. 4A and 4B, the amount of FI6 Ab that was measured at the surface of the lung (BALF) or nose (NLF) correlated with AAV2/9 vector dose. The amount of antibody secreted in the NLF is difficult to accurately determine due to the small volume of the mouse airway surface liquid (ASL) layer, that is estimated to be 1 μl.

The viral load (plaque forming units; PFU) was assessed six days after the challenge with PR8 (FIG. 5) and found that for mice treated with $1\times10^{10}$ GC of AAV2/9.CB7.FI6 their lungs were clear of PR8 and significant reduction in viral load was observed in mice treated with $3\times10^9$ GC and also $1\times10^9$ GC of AAV2/9.CB7.FI6. Both these doses were found to be protective against the influenza challenge.

B. Onset of AAV2/9-Prophylaxis Against Inhaled Influenza

The rapid onset of efficacy is beneficial when dealing with an influenza outbreak that requires fast response times. As such, the interval between AAV2/9.CB7.FI6 IN delivery and challenge with $5LD_{50}$ PR8 was varied to determine how quickly protection could be achieved. The shortest interval between vector treatment and challenge was 8 hours. Mice that were pre-administered the vaccine and challenged 8 hours later lost some weight but recovered and survived the challenge (FIGS. 6A and 6B).

C. Determination of the MED of AAV2/9.CB7.CR8033 required to protect against lethal challenge with influenza In concurrent studies, the potential for AAV2/9 expressing the anti-influenza Ab CR8033 to protect against influenza B challenge was assessed. Six week old female BALB/c mice were given AAV2/9.CB7.CR8033 at doses ranging from $1\times10^7$ to $1\times10^{10}$ GC/mouse and challenged IN with $5LD_{50}$ of mouse adapted B/Lee/40. 14 days later we found that likewise the MED was $1\times10^9$ GC/mouse (FIGS. 7A and 7B). No mice survived the challenge with B/Lee/40 virus when they were given IN the half log reduced dose of $3\times10^8$ GC/mouse.

D. AAV2/9 Vector Dissemination following IN Delivery in Mice.

An important safety aspect of the AAV-mediated prophylaxis strategy described herein is targeting vector-mediated transduction to the terminally differentiated cells of respiratory surfaces. Potential body wide dissemination of the AAV2/9 vector in mice that survived the PR8 challenge was determined. Mice were given AAV2/9.CB7.FI6 at varying doses and following the challenge mice were necropsied and tissues (lung, liver, spleen, ovaries, brain, heart) harvested to assess vector biodistribution. For vector doses $1\times10^9$-$1\times10^{10}$ GC/mouse, all mice (5 per group) survived the challenge. At all doses the highest quantities of vector genomes were found in the lung (e.g., at the highest dose of vector the ratio of lung/liver AAV2/9 genomes was 1783). For the higher dose of $1\times10^{10}$ GC/mouse, no GG/diploid genome was observed in the spleen, brain and heart. Very low levels of AAV2/9 vector were detected in the liver and ovary and as expected the majority of AAV2/9 genome copies were observed in the liver. In mice treated with $3\times10^9$ GC, no AAV2/9 was detected in the liver, ovaries and spleen, and low levels of capsid were observed in the brain and heart. As expected, there was a decline of vector genomes in the lung. In the mice treated with $1\times10^9$ GC, vector genome, albeit much reduced, were observed in the lung only. For the survivors of the $3\times10^8$ GC/mouse treatment group, the level of AAV2/9 genome copies was undetectable (below limit of detection, LD).

| | Lung | Liver | Spleen | Ovaries | Brain | Heart |
|---|---|---|---|---|---|---|
| $1\times10^{10}$ GC | 0.1783 | 0.0001 | <LD | 0.0005 | <LD | <LD |
| $3\times10^9$ GC | 0.0178 | <LD | <LD | <LD | 0.0043 | 0.0003 |
| $1\times10^9$ GC | 0.0011 | <LD | <LD | <LD | <LD | <LD |
| $3\times10^8$ GC | <LD | <LD | <LD | <LD | <LD | <LD |

Presence of Vector Genomes/Diploid Genome

EXAMPLE 4

Mixing Two AAVs on the Protective Efficacy Against Influenza a and Influenza B The impact on prophylaxis against influenza A and influenza B by mixing two different AAV preparations was assessed. Mice were dosed IN with a mixture of $1\times10^9$ GC with AAV2/9.CB7.FI6 and $1\times10^9$ GC AAV2/9.CB7.CR8033 and challenged with $5LD_{50}$ of either PR8 or B/Lee/40 virus. Should there be interference or receptor binding competition, then protective efficacy would be significantly lower when compared to protection conferred by the administration of the single protective AAV2/9 vector.

In the first instance the mixture of $1\times10^9$ GC AAV2/9.CB7.FI6 and $1\times10^9$ GC AAV2/9.CB7.CR8033 was assessed for protection against challenge with PR8 and compared to the protection conferred against PR8 when $1\times10^9$ GC AAV2/9.CB7.FI6 was delivered alone. As shown in FIG. 8, no interference was observed.

The mixture of $1\times10^9$ GC with AAV2/9.CB7.FI6 and $1\times10^9$ GC AAV2/9.CB7.CR8033 was then assessed for protection against challenge with B/Lee/40 (influenza B) and compared to the protection conferred against influenza B when $1\times10^9$ GC AAV2/9.CB7.CR8033 was delivered alone. As demonstrated in FIG. 9, there was no interference.

EXAMPLE 5

Effective Vector Re-Administration and Protection Against Challenge with Influenza A An important feature of the AAV2/9 vector delivery system is that it can be administered more than once. To simulate a setting of preexisting immunity against the AAV2/9 capsid, we delivered IN AAV2/9 vector expressing an irrelevant to influenza transgene product at doses ranging from $1\times10^9$ to $1\times10^{11}$ GC/mouse. Twenty-eight days later, the level of serum-circulating AAV2/9-specific neutralizing antibody (NAb) was assessed (FIG. 10). As expected, the level of AAV2/9 NAb in serum was directly proportional to the dose of AAV2/9 delivered IN.

AAV2/9 pre-immunized mice were then given $1\times10^{11}$ GC of AAV2/9.CB7.FI6. If the NAb against the AAV2/9 capsid prevented effective AAV2/9 re-administration, then the pre-immunized mice would succumb to the PR8 challenge. Despite the high levels of serum-circulating AAV2/9 NAb that reached 1:5,120 serum dilution, AAV2/9.CB7.FI6 was effectively readministered and resulted in full protection against a $5LD_{50}$ challenge with PR8.

EXAMPLE 6

Impact of an Interim Infection on the Efficiency of AAV2/9-Mediated F16 Prophylaxis Against PR8

Following IN administration of AAV2/9.CB7.FI6, a possibility exists that the patient may experience an interim infection with an airborne infection other than influenza, such as rhinovirus or RSV. As a result of the infection, a subset of respiratory cells that line the surface of the nasal and lung airways will be damaged and lost. The impact of positively-transduced cells being turned over as a result of injury following viral infection, on the efficacy of AAV2/9.CB7.FI6-mediated prophylaxis against influenza was assessed. Briefly, $1\times10^{10}$ GC of AAV2/9.CB7.FI6 was delivered IN in 6 week old female BALB/c mice. To induce damage to the epithelium, two weeks later, one group was challenged with $1\times10^6$pfu of RSV and the other group was treated IN with PBS. Four weeks later all mice were challenged IN with $5LD_{50}$ of PR8 and weight loss and survival monitored. There was no impact on the efficacy of AAV2/9-mediated prophylaxis in the event of an interim infection.

EXAMPLE 7

Pilot Toxicity and Expression Studies

A transitional non-GLP study will be performed in immune competent CD-1 mice to evaluate safety, kinetics, and immune responses. Outbred CD-1 mice are expected to respond to the GTP101 (AAV2/9.CB7.FI6 and AAV2/9.CB7.CR8033 vectors; GTP101 investigational product (IP)) in a manner similar to humans due to their genetic heterogeneity. This transitional study is necessary because the majority of the prior work was performed using various inbred strains. Toxicities caused directly by the transgene product can not be assessed in CD-1 mice, and instead will be assessed in immune compromised, inbred mice as described elsewhere in this document.

To model in mice the deposition of IP via the IMAD in the human nasal airways, we will lower the volume of liquid in which the vector is delivered to target the mouse nasal airway. Previously, we conducted studies in which reducing the volume to 20 μl restricts expression to the nasal airway [Limberis, M. P., et al., Sci Trans' Med, 2013. 5(187): p. 187ra72]. In mice this can be further restricted to 5 μl per nostril. This small volume will still allow for testing in mice the maximal dose of GTP101 proposed in the nonclinical studies.

3 dose groups, 10 animals per dose per time point (5 males and 5 females), control (PBS), $3.2\times10^{10}$, $3.2\times10^{11}$, and $3.2\times10^{12}$ GC/kg of IP (see following table). Day 0 is IP administration, day 10 is peak expression, and day 60 is recovery period. Safety assessments include body weights, clinical observations, serum chemistries and hematology at sacrifice, full necropsy, organ weights and storage of tissues at each sacrifice, histopathology only on selected tissues—lung, brain, liver, kidney, heart on high dose and control. Histopathology on mid and low dose group will be performed only if abnormalities are observed at highest dose. Expression of two transgenes will be assessed by sandwich ELISA at the time of sacrifice in the nasal lavage fluid (NLF), BALF and serum. Immunology studies will evaluate the levels of anti-drug antibody (ADA) by ELISA (transgenes and capsid) and the levels of T-cell responses evaluated in spleen.

Non-GLP Pilot Toxicology Study in Immunocompetent CD1 Mice

| Dose (GC/kg) | Necropsy time point (d) | Number of male CD1 mice per group | Number of female CD1 mice per group |
|---|---|---|---|
| $3.2\times10^{10}$ | 10 | 5 | 5 |
| | 60 | 5 | 5 |
| $3.2\times10^{11}$ | 10 | 5 | 5 |
| | 60 | 5 | 5 |
| $3.2\times10^{12}$ | 10 | 5 | 5 |
| | 60 | 5 | 5 |
| PBS | 10 | 5 | 5 |
| | 60 | 5 | 5 |

B. Toxicology Study in Immunodeficient Mice

This toxicology study is performed as the maximal dose proposed for humans, which is roughly $3.2\times10^{11}$ GC/kg in RAG-1 KO mice and the middle dose group used for previous studies. Group size will be 10 animals per time point, per sex, with sacrifices at days 10 and 60. IP will be administered in a volume of up to 10 μl per nostril.

Nonclinical Toxicology Study in Immunodeficient Mice

| Dose | Necropsy time point | Number of male Rag-1 KO mice per group | Number of female Rag-1 KO mice per group |
|---|---|---|---|
| $3.2\times10^{11}$ GC/kg | 10 | 10 | 10 |
| | 60 | 10 | 10 |
| PBS | 10 | 10 | 10 |
| | 60 | 10 | 10 |

One dose group, 20 animals per dose per time point (10 males and 10 females), dose at $3.2\times10^{11}$ GC per mouse of IP. Day 0 is IP administration, day 10-peak expression, and day 60-recovery period. Safety assessments include body weights, clinical observations, serum chemistries and hematology at sacrifice, full necropsy, organ weights and storage of tissues at each sacrifice, histopathology only on selected tissues (listed in Table 8.8) Histopathology of the low dose group will be performed only if abnormalities are observed at highest dose. Expression of two transgenes will be assessed by ELISA in both, NLF and BALF.

C. Toxicity and Biodistribution Studies in Nonhuman Primates

This study will be performed at a dose that represents 10-fold higher than the highest dose that will be delivered in the human trial using the same device and volumes used in the human trial when normalized according to total body mass. The highest dose in the human trial will be $3.2 \times 10^{11}$ GC/kg ($2.4 \times 10^{13}$ GC total for 75 kg human) administered via 2×0.2 ml per nostril. NHPs will receive $3.2 \times 10^{12}$ GC/kg ($1.28 \times 10^{13}$ GC for a 4 kg macaque), which is the highest dose that can be administered with the IMAD device at the volumes to be provided to humans which is $2.4 \times 10^{13}$ GC administered as 2×0.2 ml per nostril.

Toxicity and biodistribution studies will be performed in rhesus macaques. Six males and six females, to a total of 12 rhesus macaques will be used for this study. Three time points will be evaluated, naïve animals will be sacrificed on day 0 prior to IP administration, Day 10 corresponds to peak expression, and day 60 corresponds to long-term recover period.

Two males and two females will be sacrificed at each time point. Toxicity will be evaluated by assessing CBC/chem panels.

EXAMPLE 8

Assessment of Intranasal Delivery Device

In the next set of studies, the ability of AAV9 expressing anti-influenza A and B antibodies (FI6 and CR8033, respectively) coupled with the LMA® MAD Nasal™ intranasal mucosal atomization device (IMAD) to effectively protect mice against challenge with pandemic or seasonal influenza is assessed. First, it was determined that an equimolar combination of AAV9.FI6 and AAV9.CR8033 vectors delivered intranasally (i.n.) at a dose of $5 \times 10^{10}$ GC/KG (or $1 \times 10^9$ GC) per mouse effectively protected mice against lethal challenge with influenza A (mouse adapted H1N1, PR8) or influenza B (mouse adapted B/Lee/40), respectively (FIGS. 11A, 11D, 11G and 12A, 12D). In an effort to progress AAV9 into the clinic, vector compatibility with the IMAD for loss in volume and vector potency was assessed. For these studies, 0.5 mL of vector suspension was plunged through the IMAD to evaluate physical loss of vector solution as well as to evaluate the impact of the device on vector potency. As indicated in FIG. 12G, a physical liquid loss of 4-6.6% of initial volume was observed when the vector solution was processed through the IMAD. We also evaluated three different vector formulations: PBS-pH 6.8, PBS-pH 7.2 or PBS-pH 7.4 for vector compatibility. Groups of mice were i.n. administered a mixture of $5 \times 10^{10}$ GC/KG (or $1 \times 10^9$ GC) each of AAV9.FI6 and AAV9.CR8033 as well as a mixture of $5 \times 10^{10}$ GC/KG (or $1 \times 10^9$ GC) each of AAV9.FI6 and AAV9.CR8033 that was processed through the IMAD. Seven days later, the mice were challenged with 5LD50 of PR8 or B/Lee/40 (FIGS. 11A, 11D, 11G and 12A, 12D). No difference in effectiveness of protection against influenza A or B was observed when the vector mixture was processed through the IMAD (dark grey squares). Additionally the use of the IMAD was compatible with the three different formulations and no diminution of effectiveness was observed when vector formulated with each of the three formulations was processed through the IMAD. Only vector-administered mice survived the challenge. At the conclusion of the experiment (Day 21) mice were sacrificed and the bronchoalveolar lavage fluid (BALF) harvested to evaluate antibody expression. The lungs were also harvested to assess the amount of vector genome present at time of necropsy. No difference was observed in the expression of the antibody at the airway surfaces when vector was delivered as liquid or as liquid following IMAD processing (FIGS. 11B, 11E, 11H and 12B, 12E). Furthermore, no significant difference in the number of AAV9 vector genomes in the lung was observed.

Next this approach was translated to the nose of macaques, a model more closely related to the human nose that is the target tissue. In this model, the kinetics of the onset of transgene expression in the nasal lavage fluid (NLF) and stability of expression was assessed when AAV9 vector was delivered via the IMAD compared to the traditional, direct liquid delivery Immune responses against the human antibody FI6 or CR8033 would have confounded the experiment and interpretation of the results. As such, in these studies a self antigen (rhesus a-fetoprotein, rhAFP) was used as the reporter transgene. Expression of rhesus alpha fetoprotein (rhAFP) here is noted by the presence of a plus (+) sign as accurate quantification of the amount of antibody at the mucosal surfaces is constrained by the accurate sampling of the NLF (FIG. 13). At the conclusion of the study, vector biodistribution was also examined. Overall, no significant differences in the kinetics and profile of gene expression or AAV9 vector biodistribution were observed between the two delivery methods.

In conclusion, AAV-mediated prophylaxis against influenza A and B is safe and effective when vectors are delivered via the IMAD, an easy-to-use device that localizes transduction to the site of influenza infection, the nasal mucosa.

EXAMPLE 9

Initial Phase 1 Trial Design

The objective of the phase 1 trial is to evaluate preliminary safety and tolerability, to understand the pharmacokinetics of the IP in healthy volunteers, and to select a dose level for further development. The trial will be an open label, dose-escalation trial with the dose levels based on preclinical data. The study will enroll up to five cohorts, with four subjects per cohort. Subjects will be screened 4-12 weeks prior to treatment and will be followed for up for 6 months.

Each volunteer will receive one 0.8 ml dose of IP IN via two sequential applications of 0.2 ml per nostril into each nostril using the approved IMAD. Up to twenty eight (24) volunteers will be enrolled in five cohorts. Cohorts 1-4 will receive increasing dosage levels of IP with the final cohort (cohort 5) expanded to 8 volunteers at the optimal dose level (defined by safety and pharmacokinetic parameters in cohorts 1-4).

Initial Phase 1 Study Design in Healthy Adult Volunteers

| Cohort | N active | AAV2/9 Transgene Product Dosage Level (GC) | Total volume to be administered (ml) | Administration Route |
|---|---|---|---|---|
| 1 | 4 | $3.0 \times 10^{12}$ | 0.2 ml per each nostril; two sets of applications, 0.8 ml total | IN |
| 2 | 4 | $6.0 \times 10^{12}$ | | IN |
| 3 | 4 | $1.2 \times 10^{13}$ | | IN |
| 4 | 4 | $2.4 \times 10^{13}$ | | IN |
| 5 | 8 | Optimal dose | 0.2 ml per each nostril; two sets of applications, 0.8 ml total | IN |
| Total | 24 | | | |

A. Target Population Inclusion/Exclusion Criteria

Healthy 18-45 years old adults of any gender with body mass index of 19-30 kg/m² and body weight of 50-100 kg will be enrolled to evaluate safety, immunologic and pharmacokinetic parameters of GTP101.

Inclusion Criteria
- Male or female aged 18-45 years inclusive
- Able to give written informed consent to participate
- Healthy, as determined by medical history, physical examination, vital signs, and clinical safety laboratory examinations @ baseline
- Non-habitual smoker (habitual smokers are persons who smoke more than 4 cigarettes or other tobacco products on a weekly basis) and agree to not use tobacco products during participation
- Females should fulfill one of the following criteria:
- At least one year post-menopausal;
- Surgically sterile;
- Will use oral, implantable, transdermal or injectable contraceptives for 30 days prior to IP administration and until 60 days after vaccination;
- Willing to abstain from sexual intercourse or use another reliable form of contraception approved by the Investigator (e.g., intrauterine device (IUD), female condom, diaphragm with spermicide, cervical cap, use of condom by the sexual partner or a sterile sexual partner) from the time of screening through Study Day 28.
- Women of childbearing potential must have a negative urine pregnancy test within 24 hours preceding IP administration
- Comprehension of the study requirements, expressed availability for the required study period Exclusion Criteria
- Significant history of seasonal hay fever or a seasonal allergic rhinitis or perennial allergic rhinitis or chronic or nasal or sinus condition
- History of asthma requiring treatment for up to 1 year prior to administration of IP
- Subjects with abnormal nasal structure including septal deviation and nasal polyps, chronic sinusitis, asthma, or COPD
- Current use of intranasal steroids.
- Presence of significant uncontrolled medical or psychiatric illness (acute or chronic) as assessed by the Investigator. This includes, but is not limited to, institution of new medical or surgical treatment, or a significant dose alteration for uncontrolled symptoms or drug toxicity within 3 months of screening and reconfirmed on Day 0 prior to challenge.
- Positive serology for HIV-1 or HIV-2, or HBsAg or HCV antibodies.
- Cancer, or treatment for cancer, within 3 years, excluding basal cell carcinoma or squamous cell carcinoma, which is allowed.
- Presence of immunosuppression or any medical condition that may be associated with impaired immune responsiveness, including, but not limited to, diabetes mellitus.
- Presently receiving (or history of receiving), during the preceding 3-month period, any medications or other treatments that may adversely affect the immune system such as allergy injections, immune globulin, interferon, immunomodulators, cytotoxic drugs or other drugs known to be frequently associated with significant major organ toxicity, or systemic corticosteroids (oral or injectable). Topical corticosteroids will be allowed.
- History of drug or chemical abuse in the year before the study.
- Receipt of any investigational product or nonregistered drug within the 30 days prior to administration of IP or currently enrolled in any investigational drug study or intends to enroll in such a study within the ensuing study period.
- Receipt of blood or blood products 6 months prior to IP administration or planned administration during the study period.
- Acute disease within 72 hours prior to IP administration, defined as the presence of a moderate or severe illness with or without fever (as determined by the Investigator through medical history and physical examination), or presence of a fever ≥38° C. orally.
- Pregnant and/or lactating females.
- Serum antibodies to the AAV2/9 of >1:80.
- Any condition that, in the opinion of the Investigator, might interfere with the primary study objectives and assessments.

B. Dose Level Determination

Initial dose levels have been chosen based on preclinical efficacy data, and will be refined based on nonclinical safety assessments, with the highest dose limited by the aggregation properties of AAV. Doses will range from $3.0 \times 10^{12}$ to $2.4 \times 10^{13}$ GC/dose administered in 4×0.2 ml per nostril via IMAD. These doses are substantially lower than those given to monkeys, mice and ferrets when adjusted for total body mass. No substantial toxicity was observed in any nonclinical studies conducted in these species at any dose with the IP or versions of AAV2/9 similar in structure to the IPs planned for the clinical trial.

C. Dosage Administration and Duration

Each dose group will receive IP in 0.4 ml per each nostril via IMAD. Subjects will be dosed one by one. Treatment intervals within the same dose group would be determined by the nonclinical studies but for purposes of presentation will be 1 week. Once all subjects in one cohort have passed study day 14, preliminary safety data will be reviewed. If no safety issues are identified, dose escalation to the next dose will commence. After completion of cohort 4 and preliminary safety for the highest dose is demonstrated, a fifth and final cohort will be enrolled for expansion for a total of 8 subjects (i.e., 4 additional subjects) at the optimal dose which will be the Maximally Tolerated Dose or the highest dose that can be administered.

The product administered to patients will be a mixture of two AAV2/9 vectors which have been combined at the time of fill/finish. Administration of the IP will occur in two sequential 0.2 ml doses into each nostril (i.e., total of 0.8 ml of IP). The IP will be administered using a commercially approved device manufactured by Teleflex Medical (Teleflex.com). The device is called the LMA MAD NASAL™ (Intranasal Mucosal Atomization Device). Details as to how best use the device to deliver IP to nasal mucosa are provided in the company's Procedure Guide. Basically, the subject is placed in a recumbent position and the tip of the device is placed at the orifice of each nasal passage (one at a time) after which the IP is delivered by pushing the fluid through the atomizer via a syringe.

The maximum tolerated dose (MTD) will be defined as the dose below the dose at which the subjects demonstrate dose-limiting toxicity (DLT), defined as any treatment related Grade 3 in two subjects or one treatment related Grade 4 event.

This application contains sequences and a sequence listing, which is hereby incorporated by reference. Also incorporated by reference herein is US Provisional Patent Application No. 62/323,348, filed Apr. 15, 2016 and US Provisional Application No. 62/161,192, filed May 13, 2015. All publications, patents, and patent applications cited in this application, are hereby incorporated by reference in their entireties as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications can be made thereto without departing from the spirit or scope of the appended claims.

TABLE (Sequence Listing Free Text)
The following information is provided for sequences containing free text under numeric identifier <223>.

| SEQ ID NO | Free Text under <223> |
|---|---|
| 1 | <220> <223> Plasmid carrying FI6cc HC with germline light chain <220> <221> repeat_region <222> (1) . . . (130) <223> 5' ITR <220> <221> repeat_region <222> (198) . . . (579) <223> CMV IE promoter <220> <221> promoter <222> (582) . . . (862) <220> <221> TATA_signal <222> (836) . . . (839) <220> <221> Intron <222> (956) . . . (1928) <223> chicken beta-actin intron <220> <221> misc_feature <222> (1940) . . . (1987) <223> c-myc 5'UTR <220> <221> misc_feature <222> (1988) . . . (1992) <223> kozak <220> <221> misc_feature <222> (1993) . . . (2052) <223> leader <220> <221> CDS <222> (2053) . . . (2439) <223> FI6 variable heavy <220> <221> CDS <222> (2440) . . . (2760) <223> FI6 CH1 <220> <221> CDS <222> (2761) . . . (3426) <223> FI6 CH2-3 <220> <221> misc_feature <222> (3427) . . . (3438) <223> furin cleavage site <220> <221> misc_feature <222> (3439) . . . (3510) <223> F2A <220> <221> misc_feature <222> (3511) . . . (3570) <223> leader <220> <221> CDS <222> (3511) . . . (3570) |

TABLE-continued (Sequence Listing Free Text)
The following information is provided for sequences containing free text under numeric identifier <223>.

| SEQ ID NO | Free Text under <223> |
|---|---|
| | <223> leader <220> <221> CDS <222> (3571) . . . (3909) <223> kagga germline line <220> <221> CDS <222> (3910) . . . (4230) <220> <221> repeat_region <222> (4308) . . . (4432) <223> rabbit globin polyA <220> <221> repeat_region <222> (4521) . . . (4650) <223> 3' ITR <220> <221> misc_feature <222> (4827) . . . (5265) <223> F1 ori on complementary strand <220> <221> misc_feature <222> (5294) . . . (5936) <223> origin of replication <220> <221> misc_feature <222> (6611) . . . (7426) <223> CDS for Kan resistance located on complementary strand |
| 8 | <223> Cls plasmid containing CR8033 heavy chain and light chain from kappa germline <220> <221> misc_feature <222> (264) . . . (287) <223> CMV promoter end <220> <221> promoter <222> (285) . . . (565) <223> CB promoter <220> <221> misc_feature <222> (288) . . . (318) <223> begin promoter <220> <221> TATA_signal <222> (539) . . . (542) <220> <221> Intron <222> (659) . . . (1631) <223> chicken beta-actin intron <220> <221> misc_feature <222> (1517) . . . (1533) <223> end of intron <220> <221> misc_feature <222> (1643) . . . (1690) <223> c-myc 5' UTR <220> <221> misc_feature <222> (1691) . . . (1698) <223> kozak <220> <221> CDS <222> (1753) . . . (2133) <223> CR8033cc variable heavy <220> <221> CDS <222> (2134) . . . (2454) <223> CH1 <220> <221> CDS <222> (2455) . . . (3120) |

TABLE-continued (Sequence Listing Free Text)
The following information is provided for sequences containing free text under numeric identifier <223>.

| SEQ ID NO | Free Text under <223> |
|---|---|
| | <223> CH2-3 |
| | <220> |
| | <221> misc_feature |
| | <222> (3121) ... (3132) |
| | <223> furin cleavage site |
| | <220> |
| | <221> misc_feature |
| | <222> (3133) ... (3204) |
| | <223> F2A linker |
| | <220> |
| | <221> CDS |
| | <222> (3265) ... (3603) |
| | <223> Kappa germline light |
| | <220> |
| | <221> CDS |
| | <222> (3604) ... (3924) |
| | <223> constant light |
| | <220> |
| | <221> polyA_signal |
| | <222> (4000) ... (4126) |
| | <220> |
| | <221> repeat_region |
| | <222> (4215) ... (4344) |
| | <223> 3' ITR (on complement) |
| | <220> |
| | <221> misc_feature |
| | <222> (4521) ... (4959) |
| | <223> F1 ori on complementary strand |
| | <220> |
| | <221> misc_feature |

TABLE-continued (Sequence Listing Free Text)
The following information is provided for sequences containing free text under numeric identifier <223>.

| SEQ ID NO | Free Text under <223> |
|---|---|
| | <223> (4988) ... (5630) |
| | <223> pUC origin of replication |
| | <220> |
| | <221> misc_feature |
| | <222> (7363) ... (7548) |
| | <223> Lac promoter |
| | <220> |
| | <221> repeat_region |
| | <222> (7603) ... (7732) |
| | <223> 5' ITR |
| | <220> |
| | <221> misc_feature |
| | <222> (7806) ... (7835) |
| | <223> promoter start |
| 14 | <223> include leader-entire heavy chain-furin-F2A linker-leader-entire light chain |
| 15 | <223> IF16 11 eader-entire heavy chain-furin-F2A linker-leader-entire light chain |
| 16 | <223> F16 26 |
| 17 | <223> F16 28 |
| 18 | <223> F16 30 cDNA |
| 19 | <223> F16 35 cDNA |
| 21 | <223> F16 cDNA |
| 22 | <223> F16 42 cDNA |
| 23 | <223> F16 B42 |
| 24 | <223> mutated IL2 |
| 25 | <223> mutated IL2 |

---

The invention claimed is:

1. A composition useful for delivering a combination of two anti-influenza antibody constructs for passive immunization against influenza infection, the composition comprising:
   (a) a first non-replicating recombinant adeno-associated virus having an AAV9 capsid (rAAV9) and having a vector genome which comprises: (i) an AAV inverted terminal repeat (ITR), (ii) an enhancer, (iii) a chicken beta-actin promoter, (iv) an intron, (v) a 5' UTR, (vi) a nucleic acid sequence encoding a leader peptide operably linked to an FI6v3 heavy chain (HC) variable region, (vii) a nucleic acid sequence encoding the FI6v3 HC variable region having an amino acid sequence of SEQ ID NO:2, (viii) a nucleic acid sequence encoding a human heavy chain (HC constant region), (ix) a furin recognition site, (x) an F2A linker, (xi) a nucleic acid sequence encoding a leader peptide operably linked to an immunoglobulin light chain (LC), (xii) a nucleic acid sequence encoding the immunoglobulin light chain (LC) which is a germline antibody sequence with no defined specificity comprising an amino acid sequence of SEQ ID NO: 6 and SEQ ID NO: 7, (xiii) a polyadenylation signal, and (xiv) an AAV inverted terminal repeat; and
   (b) a second non-replicating rAAV9, wherein the second rAAV9 has an AAV9 capsid and a vector genome which comprises: (i) an AAV inverted terminal repeat (ITR), (ii) an enhancer, (iii) a chicken beta-actin promoter, (iv) an intron, (v) a 5' UTR, (vi) a nucleic acid sequence encoding a leader peptide operably linked to a CR8033 heavy chain (HC) variable region, (vii) a nucleic acid sequence encoding the CR8033 HC variable region having an amino acid sequence of SEQ ID NO: 9, (viii) a nucleic acid sequence encoding a human heavy chain (HC) constant region, (ix) a nucleic acid sequence encoding a furin recognition site, (x) an F2A linker, (xi) a nucleic acid sequence encoding a leader peptide operably linked to an immunoglobulin light chain (LC), (xii) a nucleic acid sequence encoding the immunoglobulin light chain (LC) which is a germline antibody sequence with no defined specificity comprising an amino acid sequence of SEQ ID NO: 12 and SEQ ID NO: 13, (xiii) a polyadenylation signal, and (xiv) an AAV inverted terminal repeat;
   and an aqueous liquid suspension base.

2. The composition according to claim 1, wherein the vector genome for (a) is selected from SEQ ID NOs: 1, 14, 15, or 16.

3. The composition according to claim 1, wherein the vector genome for (b) comprises SEQ ID NO: 8.

4. The composition according to claim 1, wherein the total concentration of rAAV9 from (a) and (b) is about $1 \times 10^{11}$ to about $6 \times 10^{13}$ genome copies (GC)/mL, wherein GC is as determined using digital droplet PCR (ddPCR).

5. The composition according to claim 1, wherein the ratio of the first rAAV9 of (a) to the second rAAV9 of (b) is about 1:1.

6. The composition according to claim 1, wherein the 5' UTR of (a) or (b) are independently selected from a human c-myc 5' UTR.

7. The composition according to claim 1, wherein the leader peptide is an IL-2 leader peptide.

8. The composition according to claim 1, wherein the composition is formulated for intranasal administration.

9. The composition according to claim 1, wherein the composition is formulated for intramuscular or intravenous administration.

10. A method for immunizing human patients against influenza, the method comprising administering an effective amount of a composition according to claim 1.

11. The method according to claim 10, wherein the patient is administered a dose in an amount of about $1 \times 10^{12}$ to about $3 \times 10^{13}$ GC.

12. The method according to claim 10, wherein the composition is administered intranasally in a single nostril.

13. The method according to claim 10, wherein the composition is administered intranasally to each nostril.

14. The method according to claim 10, wherein the patient is administered two sequential applications of about 0.4 mL per nostril.

15. The method according to claim 10, wherein the composition is administered intramuscularly or intravenously.

16. A product which comprises a container comprising a composition according to claim 1, optional diluent, and instructions for administration.

17. A composition useful for delivering a combination of two anti-influenza antibody constructs for passive immunization against influenza infection, the composition comprising:
(a) a first non-replicating recombinant adeno-associated virus (rAAV) having a vector genome which comprises: (i) an AAV inverted terminal repeat (ITR), (ii) an enhancer, (iii) a promoter, (iv) an intron, (v) a 5' UTR, (vi) a nucleic acid sequence encoding a leader peptide operably linked to an FI6v3 heavy shain (HC) variable region, (vii) a nucleic acid sequence encoding the FI6v3 heavy chain variable region, the FI6v3 HC variable region having an amino acid sequence of SEQ ID NO:2, (viii) a nucleic acid sequence encoding a human HC constant region, (ix) a nucleic acid sequence encoding a suitable linker, (x) a nucleic acid sequence encoding a leader peptide operably linked to an immunoglobulin light chain, (xi) at least one nucleic acid sequence encoding the immunoglobulin light chain which is a germline sequence with no defined specificity comprising an amino acid sequence of SEQ ID NO: 6 and SEQ ID NO: 7, (xii) a polyadenylation signal, and (xiii) an AAV inverted terminal repeat; and
(b) a second non-replicating rAAV, wherein the second rAAV has a vector genome which comprises: (i) an AAV inverted terminal repeat (ITR), (ii) an enhancer, (iii) a promoter, (iv) an intron, (v) a 5' UTR, (vi) a nucleic acid encoding a leader peptide operably linked to a CR8033 heavy chain (HC) variable region, (vii) a nucleic acid sequence encoding the CR8033 HC variable region having an amino acid sequence of SEQ ID NO: 9, (viii) a nucleic acid sequence encoding a human HC constant region, (ix) a nucleic acid sequence encoding a suitable linker, (x) a nucleic acid sequence encoding a leader peptide operably linked to an immunoglobulin light chain, (xi) at least one nucleic acid sequence encoding the immunoglobulin light chain which is a germline sequence with no defined specificity comprising an amino acid sequence of SEQ ID NO: 12 and SEQ ID NO: 13, (xii) a polyadenylation signal, and (xiii) an AAV inverted terminal repeat;
and an aqueous liquid suspension base.

18. The composition according to claim 17, wherein the non-replicating rAAV of (a) and (b) further comprises an AAV9 capsid.

19. The composition according to claim 17, wherein the suitable linker for (a) and/or (b) is independently selected from an IRES and an F2A.

20. The composition according to claim 17, wherein the promoter for (a) and/or (b) is independently selected from a chicken beta-actin (CB) promoter, a human cytomegalovirus (CMV) promoter, an early and a late promoters of simian virus 40 (SV40), a U6 promoter, metallothionein promoters, an EFIα promoter, a ubiquitin promoter, a hypoxanthine phosphoribosyl transferase (HPRT) promoter, a dihydrofolate reductase (HDFR) promoter, an adenosine deaminase promoter, a phosphoglycerol kinase (PGK) promoter, a pyruvate kinase promoter, a phosphoglycerol mutase promoter, a beta-actin promoter, a UbB, a UbC, or a thymidine kinase promoter of Herpes Simplex Virus.

21. The composition to claim 20, wherein the promoter is a chicken beta-actin (CB) promoter.

* * * * *